(12) United States Patent
Singh et al.

(10) Patent No.: US 12,117,447 B2
(45) Date of Patent: Oct. 15, 2024

(54) METAL NANOPARTICLES AND METHODS OF MAKING SAME

(71) Applicant: SONA NANOTECH INC., Halifax (CA)

(72) Inventors: Kulbir Singh, Antigonish (CA); Michael Mcalduff, Antigonish (CA); D. Gerrard Marangoni, Antigonish (CA)

(73) Assignee: Sona Nanotech Inc., Vancouver (CA)

( * ) Notice: Subject to any disclaimer, the term of this patent is extended or adjusted under 35 U.S.C. 154(b) by 301 days.

(21) Appl. No.: 16/761,473

(22) PCT Filed: Nov. 2, 2018

(86) PCT No.: PCT/CA2018/000205
§ 371 (c)(1),
(2) Date: May 4, 2020

(87) PCT Pub. No.: WO2019/084661
PCT Pub. Date: May 9, 2019

(65) Prior Publication Data
US 2020/0390908 A1 Dec. 17, 2020

(51) Int. Cl.
| | | |
|---|---|---|
| *G01N 33/574* | (2006.01) | |
| *A61K 9/20* | (2006.01) | |
| *A61K 41/00* | (2020.01) | |
| *A61K 47/68* | (2017.01) | |
| *A61K 49/00* | (2006.01) | |
| *B22F 1/054* | (2022.01) | |
| *B22F 9/24* | (2006.01) | |
| *C07C 211/63* | (2006.01) | |
| *C07K 14/005* | (2006.01) | |
| *C07K 16/00* | (2006.01) | |
| *C07K 17/14* | (2006.01) | |
| *G01N 33/543* | (2006.01) | |
| *B82Y 5/00* | (2011.01) | |
| *B82Y 15/00* | (2011.01) | |
| *B82Y 40/00* | (2011.01) | |

(52) U.S. Cl.
CPC ......... *G01N 33/574* (2013.01); *A61K 9/2072* (2013.01); *A61K 41/0052* (2013.01); *A61K 47/6835* (2017.08); *A61K 49/0002* (2013.01); *B22F 1/0547* (2022.01); *B22F 1/0549* (2022.01); *B22F 9/24* (2013.01); *C07C 211/63* (2013.01); *C07K 14/005* (2013.01); *C07K 16/00* (2013.01); *C07K 17/14* (2013.01); *G01N 33/54346* (2013.01); *B22F 2301/255* (2013.01); *B82Y 5/00* (2013.01); *B82Y 15/00* (2013.01); *B82Y 40/00* (2013.01); *C12N 2740/16111* (2013.01)

(58) Field of Classification Search
CPC .............. A61K 49/0002; A61K 9/2072; A61K 41/0052; A61K 47/6835; A61K 49/0428; B22F 1/0547; B22F 9/24; B22F 2301/255; B22F 1/0549; C07C 211/63; C07K 16/005; C07K 14/005; C07K 17/14; G01N 33/54346; G01N 33/574; G01N 33/532; G01N 33/558; G01N 33/587; G01N 33/553; B82Y 5/00; B82Y 15/00; B82Y 40/00; B82Y 30/00; C12N 2740/16111; C22C 5/02; C22C 1/0466; A61P 35/00
See application file for complete search history.

(56) References Cited

U.S. PATENT DOCUMENTS

| | | |
|---|---|---|
| 2,374,354 A | 4/1945 | Kaplan |
| 2,524,218 A | 10/1950 | Bersworth |
| 2,530,147 A | 11/1950 | Bersworth |
| 3,244,724 A | 4/1966 | Guttmann |
| 4,162,282 A | 7/1979 | Fulwyler et al. |
| 4,310,505 A | 1/1982 | Baldeschwieler et al. |
| 4,533,254 A | 8/1985 | Cook et al. |
| 4,728,575 A | 3/1988 | Gamble et al. |
| 4,737,323 A | 4/1988 | Martin et al. |
| 4,921,706 A | 5/1990 | Roberts et al. |
| 5,160,450 A | 11/1992 | Okahara et al. |
| 5,432,260 A | 7/1995 | Stahl |
| 5,786,214 A | 7/1998 | Holmberg |
| 5,871,727 A | 2/1999 | Curiel |
| 5,939,277 A | 8/1999 | Rakowicz-Szulcynska |
| 6,107,090 A | 8/2000 | Bander |
| 6,391,818 B1 | 5/2002 | Bonsel et al. |
| 7,892,317 B2 | 2/2011 | Rahman Nia |
| 8,641,798 B2 | 2/2014 | Hight-Walker et al. |

(Continued)

FOREIGN PATENT DOCUMENTS

| | | |
|---|---|---|
| CA | 3079759 A1 | 5/2019 |
| CN | 103675264 B | 5/2015 |

(Continued)

OTHER PUBLICATIONS

Gao et al., Chem. Commun., 2015, 51, p. 843-6. (Year: 2015).*
Safety Assessment of Alkyl Betaines used in Cosmetics, 2014, https://www.cirsafety.org/sites/default/files/alkbet032014final_0.pdf (Year: 2014).*
Extended European Search Report for Application No. 18873610.2; Patent No. 3703886; PCT/CA2018000205, dated Sep. 4, 2021, 10 pages.
Xu Y. et al—Large-Scale, Low-Cost Synthesis of Monodispersed Gold Nanorods Using a Gemini Surfactant; Nanoscale Journal; (2015) Issue 15.
Zhu et al., Preparation and Surface Active Properties of Amphipathic Compounds with Two Sulfate Groups and Two Lipophilic Alkyl Chains; JAOCS, (Jul. 1990), vol. 67, No. 7, pp. 459-462.

(Continued)

*Primary Examiner* — Michael G. Hartley
*Assistant Examiner* — Leah H Schlientz
(74) *Attorney, Agent, or Firm* — Boyle Fredrickson, S.C.

(57) ABSTRACT

A method for making metal nanorods comprises combining a source of metal cations with at least one surfactant to form a mixture, wherein the metal cations are reduced and the metal nanorods are produced. Metal nanorods produced by the method and uses thereof. The metal nanorods are useful in devices such as lateral flow devices.

35 Claims, 26 Drawing Sheets

(56) References Cited

U.S. PATENT DOCUMENTS

| | | | |
|---|---|---|---|
| 9,487,399 B2 | 11/2016 | Ghanavi et al. | |
| 2008/0100279 A1* | 5/2008 | Mohapatra | C12Q 1/32 977/762 |
| 2010/0233812 A1* | 9/2010 | Sun | C01G 23/047 95/45 |
| 2011/0189483 A1 | 8/2011 | Zubarev et al. | |
| 2011/0215277 A1* | 9/2011 | Khan | B01J 8/00 252/408.1 |
| 2013/0122321 A1 | 5/2013 | Karandikar et al. | |
| 2013/0272919 A1* | 10/2013 | Kim | B82Y 40/00 75/343 |
| 2014/0134041 A1* | 5/2014 | Hotta | H01B 1/22 252/514 |
| 2014/0194749 A1* | 7/2014 | Fixler | A61B 5/0075 600/473 |
| 2015/0183028 A1 | 7/2015 | Bhagavatula et al. | |
| 2016/0051955 A1 | 2/2016 | Wei et al. | |
| 2016/0114389 A1 | 4/2016 | Kim et al. | |
| 2016/0114398 A1 | 4/2016 | Kim et al. | |
| 2020/0390908 A1 | 12/2020 | Singh et al. | |

FOREIGN PATENT DOCUMENTS

| | | | |
|---|---|---|---|
| CN | 103691968 B | 7/2016 | |
| EP | 2156910 A1 * | 2/2010 | B22F 1/0022 |
| EP | 2810052 B1 | 12/2017 | |
| EP | 3703886 A1 | 9/2020 | |
| JP | 2017179546 A | 10/2017 | |
| WO | 2019084661 | 5/2019 | |

OTHER PUBLICATIONS

Zhu et al., Preparation and Properties of Double- or Triple-Chain Surfactants with Two Sulfonate Groups Derived from N-Acyldiethanolamines, JAOCS, (Jul. 1991), vol. 68, No. 7, pp. 539-543.

Zhu et al., Relationship of Structure to Properties of Surfactants. 16. Linear Decyldiphenylether Sulfonates, JAOCS, (Jan. 1992), vol. 69, No. 1, pp. 30-33.

Zhu et al., Preparation and Properties of Glycerol-Based Double- or Triple-Chain Surfactants with Two Hydrophilic Ionic Groups JAOCS (Jul. 1992), vol. 69, No. 7, pp. 626-632.

Zhu et al., Preparation and Properties of Double-Chain Bis (Quaternary ammonium) Compounds, J. Jpn. Oil Chem. Soc. (1993), vol. 42, No. 3, pp. 161-167.

Zhu et al., Preparation and Properties of Double-Chain Surfactants Bearing Two Sulfonate Groups, J. Jpn. Oil Chem. Soc. (1991), vol. 42, No. 6, pp. 473-477.

A comprehensive review of lipid vesicles and methods for their preparation are described in "Liposome Technology" (1984. Gregoriadis G. ed. CRC Press Inc Boca Raton Florida vol. I II & III).

A "Tips and Tricks" Practical Guide to the Synthesis of Gold Nanorods; J. Phys Chem Ltt (2015) vol. 6, pp. 4270-4279.

Office Action for Korean Application No. 10-2020-7015935 dated Jan. 28, 2022.

Notification Concerning the Transmittal of International Preliminary Report on Patentability for PCT/CA2018/000205 dated May 14, 2020.

Zana, R. "Gemini Surfactants Synthesis, Interfacial and Solution-Phase Behavior, and Applications" (Surfactant Science Series vol. 117, Ed. R. Zana, 2003, Taylor & Francis Publishers, Inc.; Accessed from: https://books.google.ca/books?id=WEtYWJlb_LkC&printsec=frontcover&source=gbs_atb#v=onepage&q&f=false.

Aioub M. et al—Oxidative Damage Toward Healthy, Untreated Cells During Plasmonic Photothermal Therapy; ACS Nano; (2017) vol. 11, pp. 579-586.

Allen J. et al—Synthesis of Less Toxic Gold Banorods by Using Dodecylethyldimethylammonium Bromide as an Alternative Growth-Directing Surfactant; Journal of Colloid and Interface Science; (2017) vol. 505, pp. 1172-1176.

An L. et al—Small Gold Nanorods: Recent Advances in Synthesis, Biological Imaging, and Cancer Therapy; Materials, 2017,10, 1372-1394.

Casu A. et al—Controlled Synthesis of Gold Nanostars by Using a Zwitterionic Surfactant; Chemistry (2012) vol. 18, pp. 9381-9390.

Chang H. et al—Mini Gold Nanorods With Tunable Plasmonic Peaks Beyond 1000 nm; Chemistry of Materials; (2018) vol. 30, pp. 1427-1435.

Dou Y. et al—Self-Assembly and Accurate Preparation of Au Nanoparticles in the Aqueous Solution of a Peptide A6D and a Zwitterionic CI4DMAO; Soft Matter, 2013, 9, 5572-5580.

Gao et al., Dynamic Surface Tension of Aqueous Surfactant Solution. 6. Compounds Containing Two Hydrophilic Head Groups and Two or Three Hydrophobic Head Groups and Two or Three Hydrophobic Groups and Their Mixtures with Other Surfactants, JAOCS, (Jul. 1994) vol. 71. No. 7, pp. 771-776.

Gómez-Grañat S. et al—Surfactant (Bi) Layers on Gold Nanorods; Langmuir; (2012) vol. 28, pp. 1453-1459.

Gou L. et al—Fine-Tuning the Shape of Gold Nanorods; Chem Mater. (2005) vol. 17 pp. 3668-3672.

Guerrero-Martnez Andrés et al.—Gemini-Surfactant-Directed Self-Assembly of Monodisperse Gold Nanorods into Standing Superlattices; Angewandte Chemie International Edition; (2009), vol. 48, pp. 9484-9488.

Hait S.K. et al., Gemini Surfactants: A Distinct Class of Self-Assembling Molecules Current Science, (May 2002), vol. 82, No. 9, pp. 1101-1111.

Huang Y. et al—Size Tunable Synthesis of Gold Nanorods Using Pyrogallol as a Reducing Agent; Sci China Chem (2015) vol. 58, pp. 1759-1765.

Joshi P. et al—Conjugation of Antibodies to Gold Nanorods Through Fc Portion: Synthesis and Molecular Specific Imaging; Bioconjugate Chemistry, 2013, 24, 878-888.

Li D. et al—Gold/Oil Nanofluids Stabilized by a Gemini Surfactant and their Catalytic Property; I&EC Research (2013) vol. 52 pp. 8109-8113.

Li D. et al—Preparation and Stability of Gemini Surfactant Modified Gold Nanofluids; Chemical Journal of Chinese Universities; (2017) vol. 38, pp. 1829-1833.

Masuyama A. et al., Synthesis and Properties of Bis (taurine) Types of Double-Chain Surfactants, J. Japan Chem. Soc. (1992), vol. 41, No. 4, pp. 301-305.

Menger F. M. et al., Gemini Surfactants: Synthesis and Properties, J. Am. Chemical Soc., (1991) vol. 113, pp. 1451-1452.

Menger F. M. et al., Gemini Surfactants: A New Class of Self-Assembling Molecules, J. Am. Chem. Soc. (1993), vol. 115, pp. 10083-10090.

Mohmound N. et al—Antibacterial Activity of Gold Nanorods Against *Staphylococcus aureus* and Propionibacterium Acnes: Misinterpretations and Artifacts; International Journal of Nanomedicine (2017) vol. 12; pp. 7311-7322.

Murphy P. et al—Structural Control of Au and Au—Pd Nanoparticles by Selecting Capping Ligands with Varied Electronic and Stearic Effects; Canadian Journal of Chemistry; 2009, 87, 1641-1649.

Murphy C.,Nanocubes and Nanoboxes, Science (2002), vol. 298, 5601, ProQuest One Academic pp. 2139.

Murphy C. et al., Controlling the Aspect ratio of Inorganic Nanorods and Nonowires; Adv. Mater., (2002), vol. 14, No. 1, pp. 80-82.

Naoe K. et al—Use of Reverse Micelles to Make Either Spherical or Worm-like Palladium Nanocrystals: Influence of Stabilizing Agent on Nanocrystal Shape; Langmuir 2008, 24, 2792-2798.

Nikoobakht B. et al., Preparation and Growth Mechanism of Gold Nanorods (NRs) Using Seed-Mediated Growth Method, Chem. Mater, (2003) vol. 15, pp. 1957-1962.

Okahara M. et al., Surface Active Properties of New Types of Amphipathic Compounds with Two Hydrophilic Ionic Groups and Two Lipophilic Alkyl Chains, J. Japan Oil Chem. Soc., (1988), vol. 37, No. 9.

Park K. et al—Highly Concentrated Seed=Mediated Synthesis of Nonodispersed Gold Nanorods; Applied Material Interface (2017) vol. 9, pp. 26363-26371.

(56) References Cited

OTHER PUBLICATIONS

Perez-Juste J. et al—Gold Nanorods: Synthesis, Characterization and Applications; Coordination Chemistry Reviews (2005) pp. 1870-1901.

Ratto F. et al—Size and Shape Control in the Overgrowth of Gold Nanorods; J Nanopart Res. (2010) vol. 12; pp. 2029-2036.

Rosen M., Geminis: A New Generation of Surfactants, Chemtech, (Mar. 1993) pp. 30-33.

Scarabelli L. et al—Turning Gold Nanorod Synthesis Through Prereduction with Salicylic Acid; Chemistry of Materials; (2013) vol. 25; pp. 4232-4238.

Sun B. et al—In Situ Synthesis of Graphene Oxide/Gold Nanorods Theranostic Hybrids for Efficient Tumor Computed Tomography Imaging and Photothermal Therapy; Nano Reasarch; (2017) vol. 10, pp. 37-48.

Sun, Y. Silver Nanowires—Unique Templates For Functional Nanostructures, Nanoscale, (2010), vol. 2, pp. 1626-1642.

Tong W. et al—Control of Symmetry Breaking Size and Aspect Ratio in Gold Nanorods: Underlying Role of Silver Nitrate; J. Phys Chem.; (2017) vol. 121 pp. 3549-35559.

Tong W. et al—The Evolution of Size, Shape, and Surface Morphology of Gold Nanorods; ChemComm (2018).

Vijayaraghavan, P. et al—Synthesis of Multibranched Gold Nanoechinus Using a Gemini Cationic Surfactant and Its Application for Surface Enhanced Raman Scattering; Applied Materials & Interfaces; (2016) vol. 36; pp. 23909-23919.

Wang, W. et al—Cationic Gemini Surfactant-Assisted Synthesis of Hollow Au Nanostructures by Stepwise Reductions; Applied Materials & Interfaces; (2013) vol. 5; pp. 5709-5716.

Wang W. et al—Facile Synthesis of Two-dimensional Highly Branched Gold Nanostructures in Aqueous Solutions of Cationic Gemini Surfactant; CrystEngComm (2013) vol. 15, pp. 2648-2656.

Wang, H. et al, Nucleic Acid Conjugated Nanomaterials for Enhanced Molecular Recognition, ACS Nano (2009), vol. 3, No. 9, pp. 2451-2460.

Yan C. et al—Concentration Effect on Large Scale Synthesis of High Quality Small Gold Nanorods and their Potential Role in Cancer Theranostics; Materials Science & Engineering; (2018) vol. 87, pp. 120-127.

Yasum E. et al—Cancer Cell Sensing and Therapy Using Affinity Tag-Conjugated Gold Nanorods; Interface Focus; (2013).

Ye X. et al—Seeded Growth of Monodisperse Gold Nanorods Using Bromide-Free Surfactant Mixtures; Nano Letters; (2013); vol. 13, pp. 2163-2171.

Xiong W. et al—Matryoshka Caged Gold Nanorods: Synthesis Plasmonic Property and Catalytic Activity; Nano Research; pp. 63-80.

Xiao J. et al—Surfactant-Assisted, Shape Controlled Synthesis of Gold Nanocrystals; Nanoscale, 2011, 3, 1383-1395.

Xu F. et al—Synthesis and Crystal Structure of Gold Nanowires with Gemini Surfactants as Directing Agents; CHEMPHYSCHEM, 2014, 15, 3979-3986.

Xu J. et al—Synthesis and self-assembly of gold nanoparticles using gemini surfactant as a phase transfer reagent and stabilizer; Journal of Experimental Nanoscience, 2006, 1, 103-11.

Xu, J. et al—Synthesis of Monodisperse Gold Nanoparticles Stabilized by Gemini Surfactant in Reverse Micelles; Journal of Dispersion Science and Technology; (2005) vol. 26.

Xu J. et al—Synthesis and Optical Properties of Silver Nanoparticles Stabilized by Gemini Surfactant; Colloids and Surfaces A: Physicochemical and Engineering Aspects; (2006) vol. 273, Issues 1-2, pp. 179-183.

Xu X. et al—Shape Change and Color Gamut in Gold Nanorods, Dumbbells and Dog Bones; Adv. Function Material (2006) vol. 16, pp. 2170-2176.

Examination Report for Application No. 202017020830 dated Mar. 15, 2022, 11 pages.

Canadian Office Action; dated Aug. 31, 2022; pp. 1-4.

European Office Action, Mar. 30, 2023.

Michal M. Wojcik et al—Temperature-Controlled Liquid Crystalline Polymorphism of Gold Nanoparticles: Journal of Soft Matter; (2011) vol. 7, pp. 10561-10564.

Guozhong Coa et al—Template-Based Sythesis of Nanorod, Nanowire, and Nanotube Arrays; Advances in Colloid and Interface Science; (2008) vol. 136, pp. 45-64.

B.D. Busbee et al—An Improved Synthesis of High-Aspect-Ratio Gold Nanorods; Advanced Materials; (2003) vol. 15 pp. 414-416.

C.J. Murphy et al—Controlling the Aspect Ratio of Inorganic Nanorods and Nanowires; Advanced Materials: (2002) vol. 14, pp. 80-82.

Catherine J. Murphy et al—Controlling the Aspect Ratio of Inorganic Nanorods and Nanowires; Advanced Materials; 2002, vol. 14, pp. 80-82.

Canadian Office Action, Feb. 22, 2023.

Canadian Intellectual Property Office Action for Application No. 3,079,759 dated Sep. 22, 2023 (3 pages).

\* cited by examiner

METAL NANOPARTICLES AND METHODS OF MAKING SAME

CROSS-REFERENCE TO RELATED APPLICATIONS

This application is a national phase filing of international application no. International Patent Application No. PCT/CA2018/000205 filed on Nov. 2, 2018, which claims priority to U.S. Provisional patent application No. 62/581,669, filed on Nov. 4, 2017, the entire contents including the original claims' set of which are hereby expressly incorporated by reference into this application.

FIELD

The present invention relates to nanoparticles. In particular, the present invention relates to metal nanoparticles, compositions comprising metal nanoparticles, and methods of making metal nanoparticles such as metal nanorods.

BACKGROUND

Metal nanoparticles are useful in various applications. Metal nanoparticles, such as metal nanospheres and nanorods, are a particularly attractive type of metal nanoparticle for various applications. Metal nanorods have a variety of uses as a result of their strong absorption bands in a region extending from visible light to the near infrared, and it is possible to tune the absorption maxima of the metallic nanorod by simply controlling its configuration.

Metal nanorods have utility as near-infrared probes because modification of their surface enables changes in their physical properties. Metal nanorods are important building blocks for future applications in solar cells, cancer therapy, diagnostic imaging, and so forth.

Several methods are available for the manufacture of metal nanorods, including electrolytic, chemical reduction, and photoreduction methods. However, bulk solution synthetic methods for the production of metal nanorods often produce nanoparticles of varying sizes and shapes, and hence tend to have a relatively low yield of nanoparticles of the desired size and shape (Murphy, Science, 2002, 298: 2139-41).

More specifically, in electrolytic methods of gold nanorod production, a solution containing a cationic surfactant is electrolyzed with constant current and gold clusters are leached from a gold plate at the anode. In chemical reduction methods, a material such as $NaBH_4$ reduces chlorauric acid and gold nanorods are generated in-situ. These gold nanorods act as "seed particles" and their subsequent growth in solution results in gold nanorods. The length of the gold nanorods generated is influenced by the ratio of the "seed particles" to chlorauric acid in the growth solution, however strict control of the size and shape of the nanoparticles can be difficult to achieve and the resulting solutions often contain a mixture of many particle sizes and shapes that have to be carefully separated and purified.

Photoreduction methods involve adding chlorauric acid to substantially the same solution as that in the electrolytic method and using ultraviolet irradiation to affect the reduction of chlorauric acid. The irradiation time can also be controlled to generate longer rods.

It is evident that in the gold nanorod production methods listed above, gold nanorods of multiple sizes and shapes are produced, the number density of gold nanorods of a particular size and shape is often small, and/or "seed" particles of gold nanospheres are needed to grow longer gold nanorods. In addition, the aforementioned methods may only be performed on a relatively small-scale (typically producing milligram quantities of gold nanorods). In most cases, attempts to scale-up production leads to erosion of uniformity in shape and/or size of the resultant product gold nanorods and none of these processes have proven amenable for scale-up.

The methods most commonly used to produce gold nanorods are similar to the methods of Murphy (Adv. Mater., 2001, 13:1389) and El-Sayad (Chem. Mater., 2003, 15:1957), in which a seed solution of gold particles is produced by the reduction of a higher oxidation state gold compound in the presence of a significant concentration of a long chain cationic surfactant (cetyltrimethylammonium bromide, or CTAB). This method has been shown to produce well-defined gold nanorods but in small quantities (generally much less than 0.50 g). U.S. Patent Application Publication No. 2011/0189483 to Zubarev demonstrated the ability to produce true gram quantities of gold nanorods also using a seed-mediated method and by carefully controlling the reaction conditions with regards to the reduction techniques and choice of capping agents used.

Invariably, both of these methodologies require an amount of gold seed and a stabilizing reaction medium consisting of a significant quantity of a cytotoxic cationic surfactant, such as cetyltrimethylammonium bromide (CTAB). The average size and quality of the gold nanorods has been shown to depend on the average size of the seed particles, their quality, and their capping agent. For in-vivo applications of gold nanorods, possible side effects due to the usage of the cytotoxic cationic surfactant can be significant and, therefore, methods have been developed to exchange the cytotoxic surfactant with polymeric stabilizing agents. Although, in theory, it is possible to remove, coat, or exchange some of the cytotoxic surfactant, some gold nanorods are inevitably lost during the exchange process, thereby decreasing final yield, and there will always be some cytotoxic surfactant left on the nanorod surfaces that has a potential for release in in-vivo applications.

Hence, colloid chemists have achieved some control over gold nanorod particle size and shape; however, limited success has been demonstrated in producing gold nanorods without the presence of a cytotoxic stabilizing cationic surfactant and/or without the use of seed particles.

A need, therefore, exists for the development of a product, composition and/or method that obviates or mitigates at least one of the disadvantages described above or that provides a useful alternative.

SUMMARY OF THE INVENTION

In an aspect, there is provided a method for making metal nanorods, the method comprising: combining a source of metal cations with at least one surfactant to form a mixture, wherein the metal cations are reduced and the metal nanorods are produced.

With respect to the methods described herein, aspects are provided as follows in any suitable permutations: In another aspect, wherein at least one surfactant reduces the metal cations. In another aspect, wherein the combining further comprises combining at least one reducing agent for reducing the metal cations. In another aspect, wherein the at least one surfactant forms a stable surfactant composition. In another aspect, wherein the mixture is maintained at any suitable temperature that promotes the formation of metal nanorods. In another aspect, wherein the temperature is maintained at about 20° C. to about 50° C. In another aspect, wherein the mixture is maintained for any suitable time period that promotes the formation of metal nanorods. In another aspect, wherein the time period is up to about 24 hours. In another aspect, wherein combining further comprises a reducing agent. In another aspect, wherein the reducing agent is selected from the group consisting of ascorbic acid, glucose, glucosamine, hydroquinone, aluminum, calcium, hydrogen, manganese, potassium, sodium borohydride, sodium triacetoxyborohydride, compounds containing the $Sn^{2+}$ ion, such as tin(II) chloride, sulfite compounds, hydrazine, zinc-mercury amalgam, diisobutyl-aluminum hydride, oxalic acid, formic acid, phosphites, hypophosphites, phosphorous acid, dithiothreitol (DTT), compounds containing the $Fe^{2+}$ ion, such as iron(II) sulfate, carbon monoxide, carbon, tris(2-carboxyethyl)phosphine HCl, and combinations thereof. In another aspect, wherein the reducing agent is ascorbic acid and/or sodium borohydride. In another aspect, wherein an amount of the reducing agent is from about 0.001 wt % to about 0.002 wt %, from about 0.001 wt % to about 0.0018 wt %, or from about 0.0013 wt % to 0.0017 wt % based on the total weight of the mixture. In another aspect, wherein an amount of the at least one surfactant is from about 0.05 wt % to about 5 wt % based on the total weight of the mixture. In another aspect, wherein the at least one surfactant creates wormlike micelles. In another aspect, wherein the at least one surfactant comprises at least one positively charged moiety and/or at least one negatively charged moiety. In another aspect, wherein the positively charged moiety comprises at least one secondary amine, tertiary amine, or quaternary ammonium. In another aspect, wherein the negatively charged moiety comprises a carboxyl group. In another aspect, wherein the at least one surfactant comprises a first surfactant and a second surfactant, wherein the first surfactant and the second surfactant are different. In another aspect, wherein the first surfactant and the second surfactant have hydrocarbyl tails of substantially the same length. In another aspect, wherein the first surfactant creates worm-like micelles. In another aspect, wherein the second surfactant increases the solubility of the first surfactant. In another aspect, wherein the first surfactant and the second surfactant are independently selected from a zwitterionic surfactant and an amphoteric surfactant. In another aspect, wherein the first surfactant is an amphoteric surfactant and the second surfactant is a zwitterionic surfactant. In another aspect, wherein the zwitterionic surfactant is a compound of formula (I):

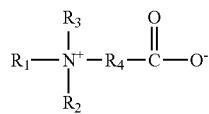

wherein:

$R_1$ represents a hydrophobic group, wherein the hydrophobic group comprises a substituted or unsubstituted hydrocarbon group, or a substituted or unsubstituted heterogeneous group;

$R_2$ and $R_3$ are each independently selected from hydrogen or a substituted or unsubstituted hydrocarbon group, or a substituted or unsubstituted heterogeneous group; and $R_4$ is a substituted or unsubstituted hydrocarbon group, or a substituted or unsubstituted heterogeneous group. In another aspect, wherein $R_1$ is selected from unsaturated or saturated alkyl, unsaturated or saturated aralkyl, unsaturated or saturated heteroaralkyl, unsaturated or saturated alkoxyalkyl, and unsaturated or saturated alkylamidoaikyl, wherein each group may be substituted or unsubstituted. In another aspect, wherein the alkyl of $R_1$ represents a group that contains from about 12 to 24 carbon atoms. In another aspect, wherein $R_2$ and $R_3$ are each independently selected from unsaturated or saturated alkyl, unsaturated or saturated aralkyl, unsaturated or saturated heteroaralkyl, unsaturated or saturated alkoxyalkyl, unsaturated or saturated carboxyalkyl, unsaturated or saturated hydroxyalkyl, unsaturated or saturated hydroxyalkyl-polyoxyalkylene, wherein each group may be substituted or unsubstituted. In another aspect, wherein each of $R_2$ and $R_3$ group has from about 1 to 20 carbon atoms, such as from 1 to 10 carbon atoms, or from about 1 to 6 carbon atoms. In another aspect, wherein the alkyl of each $R_2$ and $R_3$ is independently selected from methyl and ethyl, the aralkyl is benzyl, the hydroxyalkyl is selected from hydroxyethyl and hydroxypropyl, and/or the carboxyalkyl is selected from acetate and propionate. In another aspect, wherein $R_4$ is an unsaturated or saturated hydrocarbyl group, such as an alkylene group optionally having a chain length of from about 1 to 4 carbon atoms. In another aspect, wherein $R_4$ is selected from methylene and ethylene. In another aspect, wherein the zwitterionic surfactant is selected from the group consisting of alkyl N,N-dimethyl betaines, alkyl N,N-diethyl betaines, alkyl N-ethyl, N-methyl betaines, the Stepan® Amphosol Series of surfactants, glycine betaine surfactants, and Zwittergent surfactants. In another aspect, wherein the zwitterionic surfactant is stearyl betaine. In another aspect, wherein the amphoteric surfactant is a compound of formula (II), (III), or (IV):

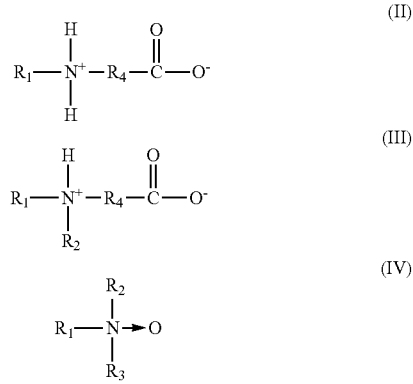

wherein:

$R_1$ represents a hydrophobic group, wherein the hydrophobic group comprises a substituted or unsubstituted hydrocarbon group, or a substituted or unsubstituted heterogeneous group;

$R_2$ and $R_3$ are each independently selected from hydrogen or a substituted or unsubstituted hydrocarbon group, or a substituted or unsubstituted heterogeneous group; and $R_4$ is a substituted or unsubstituted hydrocarbon group, or a substituted or unsubstituted heterogeneous group. In another aspect, wherein the amphoteric surfactant is selected from the group consisting of alkyl betaine, amino betaine, N-alkyl beta-alanine, amido betaine, imidazoline betaine, and amine oxides. In another aspect, wherein the amphoteric surfactant is myristyl dimethylamine oxide. In another aspect, wherein an amount of the first surfactant is from about 0.05 wt % to about 3 wt %, from about 0.1 wt % to about 3 wt %, from about 0.25 wt % to about 3 wt %, from about 0.5 wt % to about 3 wt %, from about 0.05 wt % to about 2 wt %, from about 0.1 wt % to about 2 wt %, from about 0-25 wt % to about 2 wt %, or from about 0.5 wt % to about 2 wt % based on the total weight of the mixture. In another aspect, wherein an amount of the second surfactant is from about 0.05 wt % to about 3 wt %, from about 0.1 wt % to about 3 wt %, from about 0.25 wt % to about 3 wt %, from about 0.5 wt % to about 3 wt %, from about 0.05 wt % to about 2 wt %, from about 0.1 wt % to about 2 wt %, from about 0.25 wt % to about 2 wt %, or from about 0.5 wt % to about 2 wt % based on the total weight of the mixture. In another aspect, wherein the ratio of the first surfactant to the second surfactant is from about 0.04:0.96 to about 0.96:0.04 (w/w), such as from about 0.10:0.90 to about 0.90:0.10 (w/w); from about 0.3:07 to about 07:0.3 (w/w); or from about 0.6:0.4 to about 0.4:0.6 (w/w) based on the total weight of surfactants. In another aspect, wherein the method is a single-pot reaction. In another aspect, wherein the at least one surfactant comprises at least one gemini surfactant. In another aspect, In another aspect, wherein the at least one gemini surfactant is a compound of the formula m-s-n, wherein m and n Independently represent a hydrocarbon tail and s is a spacer. In another aspect, wherein m and n are the same. In another aspect, wherein m and n are different. In another aspect, wherein m and/or n are saturated. In another aspect, wherein m and n are less than 20. In another aspect, wherein s is symmetric. In another aspect, wherein s is asymmetric. In another aspect, wherein s is saturated. In another aspect, wherein s is butylene. In another aspect, wherein the length of the metal nanorods is proportional to s. In another aspect, wherein the gemini surfactant is a compound of formula (V):

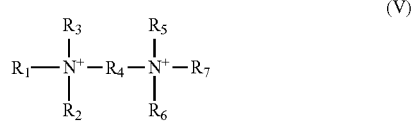

(V)

wherein:

$R_1$ and $R_7$ are each independently a hydrophobic group, wherein the hydrophobic group comprises a substituted or unsubstituted hydrocarbon group, or a substituted or unsubstituted heterogeneous group;

$R_2$, $R_3$, $R_5$ and $R_6$ are each independently selected from hydrogen or a substituted or unsubstituted hydrocarbon group, and a substituted or unsubstituted heterogeneous group; and $R_4$ is selected from a substituted or unsubstituted hydrocarbon group, and a substituted or unsubstituted heterogeneous group. In another aspect, wherein $R_1$ and $R_2$ are each independently selected from unsaturated or saturated alkyl, unsaturated or saturated aralkyl, unsaturated or saturated heteroaralkyl, unsaturated or saturated alkoxyalkyl, and unsaturated or saturated alkylamidoalkyl, wherein each group may be substituted or unsubstituted. In another aspect, wherein the alkyl of each $R_1$ and $R_7$ represents a group that contains from about 6 to 24 carbon atoms, such as about 12 to about 24 carbon atoms. In another aspect, wherein $R_2$, $R_3$, $R_5$, and $R_6$ are each independently selected from unsaturated or saturated alkyl, unsaturated or saturated aralkyl, unsaturated or saturated heteroaralkyl, unsaturated or saturated alkoxyalkyl, unsaturated or saturated carboxyalkyl, unsaturated or saturated hydroxyalkyl, unsaturated or saturated hydroxyalkyl-polyoxyalkylene, wherein each group may be substituted or unsubstituted. In another aspect, wherein each $R_2$, $R_3$, $R_5$, and $R_6$ group has from about 1 to 20 carbon atoms, such as from 1 to 10 carbon atoms, or from about 1 to 6 carbon atoms. In another aspect, wherein the alkyl of each $R_2$, $R_3$, $R_5$, and $R_6$ is independently selected from methyl and ethyl, the aralkyl is benzyl, the hydroxyalkyl is selected from hydroxyethyl and hydroxy propyl, and/or the carboxyalkyl is selected from acetate and propionate. In another aspect, wherein $R_4$ is an unsaturated or saturated hydrocarbyl group, such as an alkylene group optionally having a chain length of from about 1 to 12 carbon atoms. In another aspect, wherein $R_4$ is selected from methylene and ethylene. In another aspect, wherein the at least one gemini surfactant is selected from N,N'-dialkyl-N,N,N',N'-tetraalkylalkylene-α,ω-diaminium dibromides. In another aspect, wherein the at least one gemini surfactant is selected from N,N'-didodecyl-N,N,N',N'-tetramethylbutane-M-di-aminium dibromide (12-4-12), N,N'-didodecyl-N,N,N',N'-tetramethylbutane-1,4-diaminium dibromide (12-4-12) N,N'-didodecyl-N,N,N',N'-tetramethylhexane-1,6-di-aminium dibromide (12-6-12), N,N'-ditetradecyl-N,N,N',N'-tetramethylhexane-1,6-diaminium dibromide (14-6-14), N,N'-dihexadecyl-N,N,N',N'-tetramethylbutane-1,4-di-aminium dibromide (16-4-16), and N,N'-hexadecyl-N,N,N',N'-tetramethyloctane-1,8-diaminium dibromide (16-8-16). In another aspect, wherein the at least one gemini surfactant is N,N'-ditetradecyl-N,N,N',N'-tetramethylhexane-1,6-di-aminium dibromide (14-6-14). In another aspect, wherein an amount of the gemini surfactant is from about 0.5 wt % to about 3 wt %, or from about 0.75 wt % to about 2 wt %. In another aspect, wherein the metal cations are selected from transition metal cations and combinations thereof. In another aspect, wherein the transition metal cations are selected from precious metal cations and combinations thereof. In another aspect, wherein the metal cations are selected from the group consisting of gold, nickel, palladium-, platinum, copper, silver, zinc, cadmium, and combinations thereof. In another aspect, wherein the metal cations are gold (I) or gold (III). In another aspect, wherein the metal cations are gold (III). In another aspect, wherein the source of metal cations comprises at least one metal salt. In another aspect, wherein the metal salt is selected from the group consisting of gold (III) chloride, gold sodium thiomalate, gold sodium thiosulfate, triethylphosphine gold, gold sodium thioglucose, gold (III) bromide, gold (III) iodide, gold (III) nitrate. In another aspect, wherein the metal salt is gold (III) chloride. In another aspect, wherein an amount of the source of metal cations is from about 0.004 wt % to about 0.04 wt % based on the total weight of the mixture, from about 0.005 wt % to about 0.03 wt %, or from about 0.007 wt % to 0.02 wt %. In another aspect, wherein the metal nanorods comprise an alloy or composite metal. In another aspect, further comprising adding metal seeds. In another aspect, wherein the method does not use metal seeds. In another aspect, wherein the metal seeds comprise gold seeds. In another aspect, wherein the method is cytotoxic surfactant-free. In another aspect, wherein the method is cytotoxic cationic surfactant-free. In another aspect, wherein the method is CTAB-free. In another aspect, wherein the method is polymeric stabilizer-free. In another aspect, wherein all components of the mixture are pharmaceutically acceptable and/or non-toxic. In another aspect, wherein the mixture has a pH of about 4 to about 9. In another aspect, wherein combining further comprises combining a solvent with the source of metal cations and the at least one surfactant. In another aspect, wherein the solvent is selected from the group consisting of water, low molecular weight alcohols, hydrocarbons, or mixtures thereof. In another aspect, wherein the solvent is water. In another aspect, wherein water is triply deionized water. In another aspect, wherein water lacks conductivity. In another aspect, wherein water substantially lacks conductivity. In another aspect, wherein the metal nanorods are produced in an amount of at least one gram. In another aspect, wherein the metal nanorods produced by the method have a diameter of between about 5 nm and about 50 nm. In another aspect, wherein the diameter is from about 5 nm to about 30 nm. In another aspect, wherein the diameter is from about 15 nm to about 30 nm. In another aspect, wherein the metal nanorods produced by the method have an axial length of between about 20 nm and about 500 nm. In another aspect, wherein the axial length is from about 30 nm to about 500 nm. In another aspect, wherein the axial length is from about 50 nm to about 300 nm. In another aspect, wherein the axial length is from about 80 nm to about 100 nm. In another aspect, wherein the metal nanorods produced by the method have an aspect ratio of from about 1.1 to about 100 or from about 1.1 to about 91. In another aspect, wherein the metal nanorods produced by the method are substantially uniform in length, diameter, and/or aspect ratio, in another aspect, wherein the metal nanorods are at least about 95% metal, at least about 96% metal, at least about 97% metal, at least about 98% metal, at least about 99% metal, at least about 99.9% metal, or at least about 99.99% metal. In another aspect, wherein the metal is gold. In another aspect, further comprising applying a targeting moiety to the metal nanorods. In another aspect, wherein the targeting moiety is a protein. In another aspect, wherein the targeting moiety is tumour-specific. In another aspect, wherein the time sufficient to produce the metal nanorods is from about 10 minutes to about 24 hours. In another aspect, wherein the metal nanorods produced by the method are substantially uniform in size and/or shape.

In yet another aspect, there is provided a method for making metal nanorods, the method comprising: combining metal seeds with a growth solution comprising at least one gemini surfactant and a source of metal cations to form a mixture, wherein the metal cations are reduced and the metal nanorods are produced.

With respect to the methods described herein, aspects are provided as follows in any suitable permutations: In another aspect, wherein the at least one gemini surfactant reduces the metal cations. In another aspect, wherein combining further comprises at least one reducing agent for reducing the metal cations. In another aspect, wherein an amount of the reducing agent is from about 0.001 wt % to about 0.002 wt %, from about 0.001 wt % to about 0.0018 wt %, or from about 0.0013 wt % to 0.0017 wt % based on the total weight of the mixture. In another aspect, wherein the reducing agent is selected from the group consisting of ascorbic acid, glucose, glucosamine, hydroquinone, aluminum, calcium, hydrogen, manganese, potassium, sodium borohydride, sodium triacetoxyborohydride, compounds containing the $Sn^{2+}$ ion, such as tin(II) chloride, sulfite compounds, hydrazine, zinc-mercury amalgam, diisobutylaluminum hydride, oxalic acid, formic acid, phosphites, hypophosphites, phosphorous acid, dithiothreitol (DTT), compounds containing the $Fe^{2+}$ ion, such as iron(II) sulfate, carbon monoxide, carbon, tris(2-carboxyethyl)phosphine HCl, and combinations thereof. In another aspect, wherein the at least one reducing agent comprises ascorbic acid and/or $NaBH_4$. In another aspect, wherein the mixture is maintained at any suitable temperature that promotes the formation of metal nanorods. In another aspect, wherein the mixture is maintained for any suitable time period that promotes the formation of metal nanorods. In another aspect, wherein the temperature is maintained at about 20° C. to about 35° C. In another aspect, wherein the time period is from about minutes to about 24 hours. In another aspect, further comprising, prior to the combining step, forming the metal seeds by reducing metal cations in a seed solution comprising at least one gemini surfactant and a source of the metal cations. In another aspect, wherein the ratio of the seed solution amount to the growth solution amount is from about 0.005:0.995 to about 0.05:0.95 (w/w), 0.006:0.994 to about 0.05:0.95 (w/w), from about 0.008:0.992 to about 0.05:0.95 (w/w); from about 0.01:0.99 to about 0.05:0.95 (w/w), from about 0.005:0.995 to about 0.01:0.99 (w/w), from about 0.005:0.995 to about 0.009:0.991 (w/w); from about 0.005:0.995 to about 0.008:0.992 (w/w); or from about 0.005:0.995 to about 0.007:0.993 (w/w) based on the total weight of seed and growth solutions. In another aspect, wherein the at least one gemini surfactant in the seed solution and the at least one gemini surfactant in the growth solution are the same or different. In another aspect, wherein the source of metal cations in the seed solution and the source of metal cations in the growth solution are the same or different. In another aspect, wherein the seed solution further comprises a reducing agent. In another aspect, wherein the reducing agent of the seed solution comprises ascorbic acid and/or $NaBH_4$. In another aspect, wherein the metal cations are reduced with $NaBH_4$ and residual $NaBH_4$ in the seed solution reduces the metal cations in the growth solution. In another aspect, wherein the at least one gemini surfactant creates wormlike micelles. In another aspect, wherein the at least one gemini surfactant is a compound of the formula m-s-n, wherein m and n independently represent a hydrocarbon tail and s is a spacer. In another aspect, wherein m and n are the same. In another aspect, wherein m and n are different. In another aspect, wherein m and/or n are saturated. In another aspect, wherein m and n are less than 20. In another aspect, wherein s is symmetric. In another aspect, wherein s is asymmetric. In another aspect, wherein s is saturated. In another aspect, wherein s is butylene. In another aspect, wherein the length of the metal nanorods is proportional to s. In another aspect, wherein the at least one gemini surfactant is a compound of formula (V):

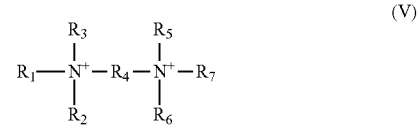

wherein:

$R_1$ and $R_7$ are each independently a hydrophobic group, wherein the hydrophobic group comprises a substituted or unsubstituted hydrocarbon group, or a substituted or unsubstituted heterogeneous group;

$R_2$, $R_3$, $R_5$ and $R_6$ are each independently selected from hydrogen or a substituted or unsubstituted hydrocarbon group, and a substituted or unsubstituted heterogeneous group; and $R_4$ is selected from a substituted or unsubstituted hydrocarbon group, and a substituted or unsubstituted heterogeneous group. In another aspect, wherein $R_1$ and $R_7$ are each independently selected from unsaturated or saturated alkyl, unsaturated or saturated aralkyl, unsaturated or saturated heteroaralkyl, unsaturated or saturated alkoxyalkyl, and unsaturated or saturated alkylamidoalkyl, wherein each group may be substituted or unsubstituted. In another aspect, wherein the alkyl of each $R_1$ and $R_7$ represents a group that contains from about 6 to 24 carbon atoms, such as from about 12 to about 24 carbon atoms. In another aspect, wherein $R_2$, $R_3$, $R_4$, and $R_5$ are each independently selected from unsaturated or saturated alkyl, unsaturated or saturated aralkyl, unsaturated or saturated heteroaralkyl, unsaturated or saturated alkoxyalkyl, unsaturated or saturated carboxyalkyl, unsaturated or saturated hydroxyalkyl, unsaturated or saturated hydroxyalkyl-polyoxyalkylene, wherein each group may be substituted or unsubstituted. In another aspect, wherein each $R_2$, $R_3$, $R_5$, and $R_6$ group has from about 1 to 20 carbon atoms, such as from 1 to 10 carbon atoms, or from about 1 to 6 carbon atoms. In another aspect, wherein the alkyl of each $R_2$, $R_3$, $R_5$, and $R_6$ is independently selected from methyl and ethyl, the aralkyl is benzyl, the hydroxyalkyl is selected from hydroxyethyl and hydroxy propyl, and/or the carboxyalkyl is selected from acetate and propionate. In another aspect, wherein $R_4$ is an unsaturated or saturated hydrocarbyl group, such as an alkylene group optionally having a chain length of from about 1 to 12 carbon atoms. In another aspect, wherein $R_4$ is selected from methylene and ethylene. In another aspect, wherein the at least one gemini surfactant is selected from N,N'-dialkyl-N,N,N',N'-tetraalkylalkylene-α,ω-diaminium dibromides. In another aspect, wherein the at least one gemini surfactant is selected from N,N'-didodecyl-N,N,N',N'-tetramethylbutane-1,4-diaminium dibromide (12-4-12), N,N'-didodecyl-N,N,N',N'-tetramethylbutane-1,4-diaminium dibromide (12-4-12) N,N'-didodecyl-N,N,N',N'-tetramethylhexane-1,6-diaminium dibromide (12-6-12), N,N'-ditetradecyl-N,N,N',N'-tetramethylhexane-1,6-diaminium dibromide (14-6-14), N,N'-dihexadecyl-N,N,N',N'-tetramethylbutane-1,4-diaminium dibromide (16-4-16), and N,N'-hexadecyl-N,N,N',N'-tetramethyloctane-1,8-diaminium dibromide (16-8-16). In another aspect, wherein the at least one gemini surfactant is N,N'-ditetradecyl-N,N,N',N'-tetramethylhexane-1,6-diaminium dibromide (14-6-14). In another aspect, wherein the amount of at least one gemini surfactant is from about 0.05 wt % to about 5 wt %, from about 0.5 wt % to about 3 wt %, or from about 0.75 wt % to about 2 wt %. In another aspect, wherein the metal cations are selected from transition metal cations and combinations thereof. In another aspect, wherein the transition metal cations are selected from precious metal cations and combinations thereof. In another aspect, wherein the metal cations are selected from the group consisting of gold, nickel, palladium, platinum, copper, silver, zinc, cadmium, and combinations thereof, in another aspect, wherein the metal cations are gold (I) or gold (III). In another aspect, wherein the metal cations are gold (III). In another aspect, wherein the source of metal ions comprises a metal salt. In another aspect, wherein the metal salt is selected from the group consisting of gold (III) chloride, gold sodium thiomalate, gold sodium thiosulfate, triethylphosphine gold, gold sodium thioglucose, gold (III) bromide, gold (III) iodide, gold (III) nitrate. In another aspect, wherein the metal salt is gold (III) chloride. In another aspect, wherein the metal nanorods comprise an alloy or composite metal. In another aspect, wherein the method is cationic surfactant-free. In another aspect, wherein the method is cytotoxic surfactant-free. In another aspect, wherein the method is cytotoxic cationic surfactant-free. In another aspect, wherein the method is CTAB-free. In another aspect, wherein the method is polymeric stabilizer-free. In another aspect, wherein all components of the mixture are pharmaceutically acceptable and/or non-toxic.

In another aspect, wherein the mixture has a pH of about 4 to about 9. In another aspect, wherein combining further comprises combining a solvent with the source of metal cations and the at least one surfactant. In another aspect, wherein the solvent is selected from the group consisting of water, low molecular weight alcohols, hydrocarbons, or mixtures thereof. In another aspect, wherein the solvent is water. In another aspect, wherein water is triply deionized water. In another aspect, wherein water lacks conductivity. In another aspect, wherein water substantially lacks conductivity. In another aspect, wherein the metal nanorods are produced in an amount of at least one gram. In another aspect, wherein the metal nanorods produced by the method have a diameter of between about 5 nm and about 50 nm. In another aspect, wherein the diameter is from about 5 nm to about 30 nm. In another aspect, wherein the diameter is from about 15 nm to about 30 nm. In another aspect, wherein the metal nanorods produced by the method have an axial length of between about 20 nm and about 500 nm. In another aspect, wherein the axial length is from about 30 nm to about 500 nm. In another aspect, wherein the axial length is from about 50 nm to about 300 nm. In another aspect, wherein the axial length is from about 80 nm to about 100 nm. In another aspect, wherein the metal nanorods produced by the method have an aspect ratio of from about 1.1 to about 100 or from about 1.1 to about 10. In another aspect, wherein the metal nanorods produced by the method are substantially uniform in length, diameter, and/or aspect ratio. In another aspect, further comprising applying a targeting moiety to the metal nanorods. In another aspect, wherein the targeting moiety is a protein. In another aspect, wherein the targeting moiety is tumour-specific. In another aspect, wherein the time sufficient to produce the metal nanorods is from about 10 minutes to about 24 hours. In another aspect, wherein the solution of nanorods produced are produced at a temperature of about 15° C. to 35° C., about 20° C. to 30° C., about 25° C. to 28° C., or at about 27° C. In another aspect, wherein the metal nanorods produced by the method are substantially uniform in size and/or shape.

With respect to additional treatments/purification/stability with respect to the nanorods produced from the methods described herein or nanorods produced by other methods, aspects are provided as follows in any suitable permutations: In another aspect, wherein the method further comprises heating the metal nanorod solution to a suitable temperature to adjust at least one of length and/or shape. In another aspect, wherein the temperature is from about 30° C. to about 89° C. and in pH ranges from about 4 to about 9. In another aspect, wherein the method further comprises adding a co-surfactant, a co-solvent, or an oxidizing agent. In another aspect, wherein the method further comprises centrifugation to remove impurities, in another aspect, further comprises a method of purifying the metal nanorods from a metal nanorod solution comprising: combining the metal nanorod solution with a gemini surfactant and a salt, wherein the gemini surfactant and the salt form a coacervate; and separating the coacervate, wherein the coacervate contains the metal nanorods. In another aspect, the method further comprises adding a metal salt and a phase separating surfactant for separating metal nanorods into a surfactant-rich phase of the phase separating surfactant-containing layer. In another aspect, wherein the metal salt is selected from alkali metal salts, alkaline earth metal salts, transition metal salts, or combinations thereof. In another aspect, wherein the metal salt is an alkali metal salt. In another aspect, wherein the alkali metal salt is sodium chloride. In another aspect, wherein the method further comprises centrifuging the metal nanorod solution to form a metal nanorod pellet and a solvent layer, separating the solvent layer from the metal nanorod pellet, adding water, and centrifuging. In another aspect, wherein the method further comprises adding at least one solubilizate to a metal nanorod solution comprising the metal nanorods. In another aspect, wherein the at least one solubilizate is a biomolecule. In another aspect, wherein the biomolecule is selected from proteins, nucleic acids, polysaccharides, glycoproteins, flavonoids, vitamins, antioxidants, aromatic acids, amino acids, monohydroxybenzoic acid, monosaccharides, disaccharides, bile salt, nucleotides, or combinations thereof. In another aspect, wherein the at least one solubilizate is selected from gelatin, beta casein, streptavidin, metal nanorod-streptavidin conjugate, bovine serum albumin, quercetin, epigallocatechin gallat, curcumin, curcumin, glutathione, oxy/deoxy cholic acid, anthranilic add, cinnamic acid, biotin, p-hydroxybenzoic acid, or combinations thereof. In another aspect, wherein the at least one solubilizate is adsorbed on a surfactant bilayer of the metal nanorods. In another aspect, wherein an amount of the at least one solubilizate is from about 0.03% to about 20% (w/w); about 0.1% to about 20% (w/w); about 0.03% to about 10% (w/w); about 0.03% to about 5% (w/w); about 0.1% to about 15% (w/w); or about 0.1% to about 10% (w/w) based on total weight of the metal nanorod solution. In another aspect, wherein the metal nanorods have a surfactant bilayer wrapped in a polymer. In another aspect, wherein the polymer is selected from proteins, gelatin, bovine serum albumin, polystyrene sulfonate, polyethylene oxides, thiolated polyethylene oxides, thiolated polyethylene oxides with terminating carboxylic acid functionalities, thiolated polyethylene oxides with terminating amine acid functionalities, or combinations thereof. In another aspect, wherein the polymer forms covalent or non-covalent bonds with at least one of a protein, a polypeptide, an antibody, an antibody fragment, an IgG class of antibody, a polyclonal antibody, a monoclonal antibody, or combinations thereof. In another aspect, wherein the metal nanorods further comprise a capping agent. In another aspect, wherein a solvent or excess surfactant is removed from the metal nanorod solution followed by addition of an aqueous solution of the capping agent. In another aspect, wherein the method further comprises removal of greater than about 95% of solvent from the metal nanorod solution, followed by the addition of a first capping agent, and removing of greater than about 95% of resultant solvent from resultant metal nanorod pellets. In another aspect, wherein the removing comprises centrifugation. In another aspect, further comprising dispersing the resultant metal nanorod pellets into an aqueous solution of a second capping agent. In another aspect, the first and second capping agents may be the same or different. In another aspect, wherein the metal nanorods are positively charged and have a charge of from about +5 to about +40 mV or the metal nanorods are negatively charged and have a charge of from about −5 to about −55 mV. In another aspect, wherein the capping agent is a mixture of surfactant and a thiolated polymer. In another aspect, wherein the capping agent is a mixture of surfactant, a co-surfactant, and small biomolecules, wherein the small biomolecules are selected from a general class of flavonoids, antioxidants, aromatic adds, amino acids, monohydroxybenzoic acid, monosaccharides, disaccharides, bile salt, nucleotides, or combinations thereof. In another aspect, wherein the method further comprises a co-capping agent selected from quercetin, epigallocatechin gallate, curcumin, glutathione, ascorbic acid, citric acid, anthranilic acid, cinnamic acid, bile acid, p-hydroxybenzoic acid, metal anionic salts of biological acid(s), or combinations thereof. In another aspect, wherein the method further comprises extracting the metal nanorods and re-dispersing the metal nanorods in a surfactant composition comprising a stabilizing agent. In another aspect, wherein extracting comprises centrifuging followed by re-dispersion into the surfactant composition with a pH adjuster. In another aspect, wherein the stabilizing agent comprises at least one surfactant that has less carbon atoms than the at least one surfactant used to make the metal nanorods. In another aspect, wherein the stabilizing agent comprises at least one alkyl glycine surfactant and at least one alkyl N-oxide surfactant. In another aspect, wherein at least one alkyl N-oxide surfactant is selected from any suitable amphoteric N-oxide surfactant.

With respect to the methods described herein, in another aspect, wherein at least about 40% of the source of metal cations is reduced to nanoparticles; at least about 50% is reduced to nanoparticles; at least about 60% is reduced to nanoparticles; at least about 70% is reduced to nanoparticles; at least about 80% is reduced to nanoparticles; at least about 90% is reduced to nanoparticles; or at least about 99% is reduced to nanoparticles.

In another aspect, there is provided metal nanorods produced by the method described herein.

In another aspect, there is provided metal nanorods free of a cytotoxic surfactant. In another aspect, the metal nanorods are free of a cationic cytotoxic surfactant. In another aspect, the metal nanorods are free of CTAB. In another aspect, the metal nanorods are produced using a composition free of metal seeds. In another aspect, the metal nanorods are free of a polymeric stabilizer.

In another aspect, there is provided metal nanorods produced using a composition free of metal seeds.

In another aspect, there is provided metal nanorods free of a polymeric stabilizer.

In another aspect, there is provided the metal nanorods described herein, produced by the method described herein.

In another aspect, there is provided a composition comprising the metal nanorods described herein. In another aspect, wherein the metal nanorods are essentially pure. In another aspect, wherein the composition is stable.

In another aspect, there is provided a device comprising the metal nanorods described herein or the composition described herein. In another aspect, wherein the device is a lateral flow assay device. In another aspect, wherein the device is a lateral flow strip immune assay device or vertical flew immune assay device. In another aspect, wherein the metal nanorod comprises a metal nanorod and an antibody conjugate. In another aspect, wherein the metal nanorod and antibody conjugate is capable of capturing a bio-marker from a test solution.

In another aspect, there is provided a method of treating cancer, the method comprising administering a treatment effective amount of the metal nanorods described herein to a subject and applying infrared light to heat the metal nanorods.

In another aspect, there is provided a method of imaging a tumour, the method comprising administering an imaging effective amount of the metal nanorods described herein to a subject and imaging the tumour, wherein the metal nanorods provide contrast to the image.

In another aspect, there is provided a method of diagnosing cancer, the method comprising administering a diagnostic amount of the metal nanorods described herein to a subject and imaging the subject, wherein contrast provided by the metal nanorods is evidence of a cancer.

In another aspect, there is provided a use of a treatment effective amount of the metal nanorods described herein in combination with infrared light for treating cancer.

In another aspect, there is provided a use of an imaging effective amount of the metal nanorods described herein for imaging a tumour.

In another aspect, there is provided a use of a diagnostic amount of the metal nanorods described herein for imaging and thereby diagnosing a cancer.

In another aspect, there is provided a method for controlling the size and/or aspect ratio of metal nanorods in a seed-growth method, the method comprising combining a gemini surfactant with metal seeds and a source of metal cations.

In another aspect, there is provided a use of a gemini surfactant for controlling the size and/or aspect ratio of metal nanorods.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

BRIEF DESCRIPTION OF THE DRAWINGS

The present invention will be further understood from the following description with reference to the Figures, in which.

DETAILED DESCRIPTION OF CERTAIN EMBODIMENTS

Figure 1:
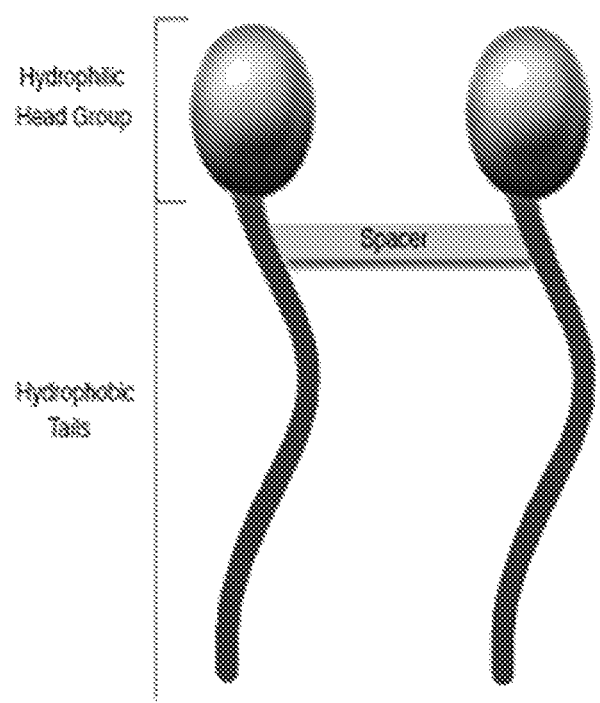
FIG. 1 shows the general structure of a gemini surfactant.

Described herein are methods of making metal nanoparticles, such as nanorods, using surfactant compositions. Metal nanorods and compositions and uses thereof are also described. In typical embodiments, the methods, nanorods, and compositions described herein involve the use of at least one surfactant that directs metal nanorod formation. In embodiments, the at least one surfactant is used in place of the cytotoxic CTAB surfactant that is used in most conventional commercial preparations of gold nanorods.

Metal nanorods, such as gold nanorods, are useful in medicine for many purposes, such as imaging, diagnostics, and treatment of cancer. Gold nano rods have special optical properties, in that they can absorb light in the infra-red region of about 700 to about 900 nm and can be easily detected when a laser beam with a similar wavelength (approximately 800 nm) is shone upon them. Laser light at this wavelength is safe for biological tissue, which is transparent to such light, meaning that the tissue does not absorb the light. As a result, gold nanorods can be injected directly into a blood-stream and their location/distribution can be determined using a safe laser light, also referred to as infrared irradiation.

In addition, metal nanorods, such as gold nanorods, can heat up when laser light is shone on them. This property results in their ability to increase the temperature locally, for example in the immediate vicinity of a specific target. If that target is a tumour or an individual cancer cell, the tumour or cell will be damaged or destroyed when the laser light is used. This allows for non-invasive anti-cancer therapy, or photo-thermal therapy, using metal nanorods. Furthermore, photo-thermal therapy can be selective when the metal nanorods are coated with specific proteins. Such proteins can deliver metal nanorods primarily to the tumours. Even without specific targeting proteins, however, metal nanorods have a proven tendency to accumulate in solid tumours because of the fenestrations in the blood vessels that feed solid tumours, which tend to be about 5 to about 10 times greater in size than the size of the metal nanorods described herein. In contrast, such large fenestrations tend to be absent from normal vasculature. Accordingly, the metal nanorods described herein have the ability to penetrate through these tumour-associated fenestrations, leave the blood stream and accumulate in the tumour. An infra-red light can then be used to heat up the metal nanorods and treat the tumour.

In embodiments, the metal nanorods described herein are capable of producing many colours. Specifically, the nanorods may be red, blue, green, purple, or brown. Therefore, the metal nanorods may be used as a colour indicator in paper and membrane-based point of care devices.

Metal nanorods also have many applications in nanotechnology. They have been used for the preparation of metamaterials and find use in anti-reflecting coatings, for example.

Definitions

The following definitions are used herein and should be referred to for interpretation of the claims and the specification:

As used herein, the term "nanorod" denotes a substantially cylindrical and/or polygonal shape being either solid or hollow. In embodiments, at least a portion of the surface of the nanorod may be substantially smooth and/or at least a portion of the surface may be etched (e.g. symmetrically etched and/or asymmetrically etched; typically, symmetrically etched) In certain embodiments, the nanorod may be symmetrically etched to provide a multi-harmonic shape (e.g. appears as wave in 2-D). Typically the nanorod has a diameter or cross-section of between about 5 nm and about 50 nm, such as from about 5 nm, about 10 nm, about 15 nm, about 20 nm, about 25 nm, about 30 nm, about 35 nm, about 40 nm, or about 45 nm, to about 10 nm, about 15 nm, about 20 nm, about 25 nm, about 30 nm, about 35 nm, about 40 nm, about 45 nm, or about 50 nm. For example, the diameter may be from about 5 nm to about 30 nm or from about 15 nm to about 30 nm.

The nanorods may typically have an axial length of between about 20 nm and about 500 nm, such as from about 20 nm, about 30 nm, about 40 nm, about 50 nm, about 60 nm, about 70 nm, about 80 nm, about 90 nm, about 100 nm, about 125 nm, about 150 nm, about 175 nm, about 200 nm, about 250 nm, about 300 nm, about 350 nm, about 400 nm, or about 450 nm, to about 30 nm, about 40 nm, about 50 nm, about 60 nm, about 70 nm, about 80 nm, about 90 nm, about 100 nm, about 125 nm, about 150 nm, about 175 nm, about 200 nm, about 250 nm, about 300 nm, about 350 nm, about 400 nm, about 450 nm, or about 500 nm. For example, the axial length may be from about 30 nm to about 500 nm, from about 50 nm to about 300 nm, or from about 80 nm to about 100 nm.

Furthermore, the nanorods may typically have an aspect ratio (i.e., the ratio of the length of the major axis of the nanorod to the minor axis of the nanorod) Of from about 1.1 to about 100, such as from about 1.1, about 1.2, about 1.3, about 1.4, about 1.5, about 1.6, about 1.7, about 1.8, about 1.9, about 2, about 3, about 4, about 5, about 6, about 7, about 8, about 9, about 10, about 20, about 30, about 40, about 50, about 60, about 70, about 80, or about 90, to about 1.2, about 1.3, about 1.4, about 1.5, about 1.6, about 1.7, about 1.8, about 1.9, about 2, about 3, about 4, about 5, about 6, about 7, about 8, about 9, about 10, about 20, about 30, about 40, about 50, about 60, about 70, about 80, about 90, or about 100. For example, the aspect ratio may be from about 1.1 to about 10.

The nanorods described herein are typically metal and, in embodiments, are selected from transition metals or precious metals and are typically selected from gold, nickel, palladium, platinum, copper, silver, zinc, cadmium, and combinations thereof. The methods, compositions, and nano rods described herein have been exemplified with respect to gold as the metal and source of cations, however. It will be understood that the methods are equally applicable to nanorods of other metals, particularly those listed above. The metal nanorods may comprise a single metal or may be an alloy (i.e., a solution mixture) or a composite (i.e., non-solution mixture) comprising one, two, three or more additional metals (for example, both gold and silver) (see, Sun, Y. "*Silver Nanowires—Unique Templates For Functional Nanostructures,*" Nanoscale 2:1626-1642; Wang, H. et al. (2009) "*Nucleic Acid Conjugated Nanomaterials for Enhanced Molecular Recognition,*" ACS Nano 3(9):2451-2460). In addition, metal oxide nanorods may also be formed, including titanium oxides, cerium oxides, and other ceramics.

A "metal nanorod pellet" refers to a precipitate of metal nanorods. "Pellet" is a term used to describe the precipitate that may be produced upon centrifugation.

A "source of metal cations" refers to positively charged metal ions. If the metal is gold, the metal cations could be gold (I), gold (II), gold (III), gold (IV), and/or gold (V) and, typically, gold (I) or gold (III), more typically gold (III). The source of the metal cations is typically a metal salt. For example, a source of silver cations includes an inorganic silver salt or an organic silver salt such as, but not limited to, silver acetate, silver chloride, silver perchlorate, silver chlorate, silver bromide, silver fluoride, silver lactate, silver nitrate, silver sulfate, silver tartrate, or combinations thereof. A source of gold cations includes an inorganic gold salt or an organic gold salt or a mixed gold salt such as, but not limited to, gold (III) chloride, gold sodium thiomalate, gold sodium thiosulfate, triethylphosphine gold, gold sodium thioglucose, gold (III) bromide, gold (III) iodide, gold (III) nitrate, and combinations thereof. Typically, the source of gold cations is gold (III) chloride. Other suitable sources of metal cations would be well known to the skilled person.

The term "surfactant" is short for surface active agent. Surfactants are amphiphilic compounds, meaning they contain two or more groups that, in their pure form, are insoluble in each other. Surfactants typically have at least one hydrophobic tail and at least one hydrophilic head and, more typically, surfactants have a single hydrophobic tail and a single hydrophilic head. Surfactants typically act to lower surface tension and can provide wetting, emulsification, foam, and detergency, in typical embodiments, the surfactants described herein comprise at least one positively charged moiety and at least one negatively charged moiety and may be classified as zwitterionic surfactants and/or amphoteric surfactants. The at least one positively charged moiety may have at least one permanently positively charged moiety at any pH and/or may have at least one moiety that is positively charged at a predetermined pH or a predetermined pH range. The at least one negatively charged moiety may have at least one moiety that is negatively charged at a predetermined pH or a predetermined pH range. It will be understood that, at a certain pH or pH range, many zwitterionic surfactants and amphoteric surfactants will be neutral in charge; it is also understood that in certain pH ranges, amphoteric surfactants become zwitterionic in nature.

A "zwitterionic surfactant" is a type of surfactant that possesses both positive and negative charges and typically has a broad isoelectric range. Typically, zwitterionic surfactants possess a first moiety that is permanently positively charged and a second moiety that is negatively charged over a broad pH range, such as from about 1 to about 14, or from about 1, about 2, about 3, about 4, about 5, about 6, about 7, about 8, or about 9 to about 4, about 5, about 6, about 7, about 8, about 9, about 10, about 11, about 12, about 13, or about 14, such as, for example, from about 2 to about 14.

Any suitable zwitterionic surfactant(s) may be used in the compositions and methods described herein. Examples include surfactants having various substituted or unsubstituted hydrocarbyl chains or substituted or unsubstituted heterogeneous chains, for example, substituted or unsubstituted hydrocarbyl chain lengths, such as about $C_8$ to $C_{22}$, about $C_{10}$ to $C_{18}$, and more typically, $C_{14}$ to $C_{18}$. Typical chains are alkyl, alkoxyalkyl, alkylaryl, or alkylamidoalkyl. The cation of the zwitterionic surfactant is typically ammonium, substituted ammonium such as alkyl substituted ammonium, and quaternary ammonium. The anion of the zwitterionic surfactant is typically, carboxylate, sulfate or sulfonate.

Further examples of zwitterionic surfactants contemplated herein are represented by formula (I):

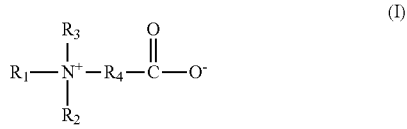

wherein:

$R_1$ represents a hydrophobic group, wherein the hydrophobic group comprises a substituted or unsubstituted hydrocarbon group, or a substituted or unsubstituted heterogeneous group;

$R_2$ and $R_3$ are each independently selected from hydrogen a substituted or unsubstituted hydrocarbon group, or a substituted or unsubstituted heterogeneous group; and $R_4$ is a substituted or unsubstituted hydrocarbon group, or a substituted or unsubstituted heterogeneous group.

In more typical embodiments, $R_1$ represents a hydrophobic group, wherein the group is selected from unsaturated or saturated alkyl, unsaturated or saturated aralkyl, unsaturated or saturated heteroaralkyl, unsaturated or saturated alkoxyalkyl, and unsaturated or saturated alkylamidoalkyl, wherein each group may be substituted or unsubstituted. In further embodiments, the alkyl represents a group that contains from about 12 to 24 carbon atoms.

In more typical embodiments, $R_2$ and $R_3$ are each independently selected from unsaturated or saturated alkyl, unsaturated or saturated aralkyl, unsaturated or saturated heteroaralkyl, unsaturated or saturated alkoxyalkyl, unsaturated or saturated carboxyalkyl, unsaturated or saturated hydroxyalkyl, unsaturated or saturated hydroxyalkyl-polyoxyalkylene, wherein each group may be substituted or unsubstituted. In further embodiments, each group has from about 1 to 20 carbon atoms, more typically 1 to 10 carbon atoms, and most typically from about 1 to 6 carbon atoms. Typical, alkyl groups include methyl and ethyl, typical aralkyl groups include benzyl, typical hydroxyalkyl groups include hydroxyethyl and hydroxypropyl, and typical carboxyalkyl groups include acetate and propionate.

In another embodiment, $R_4$ is an unsaturated or saturated hydrocarbyl group. Typically, the hydrocarbyl group is an alkylene group. More typically, the alkylene group has a chain length of about 1 to 4 carbon atoms. Typically, the group includes methylene and ethylene groups.

Some specific examples of zwitterionic surfactants include, without being limited thereto, alkyl N,N-dimethyl betaines, alkyl N,N-diethyl betaines, alkyl N-ethyl, N-methyl betaines. Other zwitterionic surfactant(s) include, but are not limited to, betaine-type surfactants such as the Stepan® Amphosol Series of surfactants (Amphosol HCA and Amphosol HCG), glycine betaine surfactants such as dodecyl glycine betaine (EBB), and surfactants of Zwittergent family (ammonio propane sulfonate zwitterionic surfactants), in a typical embodiment, the zwitterionic surfactant is stearyl betaine.

In an embodiment, the zwitterionic surfactant is chosen so that the resultant surfactant composition does not substantially interfere with the reduction of the metal cations to metal.

An "amphoteric surfactant" is a type of surfactant that possesses both positive and/or negative charges or is neutral, depending upon pH and typically has a narrow isoelectric range. Typically, amphoteric surfactants possess first and second moieties. Over a first predetermined pH range, which is typically slightly acidic (for example, from about 4 to about 7, such as from about 4, about 5, or about 6 to about 5, about 6, or about 7), the first moiety is positively charged and the second moiety is negatively charged.

Over a second predetermined pH range, which is typically slightly alkaline (for example, from about 7 to about 12, such as from about 7, about 8, about 9, about 10, or about 11 to about 8, about 9, about 10, about 11, or about 12), the first moiety is not charged and the second moiety is negatively charged.

Finally, over a third predetermined pH range, which is typically moderately acidic (for example, from about 2 to about 6, such as from about 2, about 3, about 4, or about 5, to about 3, about 4, about 5, or about 6), the first moiety is positively charged and the second moiety is not charged.

Any suitable amphoteric surfactant(s) may be used in the compositions and methods described herein. Examples include surfactants having various substituted or unsubstituted hydrocarbyl chains or substituted or unsubstituted heterogeneous chains, for example, substituted or unsubstituted hydrocarbyl chain lengths, such as about $C_8$ to $C_{22}$, about $C_{10}$ to $C_{18}$, and more typically, $C_{12}$ to $C_{16}$. Typical chains are alkyl, alkoxyalkyl, aralkyl, heteroalkyl, or alkylamidoalkyl. The cation of the amphoteric surfactant is typically a secondary or tertiary ammonium group. The anion of the amphoteric surfactant is typically, carboxylate, sulfate or sulfonate.

Further examples of amphoteric surfactants contemplated herein are represented by formulas (II), (III), and (IV):

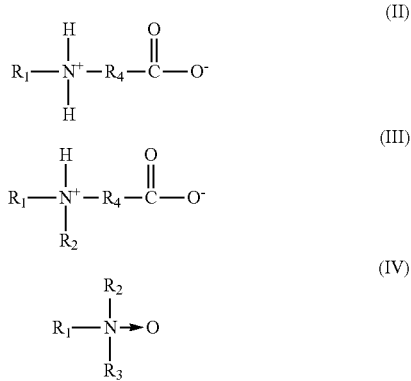

wherein $R_1$, $R_2$, $R_3$ and $R_4$ are as described above with respect to formula (I).

Some specific examples of amphoteric surfactants include, for example, alkyl betaine, amino betaine, N-alkyl beta-alanine, amide betaine, imidazoline betaine, and amine oxides, such as myristyl dimethylamine oxide, also known as N,N-dimethyltetradecyl amine oxide. Examples of myristyl dimethylamine oxide include, and without being limited thereto, Ammonyx™ MO.

"Cationic surfactant" means a surfactant that possesses a "head group" that contains a positive ionic charge.

A "gemini surfactant" is a type of surfactant that possesses two surfactant moieties, each comprising a hydrophobic tail and a polar head group, joined by a spacer/linker. FIG. 1 shows the general structure of a gemini surfactant. The hydrophilic and hydrophobic groups of each surfactant moiety may be any of those known to be used in conventional surfactants having one hydrophilic group and one hydrophobic group. Gemini surfactants are typically denoted with the nomenclature m-s-n, where m and n denote the length of the hydrophobic tail and s denotes the spacer length. A gemini surfactant is considered symmetric if m=n, and asymmetric if m≠n. As an example, 14-6-14 is a symmetric gemini surfactant where both tails are 14 carbons long and the spacer is 6 carbons long;

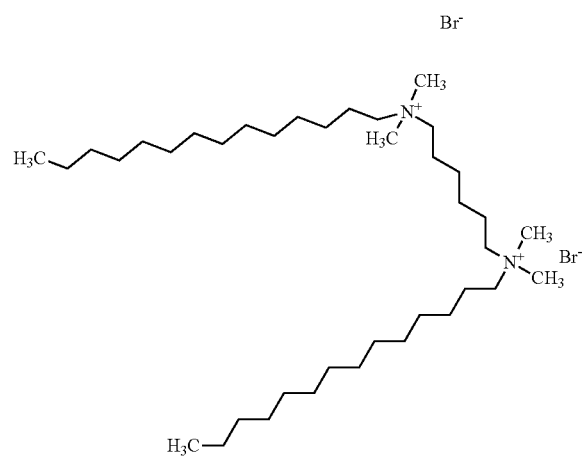 [SMILES: [Br-] ; CCCCCCCCCCCCCC[N+](C)(C)CCCCCC[N+](C)(C)CCCCCCCCCCCCCC ; [Br-]]

It will be understood that m and n may be of any suitable length and may be the same or different. For example, m and n may independently have from about 6 to about 24 carbon atoms, such as from about 6, about 7, about 8, about 9, about 10, about 11, about 12, about 13, about 14, about 15, about 16, about 17, about 18, about 19, about 20, about 21, about 22, or about 23 to about 7, about 8, about 9, about 10, about 11, about 12, about 13, about 14, about 15, about 16, about 17, about 18, about 19, about 20, about 21, about 22, about 23, or about 24 carbon atoms. Typically, m and n independently have from about 8 to about 22 carbon atoms, more typically 10 to 18 carbon atoms, and more typically 14 to 18 carbon atoms.

It will also be understood that m and n may independently be a substituted or unsubstituted hydrocarbyl chain or a substituted or unsubstituted heterogeneous chain.

Typical chains are, for example, alkyl, alkoxyalkyl, alkylaryl, or alkylamidoalkyl. The polar head groups of the gemini surfactant may independently be cationic, anionic, amphoteric, or non-ionic. Typically, the polar head groups are cationic and, typically, the cation is, for example, ammonium, substituted ammonium such as alkyl substituted ammonium, or quaternary ammonium. The anion (counterion) of such a gemini surfactant is typically a halide, most typically, bromide. Typically, there are two head groups and two hydrophobic tails, however, gemini surfactants comprising other arrangements, such as those having three head groups and two hydrophobic tails are also contemplated for use herein.

Likewise. It will be understood that the spacer s can be of any suitable length and may be flexible or rigid, aromatic or non-aromatic, a substituted or unsubstituted hydrocarbyl chain, a substituted or unsubstituted heterogeneous chain, and symmetrical or asymmetrical. Thus, the gemini surfactant need not be symmetrically disposed about the center of the spacer. The spacer may connect the two hydrophobic tails via both of their polar head groups or it may connect the hydrophobic tails at a point away from one or both of the polar head groups. Typically, the spacer comprises from about 1 to about 12 carbon atoms, such as from about 1, about 2, about 3, about 4, about 5, about 6, about 7, about 8, about 9, about 10, or about 11 to about 2, about 3, about 4, about 5, about 6, about 7, about 8, about 9, about 10, about 11, or about 12 carbon atoms. For example, the spacer may be $-(CH_2)_x-$, wherein x=2-12; $-(CH_2)_x-O-(CH_2CH_2O)_y CH_{2z}-$ wherein x=0-3, y=0-3, z=0-3 and x+y+z>0; $-(CH_2)_x N(CH_3)(CH_2)_y-$ wherein x=1-3 and y=1-3.

Specific examples of gemini surfactants may be found in the surfactant literature, for example, in "Gemini Surfactants: A distinct class of self-assembling Molecules" (S. P Moulik et al., Current Science, vol. 82, No. 9, 10 May 2002) and "Gemini Surfactants" (Surfactant Science Series Vol. 117, Ed, R, Zana, 2003, Taylor & Francis Publishers, Inc), Okahara et al., J, Japan Oil Chem. Soc. 746 (Yukagaku) (1989); Zhu et al., 67 JAOCS 7,459 (July 1990); Zhu et al., 68 JAOCS 7,539 (1991); Menger et al., J. Am. Chemical Soc. 113, 1451 (1991); Masuyama et al., 41 J. Japan Chem. Soc. 4,301 (1992); Zhu et al., 69 JAOCS 1, 30 (January 1992); Zhu et al., 69 JAOCS 7,626 July 1992); Menger et al., 115 J. Am. Chem. Soc. 2, 10083 (1993): Rosen, Chemtech 30 (March 1993); and Gao et al., 71 JAOCS 7,771 (July 1994), U.S. Pat. Nos. 2,374,354, Kaplan; 2,524,218, Bersworth; 2,530,147 Bersworth (two hydrophobic tails and three hydrophilic heads); 3,244,724, Guttmann; 5,160,450, Okahara, et al., each of which is incorporated herein by reference in their entirety.

The gemini surfactants may be anionic, nonionic, cationic, or amphoteric. For example, a typical nonionic gemini surfactant, e.g., a bis-polyoxyethylene alkyl ether, would contain two polyoxyethylene alkyl ether moieties. Each moiety would contain a hydrophilic group, e.g., polyethylene oxide, and a hydrophobic group, e.g., an alkyl chain.

Typically, gemini surfactants can self-assemble at low concentrations and have better surface activity than conventional surfactants. Gemini surfactants are very attractive for catalysis and adsorption applications, new synthetic vectors for gene transfection, analytical separations, solubilization processes, nanoscale technology, biotechnology, enhanced oil recovery, and as paint additives.

Further examples of gemini surfactants contemplated herein are represented by formula (V):

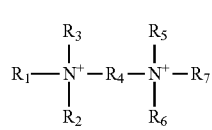

wherein:

$R_1$ and $R_7$ are each Independently a hydrophobic group, wherein the hydrophobic group comprises a substituted or unsubstituted hydrocarbon group, or a substituted or unsubstituted heterogeneous group;

$R_2$, $R_3$, $R_5$ and $R_6$ are each independently selected from hydrogen or a substituted or unsubstituted hydrocarbon group, and a substituted or unsubstituted heterogeneous group; and $R_4$ is selected from a substituted or unsubstituted hydrocarbon group, and a substituted or unsubstituted heterogeneous group.

In more typical embodiments, $R_1$ and $R_7$ independently represent a hydrophobic group and may be the same or different, wherein the hydrophobic group is selected from unsaturated or saturated alkyl, unsaturated or saturated aralkyl, unsaturated or saturated heteroaralkyl, unsaturated or saturated alkoxyalkyl, and unsaturated or saturated alkylamidoalkyl, wherein each group may be substituted or unsubstituted. In further embodiments, the alkyl represents a group that contains from about 6 to about 24 carbon atoms.

In more typical embodiments, $R_2$, $R_3$, $R_5$, and $R_6$ are each Independently selected from hydrogen, unsaturated or saturated alkyl, unsaturated or saturated aralkyl, unsaturated or saturated heteroaralkyl, unsaturated or saturated alkoxyalkyl, unsaturated or saturated carboxyalkyl, unsaturated or saturated hydroxyalkyl, unsaturated or saturated hydroxyalkyl-polyoxyalkylene, wherein each group may be substituted or unsubstituted. In further embodiments, each group has from about 1 to 20 carbon atoms, more typically 1 to 10 carbon atoms, and most typically from about 1 to 6 carbon atoms. Typical alkyl groups include methyl and ethyl, typical aralkyl groups include benzyl, typical hydroxyalkyl groups include hydroxyethyl and hydroxypropyl, and typical carboxyalkyl groups include acetate and propionate.

In another embodiment, $R_4$ is an unsaturated or saturated hydrocarbyl group. Typically, the hydrocarbyl group is an alkylene group. More typically, the alkylene group has a chain length of from about 1 to about 12 carbon atoms. Most typically, the alkylene group has a chain length of about 1 to about 4 carbon atoms. The group may include methylene and ethylene groups.

In further embodiments, the gemini surfactant is selected from the group of gemini surfactants known as the N,N'-dialkyl-N,N,N',N'-tetraalkylalkylene-α,ω-diaminium dibromides, including the bis(alkyldimethylammonium) alkylene dibromide series.

Some specific examples of gemini surfactants include, without being limited thereto, N,N'-didodecyl-N,N, N',N'-tetramethylbutane-1,4-diaminium dibromide (12-4-12), N,N'-didodecyl-N,N,N',N'-tetramethylbutane-1,4-diaminium dibromide (12-4-12), N,N'-didodecyl-N,N,N',N'-tetramethylhexane-1,6-diaminium dibromide (12-6-12), N,N'-ditetradecyl-N,N,N',N'-tetramethylhexane-1,6-diaminium dibromide (14-6-14), N,N'-dihexadecyl-N,N,N', N'-tetramethylbutane-1,4-diaminium dibromide (16-4-16), and N,N'-hexadecyl-N,N,N',N'-tetramethyloctane-1,8-diaminium dibromide (16-8-16). In a typical embodiment, the gemini surfactant is N,N'-ditetradecyl-N,N,N',N'-tetramethylhexane-1,6-diaminium dibromide (14-6-14).

In an embodiment, the gemini surfactant is chosen so that the resultant surfactant composition does not substantially interfere with the reduction of the metal cations to metal.

The term "hydrophobic group" means tending not to dissolve in, mix with or be wetted by water.

The term "hydrocarbon group" or "hydrocarbyl group" means a chain of carbon atoms, typically 10 to 25 carbon atoms and more typically 12 to 24 carbon atoms, Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group.

Where the term "alkyl group" is used, either alone or within other terms such as "haloalkyl group" and "alkylamino group", it encompasses linear or branched carbon radicals having, for example, one to about twenty-five carbon atoms (depending on whether or not hydrophobicity is required) or, in specific embodiments, one to about twelve carbon atoms. In other embodiments, alkyl groups are "lower alkyl" groups having one to about six carbon atoms, Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms. Other alkyl groups encompass linear or branched carbon radicals having, for example, twelve to about twenty-five carbon atoms. Typically, alkyl groups are saturated. Unsaturated alkyl groups may have one or more double bonds, one or more triple bonds, or combinations thereof. Typical unsaturated alkyl groups have one or two double bonds or one triple bond; more typically unsaturated alkyl groups have one double bond.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six cartoon atoms and one or more hydroxyl groups. Examples of such groups include hydroxymethyl, hydroxyethyl, hydroxypropyl, hydroxybutyl and hydroxyhexyl.

The term "alkoxy group" or "alkoxyalkyl group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups, in other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups have two rings typically having 8 to 12 carbon atoms, typically 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N, N-dimethyl-aminoethyl, N, N-diethylaminomethyl and the like.

The term "alkylamidoalkyl group" encompasses amidoalkyl groups having the nitrogen atom of the amide independently substituted with an alkyl group. In certain embodiments, the alkylamidoalkyl groups are "loweralkylamidoalkyl" groups having alkyl groups of one to six carbon atoms. In other embodiments, the lower alkylamidoalkyl groups have alkyl groups of one to three carbon atoms. Suitable alkylamidoalkyl groups may be mono or dialkyl substituted, such as N-methylamidomethyl, N, N-dimethyl-amidoethyl, N, N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "substituted" used in conjunction with the groups described herein refers to a chemically acceptable group, i.e., a moiety that does not negate the activity of the surfactants. It is understood that substituents and substitution patterns on the surfactants may be selected by one of ordinary skill in the art to provide compounds that are chemically stable and that can be readily synthesized by techniques known in the art. If a substituent is itself substituted with more than one group, it is understood that these multiple groups may be on the same carbon/member atom or on different carbons/member atoms, as long as a stable structure results. Illustrative examples of some suitable substituents include, for example, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl.

In an embodiment, the amphoteric and/or gemini surfactant is chosen so that the resultant surfactant composition does not substantially interfere with the reduction of metal cations to metal.

In another embodiment, the amphoteric and/or gemini surfactant is used in a pH range wherein the surfactant is substantially neutral, such as, for example, a pH of 7 at 298 K.

In an embodiment, at least one surfactant used in the compositions and methods described herein forms micelles. In another embodiment, the micelles are wormlike micelles. "Wormlike micelles" are elongated flexible self-assembly structures formed by the aggregation of amphiphiles. Above a threshold concentration, they entangle into a dynamic network, reminiscent of polymer solutions, and display viscoelastic properties. For example, the zwitterionic surfactant may form worm-like micelles and/or the gemini surfactant may form worm-like micelles In another embodiment, the selection of at least one surfactant is made so as to improve the solubility of at least one other surfactant used in the methods and compositions described herein. For example, the amphoteric surfactant may be chosen so as to improve the solubility of the zwitterionic surfactant. Further, the gemini surfactant may be chosen so as to improve the solubility of another surfactant.

In another embodiment, at least one surfactant used in the compositions and methods described herein stabilizes the reduced neutral metal particles. For example, the amphoteric and/or gemini surfactant may be chosen to stabilize the reduced metal particles.

In another embodiment, the surfactant(s) chosen for use in the compositions and methods described herein form a stable surfactant composition. The term "stable" means the composition does not undergo any significant changes in morphology that can affect the production and dispersion of metal nanoparticles.

In certain embodiments, when more than one surfactant is used in the methods and compositions described herein, the surfactants are chosen so that their hydrocarbon tails are of the same length or are of substantially the same length.

In certain embodiments, one or more of the surfactant(s) used herein are pharmaceutically acceptable and, more specifically, non-toxic.

It will be understood that the surfactants described herein can be in a dry form or in a solution. When in solution, a "solvent" is used in which the surfactant(s) is typically soluble. Examples of suitable solvents include water, low molecular weight alcohols (such as methanol, ethanol, propanol, butanol, glycol, etc.), hydrocarbons, and mixtures thereof. The solvent is generally selected to avoid substantial interference with reduction of metal cations to metal.

"Non-turbid" means a solution that is substantially clear or transparent to the naked eye and that may be comparable to, for example, deionized water. For example, surfactants, such as at least one amphoteric surfactant and at least one zwitterionic surfactant, are combined in amounts such that a non-turbid solution is formed. Such amounts of the at least one amphoteric surfactant to the at least one zwitterionic surfactant are, for example, from about 0.04:0.96 to about 0.96:0.04 (w/w), more typically, from about 0.10:0.90 to about 0.90:0.10 (w/w); from about 0.3:07 to about 07:0.3 (w/w); or from about 0.6:0.4 to about 0.4:0.6 (w/w) based on the total weight of surfactants.

The term "reducing agent" is used herein to refer to substances that are capable of donating electrons to other substances in a chemical redox reaction. In particular, the reducing agents described herein are capable of reducing metal cations to metal. Generally, the reducing agents are mild reducing agents. Examples of reducing agents include ascorbic acid, glucose, glucosamine, hydroquinone, aluminum, calcium, hydrogen, manganese, potassium, sodium borohydride, sodium triacetoxyborohydride, compounds containing the $Sn^{2+}$ ion, such as tin(II) chloride, sulfite compounds, hydrazine, zinc-mercury amalgam, diisobutylaluminum hydride, oxalic acid, formic acid, phosphites, hypophosphites, phosphorous acid, dithiothreitol (DTT), compounds containing the $Fe^{2+}$ ion, such as iron(II) sulfate, carbon monoxide, carbon, tris(2-carboxyethyl)phosphine HCl, and combinations thereof. Typically, the reducing agent is ascorbic acid and/or sodium borohydride.

The term "seed solution" refers to a solution containing metal seeds. In an embodiment, the metal seeds are grown in the seed solution.

The term "growth solution" refers to a solution in which metal nanorods are grown.

"Hydrotropes" are a class of compounds that normally increase the aqueous solubility of sparingly-soluble solutes in solution. Besides solubilization, hydrotropes have uses in vesicle preparation and selective separation, as stabilizers of o/w microemulsion, viscosity modifiers and as clearing agents in cloudy detergent formulation. Alkylbenzene sulphonates based on toluene, xylene and cumene, polyhydroxy benzene, sodium salts of lower alkanols and derivatives of aromatic acids are generally considered to be effective hydrotropes. (see S. E. Friberg and M. Chiu, J. Dispersion Science and Technology, 9(5&6), pages 443 to 457, (1988-

1989), incorporated herein by reference in its entirety). Typically, the hydrotrope is sodium salicylate.

A "coacervate" refers to a spherical aggregate of colloidal droplets held together by hydrophobic forces. The term "coacervate" derives from the Latin coacervare, meaning "to assemble together or cluster." The term "coacervation" is often used to describe a unique type of electrostatically-driven liquid-liquid phase separation, often resulting from the association of oppositely charged macro-ions. Coacervate droplets can measure, for example, from about 1 to about 100 μm in diameter, whereas their soluble precursors are typically sized in the nanometer range. Methods described herein, in embodiments, illustrate collection of coacervate layers and nanoparticle separation. The use of a salt solution, including but not limited to, sodium salicylate, can result in the spontaneous formation of coacervates. Typically, the salt solution, such as sodium salicylate, is used in an amount of from about 0.2 to about 2.0 wt %, or more typically, from about 0.4 to about 1.0 wt %.

A "bilayer" refers to molecular layers, for example, wherein a first region on either side of the bilayer is the hydrophilic headgroups and the second region within the core of the bilayer is the hydrophobic tails. In embodiments, the bilayer may be a surfactant bilayer adsorbed on the surface of metal nanoparticles (e.g. nanorods). In an example, moving outward from the metal surface of the metal nanoparticles, surfactant head groups are encountered, followed by surfactant tails of one layer, then surfactant tails, followed by surfactant headgroups of a second layer. The surfactant may be the same or different.

A "surfactant phase separation" refers to the transition of a surfactant solution from clear to slightly cloudy, floating surfactant crystals, and/or floating surfactant precipitates.

A "capping agent" refers to a chemical entity that is adsorbed on the surface of metal nanoparticles and provides stability against substantial aggregation of nanoparticles.

A "bio-conjugate" refers to a substantially stable complex of metal nanoparticles (e.g. nanorods) and biomolecules through covalent or non-covalent bonding.

"Substantially free" herein means less than about 5%, typically less than about 2%, more typically less than about 1%, even more typically less than about 0.5%, most typically less than about 0.1% contamination with the agent in question, such as a cytotoxic surfactant, for example, CTAB.

"Nanopure water" refers to water that has been triply de-ionized and has a relatively high resistivity and, it is typically, charcoaled filtered (e.g. few conducting particles and dissolved solids present).

A "mixture" or "combination" are terms that may be used interchangeably. A mixture is not limited to two or more components that have been mixed. A mixture may be two or more components combined without having been mixed.

An "essentially pure" metal nanorod composition means a composition comprising at least about 90% by weight of metal nanorods, based on the total weight of the composition, typically at least about 95% by weight, at least about 96% by weight, at least about 97% by weight, at least about 98% by weight, or at least about 99% by weight of metal nanorods, based on the total weight of the composition.

"Substantially uniform length, diameter, and/or aspect ratio" is used to refer to a population of metal nanorods wherein a majority of the metal nanorods have the same length, diameter, and/or aspect ratio within an acceptable variance for a subsequent analysis of the population. The population can be a single population in a sample or a subpopulation within a sample. In particular embodiments, the acceptable variance for the length, diameter, and/or aspect ratio of any given metal nanorod in the population or subpopulation can be at most 10%, 8%, 5%, 2%, 1% or 0.1% different from the average length, diameter, and/or aspect ratio for metal nanorods in the population. In embodiments, the population can be composed of at least 90%, 95%, 99% or 99.9% metal nanorods having a particular length, diameter, and/or aspect ratio.

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slowdown or otherwise decrease the pathology of a disease or disorder such as cancer, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat cancer. Effective amounts of the metal nanorods described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The metal nanorods described herein may, In embodiments, be administered before, during or after treatment with conventional therapies for the disease or disorder in question, such as cancer.

The terms "diagnostic effective amount" or "imaging effective amount" mean a quantity sufficient, when administered to a subject, including a mammal, for example a human, to achieve a desired result, for example an amount effective to diagnose or image a tumour. In embodiments, a diagnostic or imaging effective amount is distinct from a therapeutically effective amount.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, Isotonic and/or absorption delaying agents and the like. The use of pharmaceutically acceptable carriers is well known.

The term "non-toxic" refers to the non-occurrence of pathological phenomena as a result of using pharmacological levels of the metal nanorods described herein. The term substantially non-toxic is defined as including acceptably low toxicity as well as non-toxicity.

In understanding the scope of the present application, the articles "a", "an", "the", and "said" are intended to mean that there are one or more of the elements. Additionally, the term "comprising" and its derivatives, as used herein, are intended to be open ended terms that specify the presence of the staled features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any embodiments described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. For example, in embodiments, the use of gold seeds, the use of a cytotoxic surfactant, such as CTAB, and/or the exchange of surfactant with a polymeric stabilizer is explicitly excluded from the compositions and methods described herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

It is also to be understood that the terminology used herein is for the purpose of describing particular aspects only, and is not intended to be limiting. Patent applications, patents, and publications are cited herein to assist in understanding the aspects described. All such references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

Metal Nanorods

Current commercial methods for growing gold nanorods most often utilize the cationic surfactant cetyltrimethylammonium bromide (CTAB) as the surfactant medium in which the gold nanorods are prepared. Unfortunately, CTAB is cytotoxic and certain applications of metal nanorods require the solution to be "CTAB-free." Even the best methods of purification cannot remove 100% of the CTAB. Hence, metal nanorods grown using CTAB are often wrapped in polymeric molecules in order to be used in such applications. Accordingly, described herein are metal nanorods, such as gold nanorods, that are substantially free of a cytotoxic surfactant, such as a cationic surfactant and, more specifically, metal nanorods that are substantially free or free of CTAB.

Furthermore, since the metal nanorods described herein are substantially free or free of a cytotoxic surfactant such as CTAB, a polymeric stabilizer is not needed to "wrap" the metal nanorods or exchange with the cytotoxic stabilizer. Therefore, in other or additional embodiments, the metal nanorods described herein do not comprise a polymeric stabilizer.

In other embodiments the metal nanorods are produced using a composition free of metal seeds (e.g. gold seeds) or using metal seeds that are free of CTAB (or another cytotoxic surfactant). As has been noted above, the length of the metal nanorods generated in conventional methods is influenced by the ratio of the metal seeds to chlorauric acid in the growth solution. Despite this, uniformity in the diameter, length, and aspect ratio of metal nanorods has been difficult to achieve. By avoiding the use of metal seeds and/or by using metal seeds in combination with a gemini surfactant, the metal nanorods described herein are, in embodiments, substantially uniform in length, diameter, and/or aspect ratio.

Furthermore, the metal nanorods described herein are in embodiments non-toxic and/or pharmaceutically acceptable and are therefore suitable for in vivo use in treating diseases or disorders such as cancer, or for diagnostic or imaging purposes. Compositions comprising the metal nanorods described herein are also contemplated, including pharmaceutically acceptable compositions and industrially useful compositions.

Various types of pharmaceutical compositions can be used, depending on the desired form of administration. For example, aqueous compositions comprise an effective amount of the metal nanorods described herein dissolved and/or dispersed in a pharmaceutically acceptable carrier and/or aqueous medium. The pharmaceutical compositions described herein can further comprise supplementary active ingredients, such as an anti-cancer agent.

According to certain embodiments, the pharmaceutical composition is formulated for parenteral administration, e.g., formulated for injection via the intravenous, intramuscular, sub-cutaneous, intralesional, and intraperitoneal routes. Typically, such compositions are prepared either as liquid solutions or suspensions; solid forms suitable for using to prepare solutions and/or suspensions upon the addition of a liquid prior to Injection can also be prepared; and the preparations can also be emulsified. The metal nanorod compositions described herein can be formulated into a composition in a neutral and/or salt form for example. Any pharmaceutically acceptable salt known to a person skilled in the art can be used, providing it would not interfere with the function of the metal nanorods.

Sterile injectable solutions are generally prepared by incorporating the active compounds, specifically the metal nanorods in the required amount in the appropriate solvent with other ingredients as detailed above, as required, followed by filtered sterilization.

Generally, dispersions are prepared by incorporating the various sterilized active ingredients into a sterile vehicle which contains the basic dispersion medium and/or the required other ingredients as described herein above. In the case of sterile powders for the preparation of sterile injectable solutions, the typical methods of preparation are vacuum-drying and/or freeze-drying techniques which yield a powder of the active ingredient plus any additional desired Ingredient from a previously sterile-filtered solution thereof. The preparation of more, and/or highly, concentrated solutions for direct Injection is also contemplated, where the use of DMSO as solvent is envisioned to result in extremely rapid penetration, delivering high concentrations of the active agents to a small target area.

Upon formulation, solutions are administered in a manner compatible with the dosage formulation and/or in such amount as is therapeutically effective. The formulations are easily administered in a variety of dosage forms, such as the type of injectable solutions described above, but drug release capsules and/or the like can also be employed. Other pharmaceutically acceptable forms of the metal nanorod compositions include, for example, tablets and/or other solids for oral administration; liposomal formulations; time release capsules; and/or any other form currently in use, including creams. One may also use nasal solutions and/or sprays, aerosols and/or inhalants compositions of metal nanorods described herein. Nasal solutions are usually aqueous solutions designed to be administered to the nasal passages in drops and/or sprays.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides.

Other delivery methods of the present invention comprise compositions comprising one or more lipids associated with at least one metal nanorod. A lipid is a substance that is characteristically insoluble in water and extractable with an organic solvent. Lipids include, for example, the substances comprising the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. These examples are not meant to be limiting, and compounds other than those specifically described herein that are understood by one of skill in the art as lipids are also encompassed by the compositions and methods of the present invention. For example, a lipid may be naturally occurring or synthetic (i.e., designed or produced by man). However, a lipid is usually a biological substance. Biological lipids are well known, and include for example, neutral fats, phospholipids, phosphoglycerldes, steroids, terpenes, lysoliplds, glycosphingolipids, glycolipids, sulphatides, lipids with ether and ester-linked fatty acids and polymerizable lipids, and combinations thereof. In particular embodiments, a lipid comprises a liposome. A liposome is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition.

A multilamellar liposome has multiple lipid layers separated by aqueous medium. They form spontaneously when lipids comprising phospholipids are suspended in an excess of aqueous solution. The lipid components undergo self-rearrangement before the formation of closed structures, entrapping water and dissolved solutes between the lipid bilayers. Lipophilic molecules or molecules with lipophilic regions may also dissolve in or associate with the lipid bilayer.

In particular embodiments, a metal nanorod may be, for example, encapsulated in the aqueous interior of a liposome, interspersed within the lipid bilayer of a liposome, attached to a liposome via a linking molecule that is associated with both the liposome and the metal nanorod, entrapped in a liposome, complexed with a liposome, etc.

A liposome used as described herein may be made by different methods, as would be known to one of ordinary skill in the art. Phospholipids can form a variety of structures other than liposomes when dispersed in water, depending on the molar ratio of lipid to water. At low ratios the liposome is the typical structure.

The size of a liposome varies depending on the method of synthesis. Liposomes described herein can have a variety of sizes. In certain embodiments, the liposomes are small, e.g., less than about 100 nm, about 90 nm, about 80 nm, about 70 nm, about 60 nm, or less than about 50 nm in external diameter. In preparing such liposomes, any protocol described herein, or as would be known to one of ordinary skill in the art may be used. Additional non-limiting examples of preparing liposomes are described in U.S. Pat. Nos. 4,728,575, 4,737,323, 4,533,254, 4,162,282, 4,310,505, and 4,921,706; A comprehensive review of lipid vesicles and methods for their preparation are described in "Liposome Technology" (1984, Gregoriadis G, ed. CRC Press Inc Boca Raton Florida Vol I II & III).

Liposomes interact with cells to deliver agents via four different mechanisms: Endocytosis by phagocytic cells of the reticuloendothelial system such as macrophages and/or neutrophils; adsorption to the cell surface, either by non-specific weak hydrophobic and/or electrostatic forces, and/or by specific interactions with cell-surface components; fusion with the plasma cell membrane by insertion of the lipid bilayer of the liposome into the plasma membrane, with simultaneous release of liposomal contents into the cytoplasm; and/or by transfer of liposomal lipids to cellular and/or subcellular membranes, and/or vice versa, without any association of the liposome contents, Varying the liposome formulation can alter which mechanism is operative, although more than one may operate at the same time.

According to certain embodiments, ligands are added to the liposomes to facilitate the delivery of the metal nanorod-containing liposomes to the desired cell or tissue. Although targeting ligands are described herein in reference to liposomes, it will be understood that this description refers equally to targeting ligands that may be used in the absence of liposomes. Targeted delivery is achieved by the addition of ligands without compromising the ability of these liposomes to deliver large amounts of metal nanorods. It is contemplated that this will enable delivery to specific cells, tissues and organs. The targeting specificity of the ligand-based delivery systems is based on the distribution of the ligand receptors on different cell types. The targeting ligand may either be non-covalently or covalently associated with the lipid complex, and can be conjugated to the liposomes by a variety of methods. Further, the targeting ligand may be non-covalently or covalently associated with the metal nanorods themselves in the absence of a lipid complex.

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer, Typical reactive groups include amino groups, carboxylic groups, hydrazide groups, and thiol groups. The coupling of the targeting ligand to the hydrophilic polymer can be performed by standard methods of organic chemistry that are known to those skilled in the art. In certain embodiments, the total concentration of the targeting ligand can be, for example, from about 0.01 to about 10% mol.

Targeting ligands are any ligand specific for a characteristic component of the targeted region, Typical targeting ligands Include proteins such as polyclonal or monoclonal antibodies, antibody fragments, or chimeric antibodies, enzymes, or hormones, or sugars such as mono-, oligo- and poly-saccharides. For example, disialoganglioside GD2 is a tumor antigen that has been identified in neuroectodermal origin tumours, such as neuroblastoma, melanoma, small-cell lung carcinoma, glioma and certain sarcomas. Liposomes containing anti-disialoganglioside GD2 monoclonal antibodies have been used to aid targeting of the liposomes to cells expressing the tumor antigen. In another non-limiting example, breast and gynecological cancer antigen specific antibodies are described in U.S. Pat. No. 5,939,277. In a further non-limiting example, prostate cancer specific antibodies are disclosed in U.S. Pat. No. 6,107,090. Thus, it is contemplated that the antibodies as would be known to one of ordinary skill in the art may be used to target the metal nanorods described herein to specific tissues and cell types. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumours.

In certain embodiments, in order to enhance the transduction of cells, to increase transduction of target cells, or to limit transduction of undesired cells, antibody or cyclic peptide targeting moieties (ligands) are associated with the lipid complex or metal nanorods. Such methods are known in the art. For example, liposomes that specifically target cells of the mammalian central nervous system have been described in U.S. Pat. No. 5,786,214. The liposomes are composed essentially of N-glutarylphosphatidylethanolamine, cholesterol and oleic acid, wherein a monoclonal antibody specific for neuroglia is conjugated to the liposomes. It is contemplated that a monoclonal antibody or antibody fragment may be used to target delivery to specific cells, tissues, or organs in the animal, such as for example, brain, heart, lung, liver, etc.

Still further, a metal nanorod may be delivered to a target cell via receptor-mediated delivery and/or targeting vehicles comprising a lipid or liposome. These take advantage of the selective uptake of macromolecules by receptor-mediated endocytosis that will be occurring in a target cell. In view of the cell type-specific distribution of various receptors, this delivery method adds another degree of specificity to the embodiments described herein. Thus, in certain embodiments, a ligand will be chosen to correspond to a receptor specifically expressed on the target cell population. A cell-specific metal nanorod delivery and/or targeting vehicle may comprise a specific binding ligand in combination with a liposome. The metal nanorods to be delivered are housed within a liposome and the specific binding ligand is functionally incorporated into a liposome membrane. Alternatively, the specific binding ligand is functionally incorporated onto the metal nanorod itself. The liposome or metal nanorod will thus specifically bind to the receptors) of a target cell and deliver the contents to a cell. Such systems have been shown to be functional using systems in which, for example, epidermal growth factor (EOF) is used in the receptor-mediated delivery of a nucleic acid to cells that exhibit upregulation of the EGF receptor.

In still further embodiments, the specific binding ligand may comprise one or more lipids or glycoproteins that direct cell-specific binding. For example, U.S. Pat. No. 5,432,260 discloses that the sugars mannosyl, fucosyl or N-acetyl glucosamine, when coupled to the backbone of a polypeptide, bind the high affinity mannose receptor. It is contemplated that the metal nanorods described herein can be specifically delivered into a target cell or tissue in a similar manner.

Folate and the folate receptor have also been described as useful for cellular targeting (U.S. Pat. No. 5,871,727). In this example, the vitamin folate is coupled to the liposome or metal nanorod. The folate receptor has high affinity for its ligand and is overexpressed on the surface of several malignant cell lines, including lung, breast and brain tumours.

Anti-folates such as methotrexate may also be used as targeting ligands. Transferrin mediated delivery systems target a wide range of replicating cells that express the transferrin receptor.

A skilled person realizes that the systems and methods of the present invention can be employed in a variety of types of experimental, therapeutic and diagnostic procedures, including in vitro or In vivo experimental procedures, In another embodiment, systems, devices, materials, and techniques are described for minimally invasive active targeting, fluorescent imaging, and NIR photothermal treatment of tumours, for example, which can be applied to a variety of cancer types.

Methods of Producing Metal Nanorods

Methods of Making Metal Nanorods Involving the Use of a Surfactant Comprising a Charged Moiety In an embodiment, the metal nanorods described herein are produced by combining a source of metal cations with at least one surfactant comprising at least one positively charged moiety and/or at least one negatively charged moiety to form a mixture, wherein the metal cations are reduced and metal nanorods are produced.

The at least one surfactant may act as the reducing agent and/or at least one reducing agent may be added to reduce the metal cations. The mixture may be maintained at any suitable temperature over any suitable time period that promotes the formation of metal nanorods. Typically, the temperature is maintained at about 20° C. to about 50° C., about 20° C. to about 45° C., about 20° C. to about 40° C., about 25° C. to about 40° C., or about 25° C. to about 30° C. The time period may be from about a few minutes to about several hours, such as, and without being limited thereto, up to about 24 hours, or about 12 hours to about 24 hours.

In embodiments of the methods described herein, the positively charged moiety comprises at least one secondary amine, tertiary amine, or quaternary ammonium and/or the negatively charged moiety comprises a carboxyl group.

In another embodiment, the at least one surfactant is used in an amount of from about 0.05 wt % to about 5 wt % based on the total weight of the mixture. Typical ranges include from about 0.25 wt % to about 3 wt % and, more typically from about 0.5 wt % to 3 wt %. When two surfactants are used, typical ranges include from about 0.5 wt % to about 3 wt % for the first surfactant and from about 0.25 wt % to about 3 wt % for the second surfactant.

In another embodiment, the surfactant(s) chosen for use in the compositions and methods described herein form a stable surfactant composition, Typically, the methods described herein involve the use of a first surfactant and a second surfactant, which are typically different.

Metal nanorods produced by the methods described herein are, in embodiments, non-toxic, pharmaceutically acceptable, and suitable for in vivo use in effective concentrations for the desired outcome, such as treatment of cancer, imaging, etc.

The method, in embodiments, generates the metal nanorods in gram quantities suitable for industrial scale applications. Thus, in embodiments, the method is scalable and produces metal nanorods that are substantially uniform in size and/or shape. In other embodiments, the nanorods are produced in good yield and metal waste is reduced.

Metal nanorods produced by the methods described herein are, in embodiments, candidates for pharmaceutical treatments, and suitable for in vivo use in effective concentrations for the desired outcome, such as treatment of cancer, imaging, etc.

In still other embodiments, the methods described herein provide a simplified purification process for the metal nanorods and, thus, a combined production and purification process is contemplated herein. By selecting surfactants with different solubilities, the resultant mixture separates with the metal nanorods being predominantly in one layer and relatively pure.

Certain embodiments of such methods are further described as follows:

(I) Methods of Making Metal Nanorods Involving the Use of a First and Second Surfactants (OMNI)

In an embodiment, the metal nanorods described herein are produced by combining a source of metal cations with a first surfactant and a second surfactant to form a mixture, wherein the metal cations are reduced and metal nanorods are produced.

The surfactant may act as the reducing agent and/or at least one reducing agent may be added to reduce the metal cations. The mixture may be maintained at any suitable temperature over any suitable time period that promotes the formation of metal nanorods. Typically, the temperature is maintained at about 20° C. to about 50° C., about 20° C. to about 45° C., about 20° C. to about 40° C., about 25° C. to about 40° C., or about 25° C. to about 30° C. The time period may be from about a few minutes to about several hours, such as, and without being limited thereto, up to about 24 hours, or about 12 hours to about 24 hours.

In another embodiment, the first and second surfactants are used in an amount of from about 0.05 wt % to about 5 wt % based on the total weight of the mixture. Typical ranges include from about 0.05 wt % to about 3 wt %, from about 0.1 wt % to about 3 wt %, from about 0.25 wt % to about 3 wt %, from about 0.5 wt % to about 3 wt %, from about 0.05 wt % to about 2 wt %, from about 0.1 wt % to about 2 wt %, from about 0.25 wt % to about 2 wt %, or from about 0.5 wt % to about 2 wt %. In certain embodiments, ranges include from about 0.5 wt % to about 3 wt % for the first surfactant and from about 0.25 wt % to about 3 wt % for the second surfactant.

In embodiments, the first surfactant and second surfactant are independently selected from a zwitterionic surfactant and an amphoteric surfactant, wherein the first surfactant is an amphoteric surfactant and the second surfactant is a zwitterionic surfactant.

In another embodiment, the ratios of the first surfactant to the second surfactant are combined in amounts such that a non-turbid solution is formed. Typical ranges include from about from about 0.04:0.96 to about 0.96:0.04 (w/w), more typically, from about 0.10:0.90 to about 0.90:0.10 (w/w); from about 0.3:0.7 to about 0.7:0.3 (w/w); or from about 0.6:0.4 to about 0.4:0.6 (w/w) based on the total weight of surfactants.

In another embodiment, the surfactant(s) chosen for use in the compositions and methods described herein form a Stable surfactant composition.

In another embodiment, the source of metal cations is used in an amount of from about 0.004 wt % to about 0.04 wt % based on the total weight of the mixture. Typical ranges include from about 0.005 wt % to about 0.03 wt % and, more typically from about 0.007 wt % to 0.02 wt %.

In embodiments, in the methods described herein, there is a higher reduction of metal cations to nanoparticles (e.g. nanorods) compared to CTAB methods. In embodiments, there is at least about 40% reduction of the source of metal cations to nanoparticles; at least about 50% reduction to nanoparticles; at least about 60% reduction to nanoparticles; at least about 70% reduction to nanoparticles; at least about 80% reduction to nanoparticles; at least about 90% reduction to nanoparticles; or at least about 99% reduction to nanoparticles.

In another embodiment, the mixture further comprises a reducing agent. The reducing agent is used in an amount of from about 0.001 wt % to about 0.002 wt % based on the total weight of the mixture. Typical ranges include from about 0.001 wt % to about 0.0018 wt % and, more typically from about 0.0013 wt % to 0.0017 wt %.

Based on the description herein, one skilled in the art would know to adjust the amounts of the components in the methods described herein to achieve the desired metal nanorods.

The method described herein may be scaled-up. For example, the method may be scaled-up by increasing the total volume of the mixture, whereby the proportion of reactants such as surfactant(s) and source of metal cations is substantially maintained in comparison to the mixture at a lower volume. In embodiments, the total volume at a lower scale may be about 5 ml to about 500 ml and the scale-up volume may be up to about 4 L. The proportion of reactants at the lower scale may be similar to the proportion at the higher scale-up. In certain embodiments, the amount of metal cations may be adjusted further. With respect to the temperature, the temperature may be maintained. In typical scale-ups, the temperature may be lower than the temperature used in the lower volume to provide a similar or higher abundance of metal nanorods. The adjustment may depend on the desired nanorod size. In some embodiments, the reaction temperature of the scale-up is about 1° C. to about 3° C. lower than the temperature used at a lower volume or is about 1° C. to about 2° C. lower than the temperature used at a lower volume. In any event, one skilled in the art would understand how to adjust the conditions and reactants in the methods described herein to achieve scale-up.

In another embodiment, the reactants in the method described herein are not agitated. In another embodiment, the reactants in the method are agitated. Typically, the mixture is shaken at a speed of about 5 rpm to about 100 rpm.

The methods described herein are, in embodiments, conducted in a single-pot, meaning a single reaction vessel is used. In embodiments, the methods can be carried out in a single step by combining all of the reagents or components and aging the resultant mixture for a period of time.

With respect to the method described above and without wishing to be bound by a particular theory, it is believed that the metal cations in the mixture are reduced to metal salt from a higher oxidation state to the lowest non zero oxidation state by ascorbic acid or other milder reducing agents. The surfactant then reduces the metal cations from their lowest non-zero oxidation state to the zero oxidation state. The fully reduced metal cations start to cluster and this results in the formation of nanocrystals that are stabilized by mixed surfactant capping. These newly formed nanocrystals help to reduce additional metal cations to the zero oxidation state and consequently grow in size. Concurrently, the surfactant solution start undergoing a phase transition from small spherical micelles to liquid crystals and thereby governs the transition of nanocrystals to nanorods or other nanoparticles.

(ii) Methods of Making Metal Nanorods Involving the Use of a Gemini Surfactant

In an embodiment, the metal nanorods described herein are produced by combining a source of metal cations with at least one gemini surfactant to form a mixture, wherein the metal cations are reduced and metal nanorods are produced.

The gemini surfactant may act as the reducing agent and/or at least one reducing agent may be added to reduce the metal cations. In an embodiment, the method further comprises combining metal seeds (e.g. metal seed solution) with the source of metal cations and the gemini surfactant (e.g., growth solution). In another embodiment, the method further comprises forming the metal seeds, as will be described below in more detail.

In certain embodiments, the ratio of the metal seed solution amount to the growth solution amount is any amount that achieve the desired nanorod. Typical ranges include from about 0.005:0.995 to about 0.05:0.95 (w/w), 0.006:0.994 to about 0.05:0.95 (w/w), from about 0.008:0.992 to about 0.05:0.95 (w/w); from about 0.01:0.99 to about 0.05:0.95 (w/w), from about 0.005:0.995 to about 0.01:0.99 (w/w), from about 0.005:0.995 to about 0.009:0.991 (w/w); from about 0.005:0.995 to about 0.008:0.992 (w/w); or from about 0.005:0.995 to about 0.007:0.993 (w/w) based on the total weight of seed and growth solutions.

The mixture may be maintained at any suitable temperature over any suitable time period that promotes the formation of metal nanorods. Typically, the temperature is maintained at about 20° C. to about 50° C., about 20° C. to about 45° C., about 20° C. to about 40° C., about 25° C. to about 40° C., or about 25° C. to about 30° C. The time period may be from about a few minutes to about several hours, such as, and without being limited thereto, up to about 24 hours, or about 12 hours to about 24 hours.

In another embodiment, at least one surfactant is used in an amount of from about 0.05 wt % to about 5 wt % based on the total weight of the mixture. Typical ranges include from about 0.25 wt % to about 3 wt % and, more typically from about 0.5 wt % to 3 wt %. When two surfactants are used, typical ranges include from about 0.5 wt % to about 3 wt % for the first surfactant and from about 0.25 wt % to about 3 wt % for the second surfactant.

In another embodiment, the surfactant(s) chosen for use in the compositions and methods described herein form a stable surfactant composition. Typically, the methods described herein involve only the use of a single gemini surfactant; the use of two gemini surfactants may offer additional control over the length and aspect ratio of the gold nanorods. When two gemini surfactants are used, the first gemini surfactant and second gemini surfactant are typically selected from the classes of cationic gemini surfactants listed above.

In another embodiment, the source of metal cations is used in an amount of from about 0.004 wt % to about 0.04 wt % based on the total weight of the mixture. Typical ranges include from about 0.005 wt % to about 0.03 wt % and, more typically from about 0.007 wt % to 0.02 wt %.

In embodiments, in the methods described herein, there is a higher reduction of metal cations to nanoparticles (e.g. nanorods) compared to CTAB methods. In embodiments, there is at least about 40% reduction of the source of metal cations to nanoparticles; at least about 50% reduction to nanoparticles; at least about 60% reduction to nanoparticles; at least about 70% reduction to nanoparticles; at least about 80% reduction to nanoparticles; at least about 90% reduction to nanoparticles; or at least about 99% reduction to nanoparticles.

In another embodiment, the mixture further comprises a reducing agent. The reducing agent is used in an amount of from about 0.001 wt % to about 0.002 wt % based on the total weight of the mixture. Typical ranges include from about 0.0.001 wt % to about 0.0013 wt % and, more typically from about 0.0013 wt % to 0.0017 wt %.

In another embodiment, the rod length of the nanorods increases with increasing spacer length while the width of the rods stays relatively constant. Most conventional methods for growing metal nanorods have employed sixteen chain length carbon surfactants or longer. In embodiments, the method described herein can be used to produce metal nanorods with shorter chain length surfactants. For example, as is demonstrated below, the 12-X-12 series gemini surfactants were successfully used to grow metal nanorods. These gemini surfactants have a shorter tail length than surfactants used in conventional methods, and were used at a lower concentration as compared to methods that use CTAB. In addition, the common CTAB directed growth methods use a gold seed solution dispersed in CTAB. In embodiments, the methods described herein can be used to grow metal nanorods with both CTAB dispersed gold seeds and gemini dispersed gold seeds or gemini dispersed gold seeds alone.

Without wishing to be bound by a particular theory, it is believed that the metal cations in the mixture are reduced to metal, either by a surfactant in the composition or by use of an exogenous reducing agent. The surfactant is believed to bind to the surface of the growing metal particle and block the growth of the small metal particles along certain faces.

It has been known that the chemical nature of the surfactant used to produce metal nanorods is important. However, until now, there have been limited choices for useful surfactants.

It will be understood that the concentration of metal seeds in the seed solution, the concentration of the source for metal cations (e.g. gold (III) chloride), and the amount of added reducible salt (e.g. silver nitrate) all affect the aspect ratio and length of the resulting nanorods. Additionally, it will be understood that the method described herein, using gemini surfactant(s), is able to control various embodiments of the growth of the metal nanorods that lead to metal nanorods of the desired length and aspect ratio through variation of the surfactant architecture. Finally, it is well known that in the common seed-growth method using CTAB, the concentration of the surfactant cannot be reduced much below the commonly used concentration of 0.10 M (3.6 w/v %), without a significant decrease in the yield and the quality of the produced nanorods. In embodiments of the methods contemplated herein, the surfactant concentration used in the production of the metal nanorods is less than 50% that of CTAB, used in an otherwise equivalent method. The addition of aromatic counterions (such as salicylate or benzoate) during the production of the metal nanorods can further reduce the amounts of the gemini surfactants required while improving the quality and yield of nanorods of a dominant size/shape. The selection of specific counterions suitable for such purposes would be apparent to those skilled in the art.

The metal nanorods produced by the methods described herein have been shown to have various lengths but are particularly suited for rods possessing a medium aspect ratio and significant length (e.g., rods that are from about 5 to about 15 nm wide and from about 30 to about 100 nm in length). In certain embodiments, a variety of asymmetric and symmetric surfactants having tail lengths from about 12 to about 16 and spacer lengths from about 4 to about 10 have been used to grow gold nanorods. By varying the tail and spacer length a variety of gold nanorods have been grown with surface plasmon resonances from about 650 to about 950 nm.

In view of the above, it will be understood that, in embodiments, control of the amount of metal seeds is not required for growth to occur. The growth of the metal nanorods is, in embodiments, spacer length dependent, allowing bi-lateral control of the size of the metal nanoparticles. Thus, the gemini surfactants may be referred to as "shape-directing surfactants." Further, the metal seeds, like the metal nanorods, can successfully be grown without the use of CTAB. Additionally, the metal nanorods can be grown with a shorter surfactant carbon chain length tail compared to the chain length of CTAB.

The method described herein may be scaled-up. For example, the method may be scaled-up by increasing the total volume of the mixture, whereby the proportion of reactants such as surfactant(s) and source of metal cations is substantially maintained in comparison to the mixture at a lower volume. In embodiments, the total volume at a lower scale may be about 5 ml to about 500 ml and the scale-up volume may be up to about 4 L The proportion of reactants at the lower scale may be similar to the proportion at the higher scale-up. In certain embodiments, the amount of metal cations may be adjusted further. With respect to the temperature, the temperature may be maintained. In typical scale-ups, the temperature may be lower than the temperature used in the lower volume to provide a similar or higher abundance of metal nanorods. The adjustment may depend on the desired nanorod size, in some embodiments, the reaction temperature of the scale-up is about to about 3° C. lower than the temperature used at a lower volume or is about 1° C. to about 2° C. lower than the temperature used at a lower volume. In any event, one skilled in the art would understand how to adjust the conditions and reactants in the methods described herein to achieve scale-up.

Methods of Forming Metal Seeds

In other embodiments, methods of forming metal seeds are provided, in which a gemini surfactant solution, a source of metal cations, and a reducing agent are combined. This method provides a source of metal seeds that are free of cytotoxic surfactant, such as CTAB. Suitable amounts are used. Similar amounts as that described above is used. In embodiments, the gemini surfactant solution is used in an amount of from about 1.0 wt % to about 2 wt %, from about 1.5 wt % to about 2 wt %, from about 1.7 wt % to about 2 wt %, or from about 1.75 wt % to about 1.95 wt %, based on the total weight of the mixture.

Methods of Separating Metal Nanorods

In embodiments, the methods described herein provide a more simplified purification process for the metal nanorods and, thus, a combined production and purification process is contemplated herein. By selecting surfactants with different solubilities and treating the metal nanorod solution with additional surfactants), the resultant mixture separates with the metal nanorods of the dominant size/shape comprising the majority of particles in one layer and relatively pure.

To obtain metal nanorods of a particular size range, i.e., to obtain an appropriate number of metal nanorods of a predetermined specific length, separation of the desired nanorods from other nanoparticles ("impurities") is often accomplished by the use of various filtration techniques and separation techniques based on the differential rate of settling of the metal nanorods of the desired length from the "impurities." These techniques are known by those skilled in the art to be both time consuming, and relatively inefficient at complete initial separation. In the preparation of the metal nanorods described herein, it was found that metal nanorods of the desired embodiments were separated from other small particles using surfactant phase separation methodologies where a homogenized metal sol was spontaneously phase separated by changing the ionic strength of the solution. More specifically, using both inorganic and amphiphilic organic salts, it is possible to perform an efficient separation of the desired metal nanoparticle from the "impurities" either with the use of a concentrated solution of surfactant known as a coacervate or a second surfactant containing solution that can interact preferentially with the metal nanoparticle surface in the presence of an effective amount of organic or inorganic salt(s).

In another embodiment, the method of purification of metal nanorods involves addition of metal salt to a metal nanorod solution. The method may further comprise surfactant phase separation upon addition of a metal salt and a phase separating surfactant to allow certain metal nanoparticle geometries (e.g. nanorods) to preferentially separate into the surfactant rich phase of phase separating surfactant-containing layers. The metal salt may be selected from alkali metal salts, alkaline earth metal salts, transition metal salts, and combinations thereof. Typically, the salt is an alkali metal salt such as sodium chloride. The amount of metal salt may range from about 0.2 to about 5% (w/w) based on nanorod solution temperature, more typically, from about 1 to about 1.5% (w/w). The method may be repeated multiple times. Any suitable temperatures may be used, typical temperatures used are from about 4° C. to about 22° C.

For the purification of the metal nanorod-containing solution using coacervates, the mixture containing the metal nanorods may be equilibrated for a period of time. For example, the mixture may be equilibrated to a temperature of about 25° C. for about 1 hour or more. Once equilibrated, an effective concentration of a salt solution that induces coacervates with the surfactant in question, is added to the equilibrated mixture, spontaneously forming a coacervate phase containing the metal nanorods. The salt solution may, for example, comprise a hydrotrope.

In an embodiment, a method of purifying metal nanorods from a metal nanorod-containing solution comprises combining the metal nanorod-containing solution with a gemini surfactant and a salt, wherein the gemini surfactant and salt form a coacervate; and separating the resultant coacervate, wherein the coacervate contains the metal nanorods.

In another embodiment, a method of purification of metal nanorods comprises centrifuging the metal nanoparticle solution, separating a solvent layer from a resultant metal nanoparticle pellet, adding nanopure water, and centrifuging at suitable ref values. The volume of nanopure water for dissolution may be about 4% to about 100% of the original solvent layer volume. The dissolution temperature prior to centrifugation may be from about 30° C. to about 99° C. In a specific embodiment, the centrifugation involves about two ten minute spins at about 25° C. and at about 300 to about 3550 r.c.f. at 25° C. depending on the dilution of the nanorod pellet.

Figure 26:
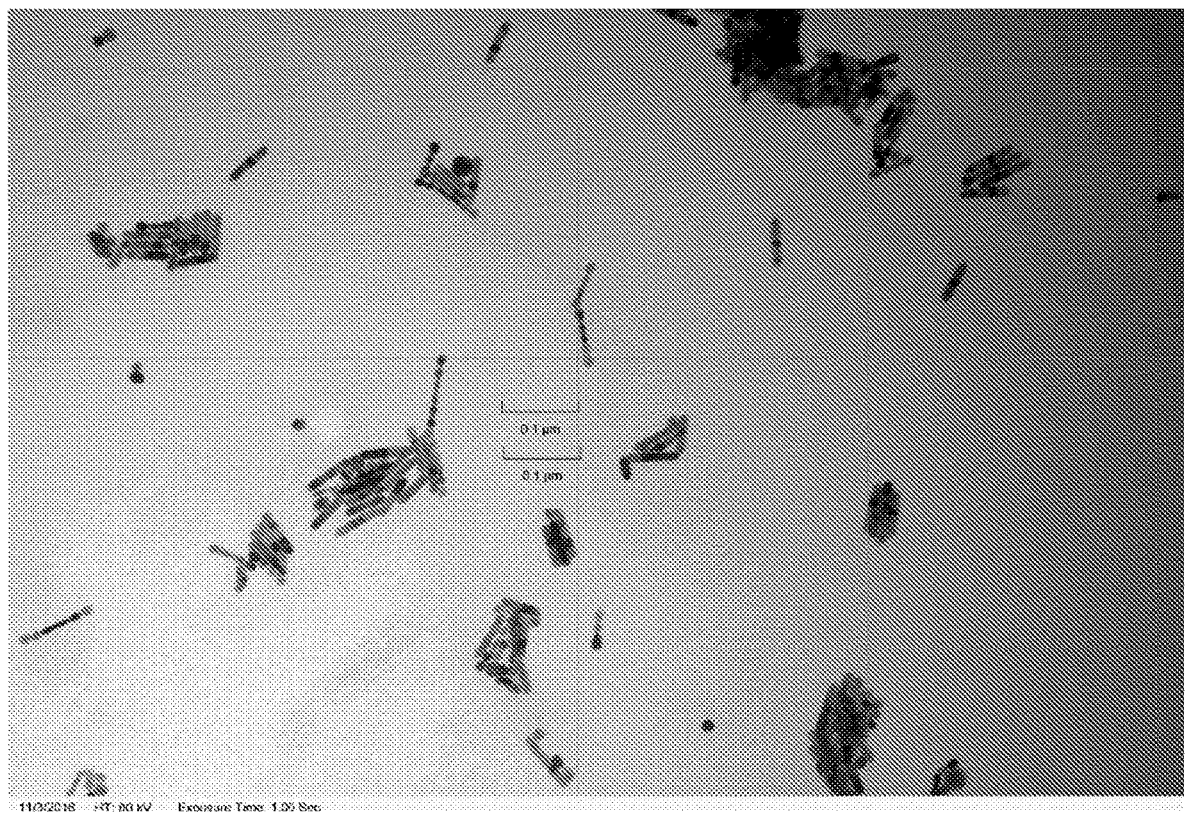
FIG. 26 shows symmetrically etched gold nanorods.

The method may be utilized to control at least one of the length and reshaping. For example, by controlling the temperature these properties may be modified. In an embodiment, a method of converting longer metal nanorods to shorter metal nanorods, reshaping (e.g. etching of the surface) is provided. In certain embodiments, the method includes heating the metal nanorod solution to a suitable temperature to reduce the length of the nanorods. The temperatures may range from about 30° C. to about 89° C. and in pH ranges from about 4 to about 9. The presence of a co-surfactant, or a co-solvent (such as amine or alcohol), or an oxidizing agent (such as $H_2O_2$) may be used to accelerate the process. The heating time may range from about 15 minutes to about 12 hours in the form of cycles of low to high temperature with no waiting time in between. Centrifugation can be used to eliminate impurities produced during reshaping (typically, one or two centrifuge cycles with a time duration of about ten minutes at about 25° C. and at about 300 to about 3550 r.c.f.). Additional centrifuge cycles may be necessary and the number of centrifuge cycles, duration, and temperature can be determined by one skilled in the art. Any axial length may be achieved in a reshaping and therefore, any longitudinal and transverse absorption in principle can be achieved using this reshaping method. This methodology is in essence a much simpler and improved method for purification, for example, permits the rods to be as monodispersed as possible. With centrifugation, there may be a broad range of nanorod lengths. This method is able to produce narrow peak ranges in the UV with a lower number of centrifugation steps in comparison to known methods. In an embodiment, symmetrically etched metal nanorods can be made from this method (see FIG. 26). The nanorods appear as four connected spheres (e.g. symmetrically etched nanorods having a multi-harmonic shape).

Methods of Making Metal Nanorods with Solubilizate in Bilayer

There is also provided methods of loading solubilizate(s) into a metal nanorod surfactant bilayer.

In an embodiment, the method comprises addition of at least one solubilizate to a metal nanorod solution and allowing the solution to equilibrate for a period of time. For example, the mixture may be equilibrated to a temperature of about 4° C. to about 25° C. for at least about 1 hour.

Examples of solubilizates may be any suitable molecule that is partially or completely water soluble. The solubilizates may be bio-molecules such as proteins, nucleic acids, polysaccharides, glycoproteins, flavonoids, vitamins, antioxidants, aromatic acids, amino acids, monohydroxybenzoic acid, monosaccharides, disaccharides, bile salt, and nucleotides. Other examples include gelatin, beta casein, streptavidin, metal nanorod-streptavidin conjugate, bovine serum albumin, quercetin, epigallocatechin gallat, Curcumin, curcumin, glutathione, oxy/deoxy cholic acid, anthranilic acid, cinnamic acid, biotin, and p-hydroxybenzoic acid.

The amount of solubilizates that may be adsorbed in the surfactant bilayer of the metal nanoparticles may range from about 0.03% to about 20% (w/w); 0.1% to about 20% (w/w); 0.03% to about 10% (w/w); 0.03% to about 5% (w/w); 0.1% to about 15% (w/w); or 0.1% to about 10% (w/w) of based on total weight of the metal nanorod solution.

Figure 24:
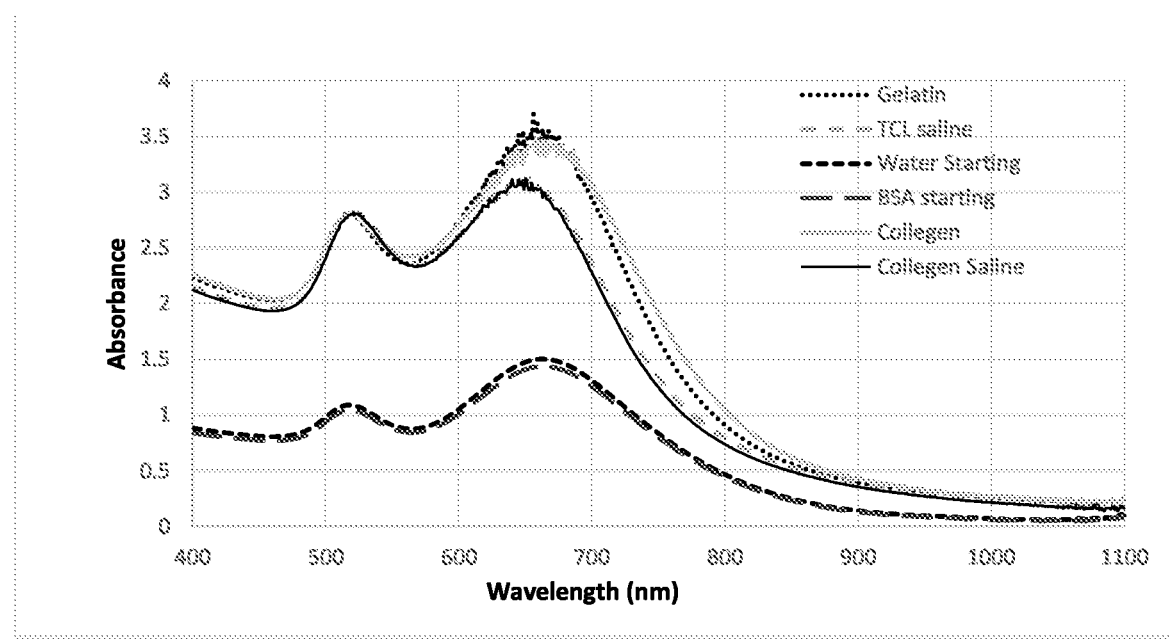
FIG. 24 shows UV-Vis traces for gold nanorod wrapped in different biopolymers.

In another method, the metal nanorods having a surfactant bilayer may be wrapped in a polymer (e.g. FIG. 24). In embodiments, the wrapping polymers may include proteins, gelatin, bovine serum albumin, polystyrene sulfonate, polyethylene oxides, thiolated polyethylene oxides, thiolated polyethylene oxides with terminating carboxylic acid functionalities, thiolated polyethylene oxides with terminating amine acid functionalities, and combinations thereof.

In an embodiment, the wrapping polymer may form covalent or non-covalent bonds with other polymers, proteins, etc. In certain embodiments, the carboxylic ending of thiolated polyethylene oxides is bound to protein(s), polypeptide(s), antibodie(s), antibody fragment(s), IgG class of antibody, a polyclonal antibody, a monoclonal antibody, and combinations thereof. In another embodiment, the amine ending thiolated polyethylene oxide is bound to protein(s), polypeptide(s), antibodie(s), antibody fragment(s), IgG class of antibody, a polyclonal antibody, a monoclonal antibody, and combinations thereof. Such covalently bounded bioconjugates may be formed, for example, from any metal nanorods described herein, a polymer, and, for example, an antibody, protein(s), polypeptide(s), antibodie(s), antibody fragment(s), IgG class of antibody, a polyclonal antibody, a monoclonal antibody.

In an embodiment, single or double stranded nucleic acid may be tethered to metal nanorods with metal-thiol bonds. In an embodiment, an oligonucleotide may be tethered to metal nanorods with metal-thiol bonds.

Methods of Making Metal Nanorods with Capping

Metal nanorods comprising a variety of capping agents and bio-conjugation are described. In an embodiment, methods of capping a metal nanorod with a non-surfactant involve first removal of a solvent or excess surfactant from the metal nanorod solution followed by addition of an aqueous solution of capping agent(s). In typical embodiments, about 95% to about 98% of the solvent is removed and a similar quantity of the aqueous solution of the new capping agent(s) is added.

In a more specific embodiment, the method comprises removal of about 95% to about 98% of solvent from the metal nanorod solution, followed by the addition of a similar amount of an aqueous solution of a first capping agent (e.g. an ionic polymer, typically an anionic polymer), and allowing the solution to equilibrate for a period of time.

For example, the mixture may be equilibrated to a temperature of about 4° C. to about 25° C. for at least about 1 hour. Then removing about 95% to about 98% of resultant solvent from the resultant nanoparticle pellets, for example, by using a centrifugal method, and additional dispersion of the resultant metal nanoparticle pellets into an aqueous solution of a second capping agent (e.g. same or different from first capping agent).

After capping, in embodiments, the metal nanorods are positively charged and may have a charge of from about +5 to about +40 mV. In other embodiments, the metal nanorods are negatively charged and may have a charge of from about −5 to about −55 mV.

In embodiments, the capping agent of metal nanorods in a colloidal solution form may be a mixture of surfactant and a thiolated polymer (polyethylene glycol of mwt, of about 1000 kDa to about 5000 kDa). In an embodiment, the capping agent of metal nanorods in a colloidal solution form may be a mixture of surfactant from a surfactant solution and a thiolated polymer (polyethylene glycol of mwt. of about 1000 kDa to about 5000 kDa). In an embodiment, the capping agent of metal nanorods may be a mixture of surfactant, a co-surfactant, and small biomolecules. The small biomolecules may be selected from a general class of flavonoids, antioxidants, aromatic acids, amino adds, monohydroxybenzoic acid, monosaccharides, disaccharides, bile salt, nucleotides, or combinations thereof. In an embodiment, co-capping agent(s) may be added such as quercetin, epigallocatechin gallate, curcumin, glutathione, ascorbic acid, citric acid, anthranilic acid, cinnamic acid, bile acid, and p-hydroxybenzoic acid, metal anionic salts of biological acid(s), or combinations thereof.

Methods of Making Metal Nanorods with Solvent Exchanged with a Surfactant Composition In an embodiment, re-dispersion of metal nanorods into more stable media is described. The method may comprise extracting the metal nanorods and re-dispersing them in a surfactant composition. The surfactant composition comprises a stabilizing agent. For example, metal nanorods are extracted from reaction surfactants using a centrifuge (from about 1000 to about 100000 r.c.f.) for a time period of about 1 to about 60 min (typically from about 10 to about 15 min), followed by re-dispersion (optionally with heating and/or ultra-sonication) into a surfactant composition with a pH adjuster. The pH may range from about 4 to about 8 or more typically, from about 4 to about 6 and most typically, about 4.5 to about 5.5. The surfactant composition may comprise any suitable stabilizing agent that provides stability to the metal nanorod solution.

The surfactant composition may comprise surfactants used in making the original metal nanorad solution and/or the surfactants may be different. In embodiments, the surfactant composition comprises Ammonyx MO and glycine betaine surfactants such as, and without being limited thereto, those with a chain length from about 8 to about 14 carbons. In other embodiments, the surfactant composition comprises at least one alkyl glycine surfactants (typically having a chain length that is less than the substrate surfactant(s) used in the method for making the metal nanorods) and at least one alkyl N-oxide surfactant. Alkyl N-oxide surfactants can be any of the suitable N-oxide amphoteric surfactants described herein (e.g. alkyl dimethyl amine oxide surfactant). In other embodiments, acid or base is used to adjust the pH of solution and hence, alter the charges of the head group comprising the surfactant bilayer of the nanorods.

Figure 23:
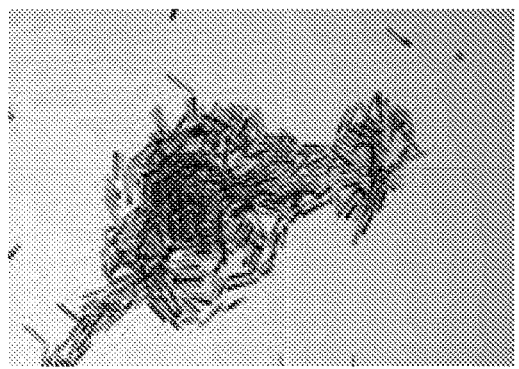
FIG. 23 shows TEM image comparing original gold nanorod solution (A) and re-dispersed gold nanorod solution (B).
Figure 23:

In other embodiments, FIG. 23 shows a comparison between the original gold nanorod solutions (A) vs. the re-dispersed gold nanorods surfactant composition (B) with an improved dispersion ability, which was qualitatively evaluated using TEM. The types of surfactants useful in this purification step will be readily apparent to those skilled in the art based on the description herein.

Uses of Metal Nanorods

The metal nanorods described herein find use in industry, cosmetics, medicine, electronics, and so on. Specific application areas are those where the plasmonic properties of the metal nanorods can be utilized to achieve primary goal or utilized to achieve secondary goal. In typical embodiments, the metal nanorods described herein find use in treating cancer, diagnosis, and imaging.

For example, the metal nanorods described herein may be suitable materials for a coating composition, a coating, a film, a wiring material, an electrode material, a catalyst, a colorant, a cosmetic, a near-infrared absorber, an anti-counterfeit ink, or an electromagnetic shielding material. In addition, the metal nanorods described herein may be used for materials for a surface enhanced fluorescent sensor, a biomarker and a nano-waveguide.

Specifically, a solution in which the metal nanorods described herein are dispersed may be used as a component of an anti-counterfeit ink. For the anti-counterfeit ink, a characteristic of absorbing specific wavelengths, a scattering light or a fluorescence of the metal nanorods is used for a detection method. For example, since the gold nanorods absorb specific wavelengths, such as in a wavelength region from about 600 nm to about 2,100 nm, a detection wavelength may be set to this range. By setting the specific absorption wavelength in the near-infrared region of 760 nm to 1,500 nm, an invisible ink may be obtained which is transparent in a visible light region. Since the invisible ink is identifiable in the near-infrared region, it may be used as the anti-counterfeit ink. By using the metal nanorods described herein in this ink, a film coated with the ink may have properties of weather resistance, heat resistance and/or chemical resistance. Furthermore, for a dispersant used for a surface treatment of the metal nanorods, a dispersant compatible with a solvent to be used can be selected. Therefore, the solvent of the anti-counterfeit ink can be appropriately selected by a skilled person.

Also, the metal nanorods described herein may be used as a colorant for a cosmetic and a color indicator for immunoassay applications. When the metal nanorods described herein are dispersed in an oil-based base material, they are difficult/impossible to detect with the naked eye. Therefore, a coating having high transparency may be obtained. Furthermore, by adding a small quantity of the metal nanorods described herein to the cosmetic, a strong tinting strength and a high color saturation may be realized.

In addition, a conductive paste can be formulated containing the metal nanorods; this pasted can be used as a wiring material or an electrode material. This conductive paste may be applied onto an insulating base material by printing and then dried or baked. Thereby, a wiring diagram or an electrode may be formed which may have properties of conductivity and migration resistance. For this conductive paste, for example, a paste containing 1 to 20 parts by weight of a binder relative to 100 parts by weight of the metal nanorods described herein may be used.

Furthermore, the metal nanorods described herein may be secured on the surface of the glass substrate at high density to enhance infrared ray adsorption or fluorescence emission for Surface Enhanced Raman Spectroscopy (SERS) and Surface Enhanced Fluorescence Spectroscopy (SEFS), respectively. The metal nanorods described herein may be suitable for a sensor material based upon the SERS and/or SEFS. For example, since the gold nanorods described herein may have an absorption region with a strong absorbance in a wavelength region from about 550 nm to about 800 nm, a sensor material formed by securing gold nanorods treated with a silane agent having a thiol end (such as, 3-mercaptopropyltrimethylsilane) on a glass substrate at high density may be suitable for an SEFS spectroscopy sensor for which a fluorescent substance (for example, rhodamine series fluorescence pigments) emitting fluorescence in that wavelength region is used as a marker.

Furthermore, when the metal nanorods described herein are one-dimensionally arranged at high density and regularity, an interaction of a near-field light generated in a vicinity of nano-particles enables light transmission between the particles. Thereby, a nano-waveguide can be obtained which may suitable for a one-dimensional waveguide. For example, the nano-waveguide may be obtained by the following method: Firstly, the metal nanorods are one-dimensionally arranged using a manipulator, such as an atomic force microscope (AFM) or a scanning tunneling microscope (STM). Next, luminous nano-particles (such as zinc oxide or CdTe) are fixed at an end of the one-dimensionally arranged metal nanorods, and an optical fiber sensor of the near-field microscope is positioned at an opposite end of the arrangement. By forming such a structure, a nano-waveguide may be obtained.

In addition, the metal nanorods described herein may be used as a biomarker responding to near infrared rays. For example, near infrared rays with 750 nm to 1,100 nm wavelength are not substantially absorbed by organic substances. However, the gold nanorods described herein may have a particular absorption characteristic in the wavelength region from about 750 nm to about 1,100 nm depending on the aspect ratio. Therefore, in the case in which a particular site of a living body is stained with the gold nanorods, when the near infrared rays are radiated, the near infrared rays are absorbed by that site and, thereby, the site can be identified. Therefore, with regard to a thick biomaterial which cannot easily be measured by a conventional method involving a suspension or a coloration of the biomaterial, it may be possible to observe an optional portion coloured by the metal nanorods described herein.

The metal nanorods described herein may be utilized in a lateral flow assay device or method. For example, in lateral flow strip immune assays or vertical flow immune assays. Such assays may include a nitrocellulose membrane. The metal nanorod and an antibody conjugate may be used in a lateral flow assay. The metal nanorod and antibody conjugate may flow on the nitrocellulose membrane. In an embodiment, the metal nanorod and antibody conjugate is capable of capturing a bio-marker from a test solution. For example, a metal nanorod and antibody conjugate-biomarker complex can be formed. In an embodiment, the metal nanorod and antibody conjugate-biomarker complex may be captured by primary antibodies deposited as a test line on a nitrocellulose membrane.

Specifically, a living body may be stained using the metal nanorods described herein. The metal nanorods may be used uncoated or, optionally, they may be coated with a compound having high biocompatibility, for example, polyethylene glycol, phospholipid, sugar chains or antibodies. The uncoated metal nanorods or metal nanorods coated with a biocompatible compound such as polyethylene glycol or phospholipid may be suitable for uniformly staining a living body or portion thereof without localizing at a particular organ or tissue. On the other hand, certain targeting molecules such as sugar chains or antibodies may accumulate in a specific organ or tissue and may therefore be suitable for staining that specific organ or tissue.

Thus, the metal nanorods described herein may be administered to a cell or tissue using targeting schemes involving specific chemical interactions (e.g., antigen-antibody binding, etc.) or may consist of the simple delivery of the metal nanorods to the desired area, typically by the delivery of a pharmaceutical composition comprising the metal nanorods. The direction or targeting of the therapy may be to the surface of the subject cells and/or tissue, or it may be to other, interior sites.

The above disclosure generally describes the present invention. A more complete understanding can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Single-Pot Reaction and Production of Gold Nanorods

Figure 2:
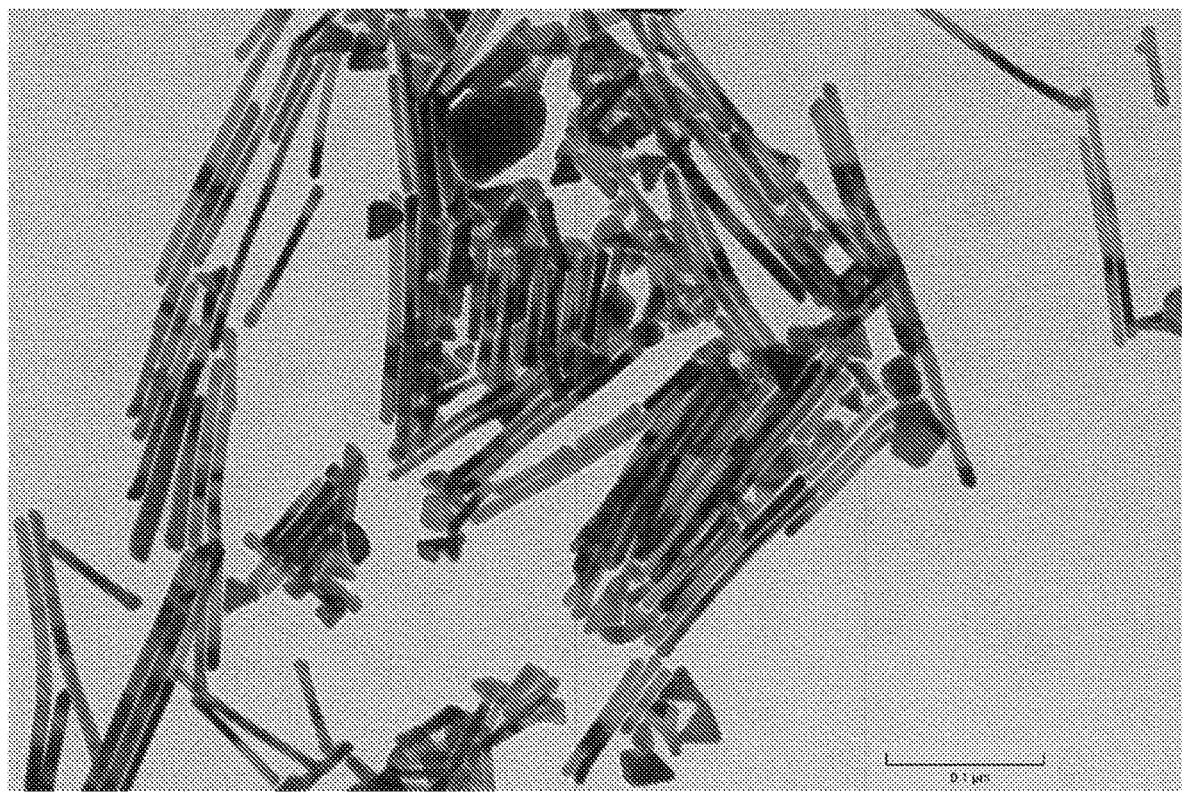
FIG. 2 shows a Transmission Electron Microscopy (TEM) image of gold nanorods produced in a surfactant mixture of 0.30 g of stearyl betaine and 0.080 g Ammonyx™ MO.
Figure 3:
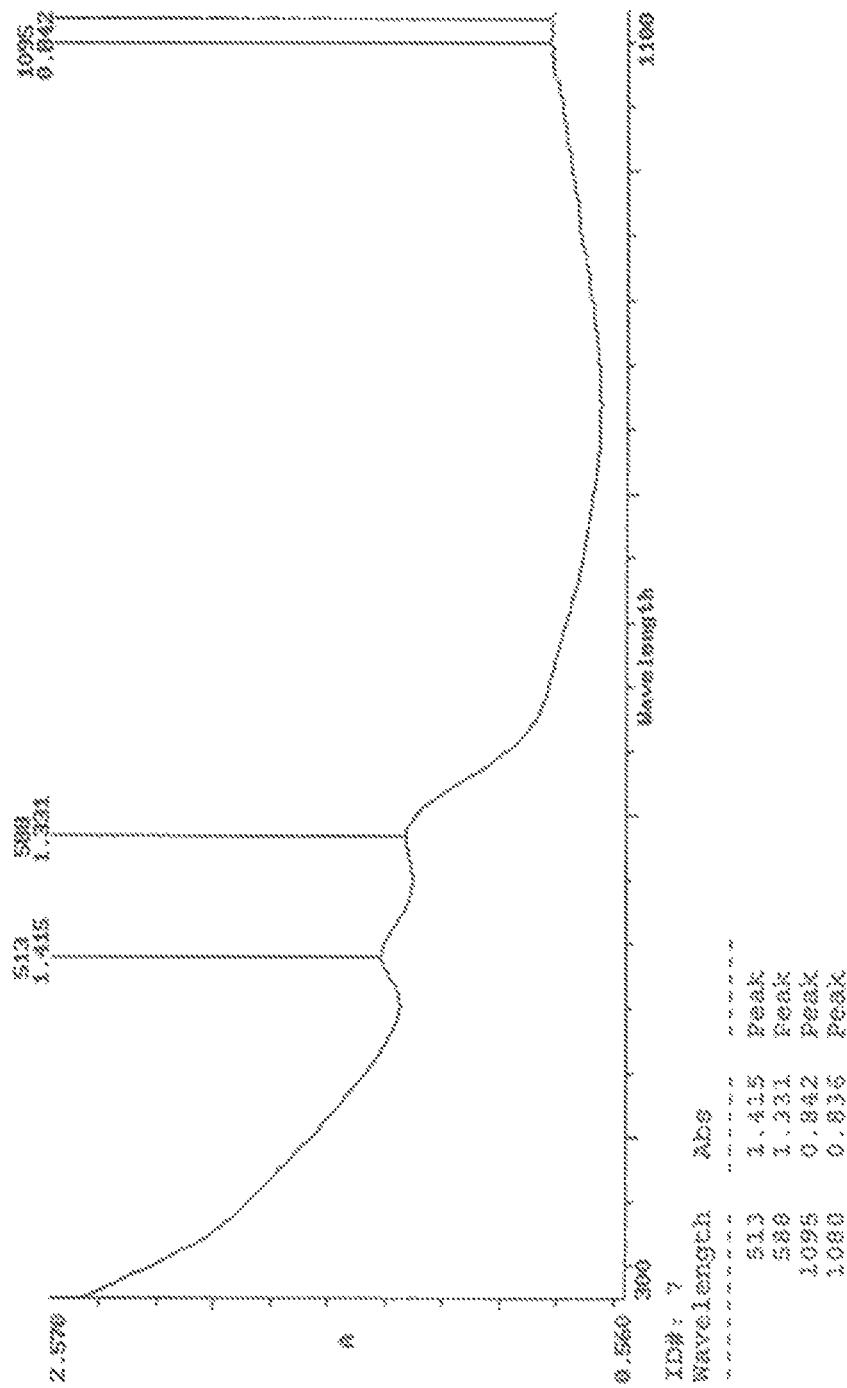
FIG. 3 shows the UV-Vis spectra of gold nanorods produced in a surfactant mixture of 0.30 g of stearyl betaine and 0.080 g Ammonyx™ MO.
Figure 4:
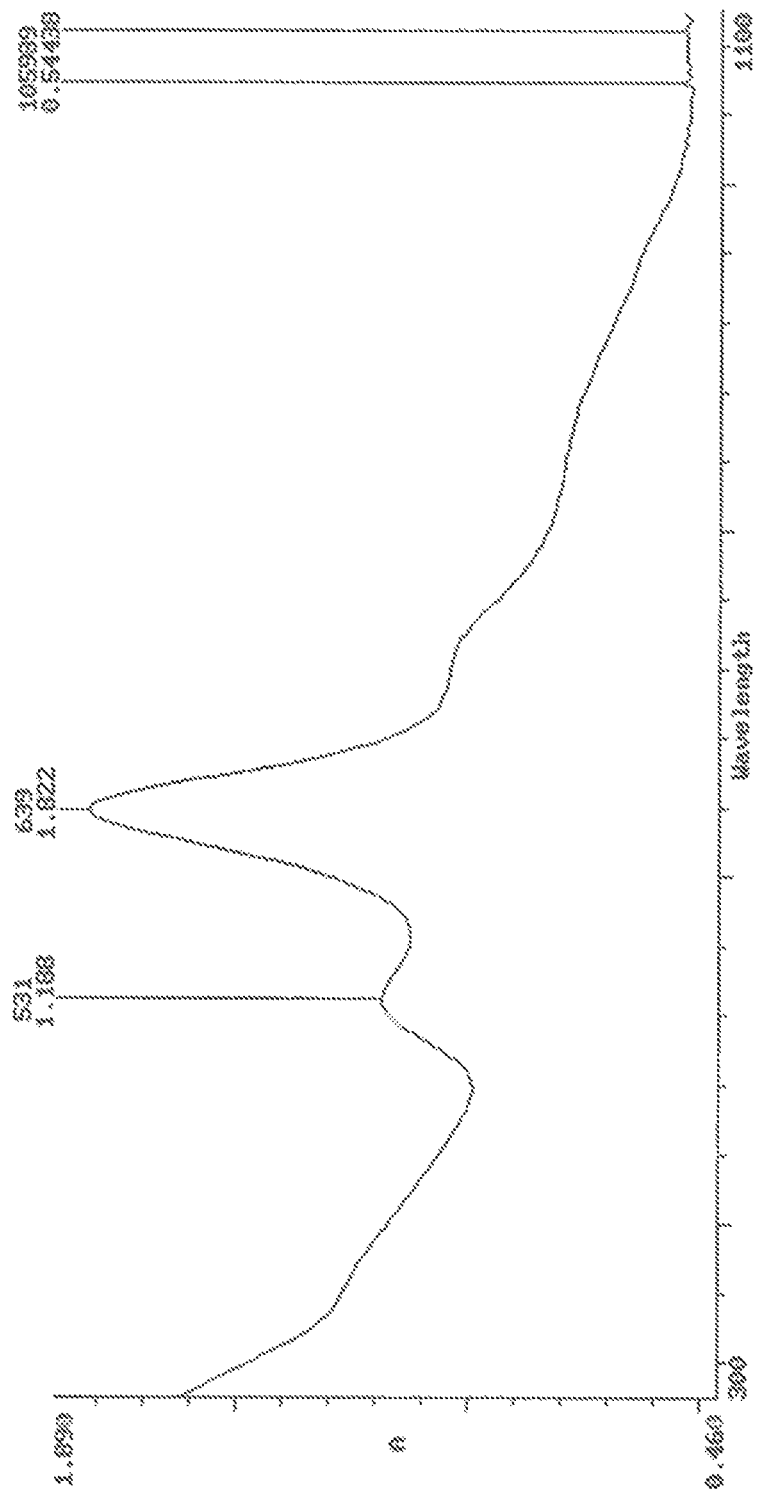
FIG. 4 shows the UV-Vis spectra of gold nanorods produced in a surfactant mixture of 0.30 g stearyl betaine and 0.05 g Ammonyx™ MO.
Figure 5:
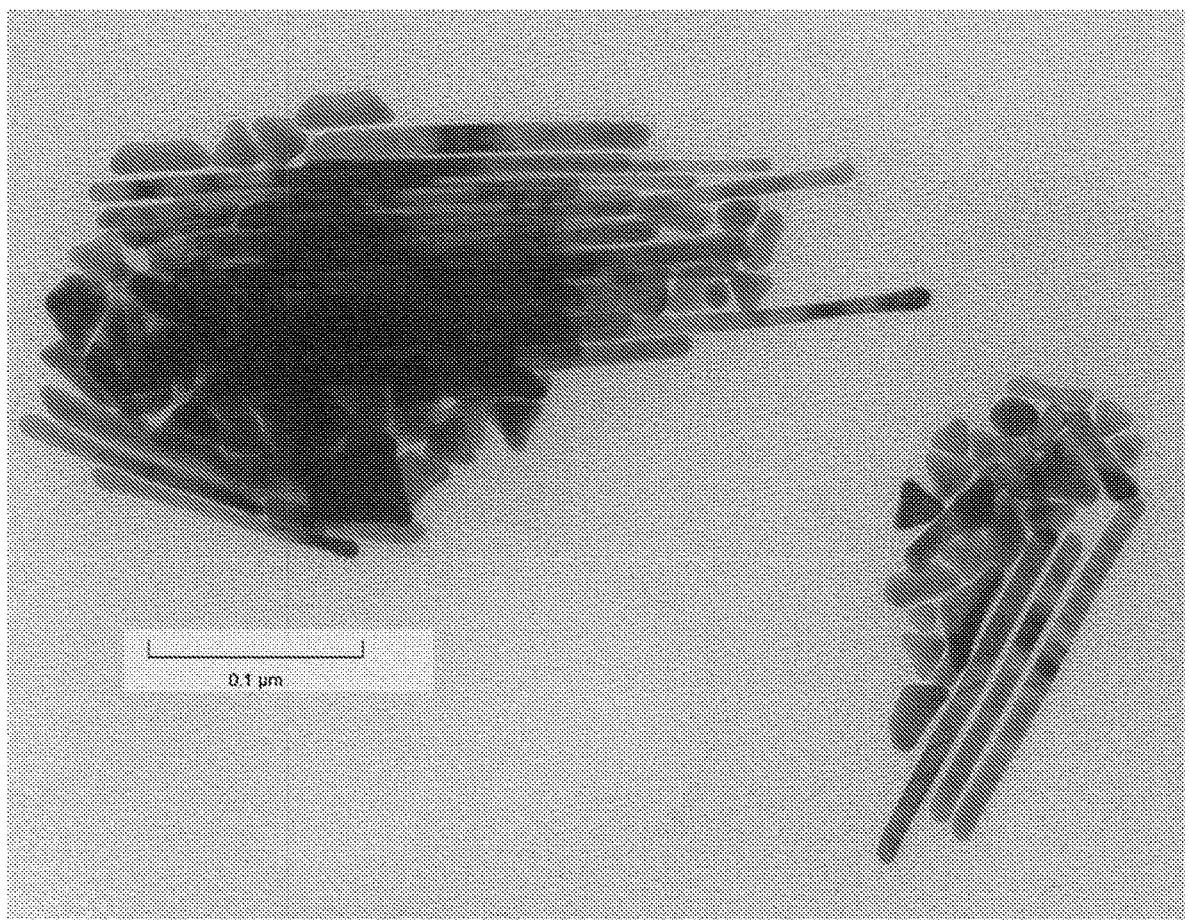
FIG. 5 shows a TEM image of gold nanorods produced in a surfactant mixture of 0.30 g stearyl betaine and 0.05 g Ammonyx™ MO.
Figure 6:
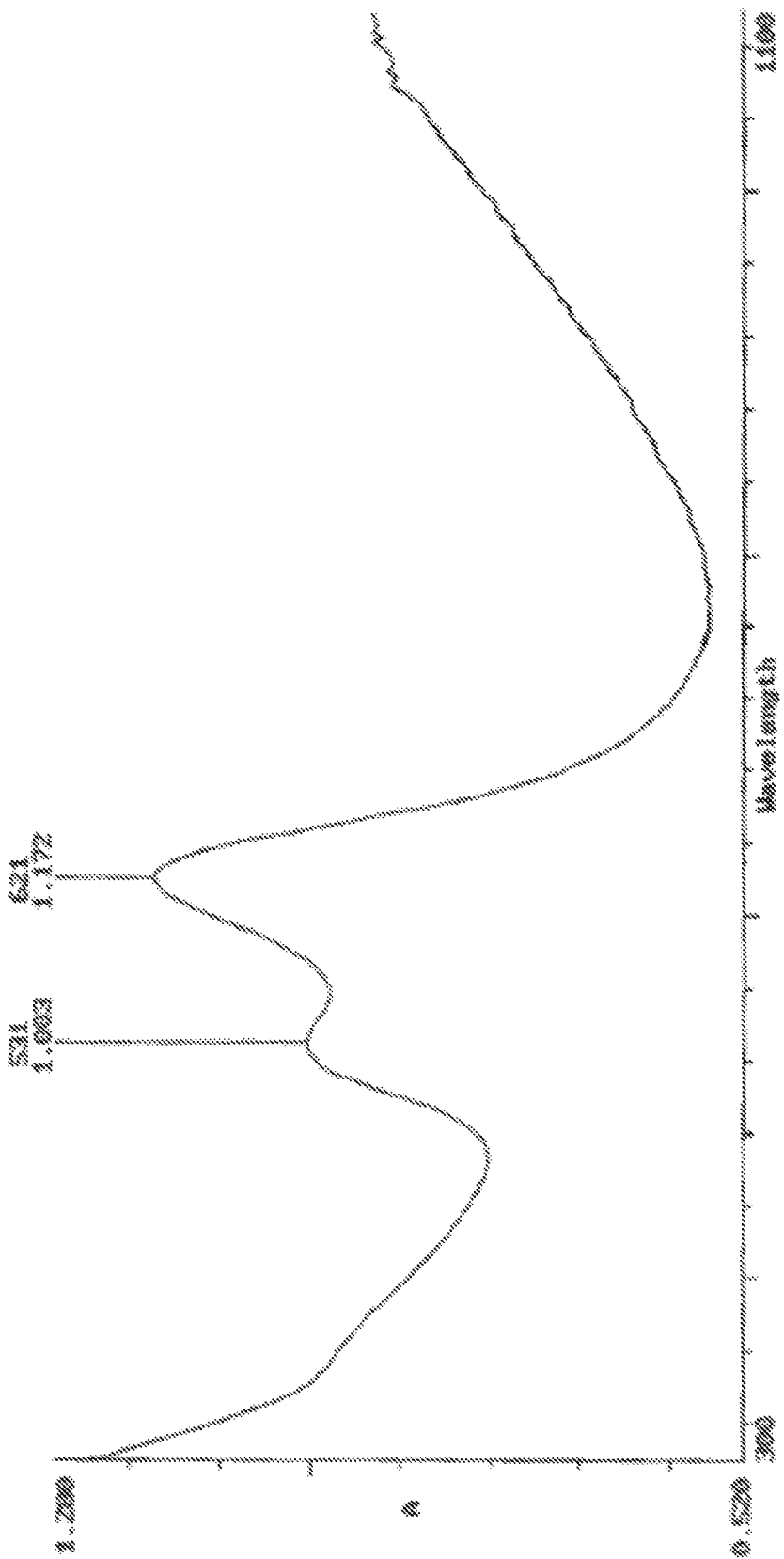
FIG. 6 shows the UV-Vis spectra of gold nanorods produced in a surfactant mixture of 0.35 g stearyl betaine and 0.45 g Ammonyx™ MO.
Figure 7:
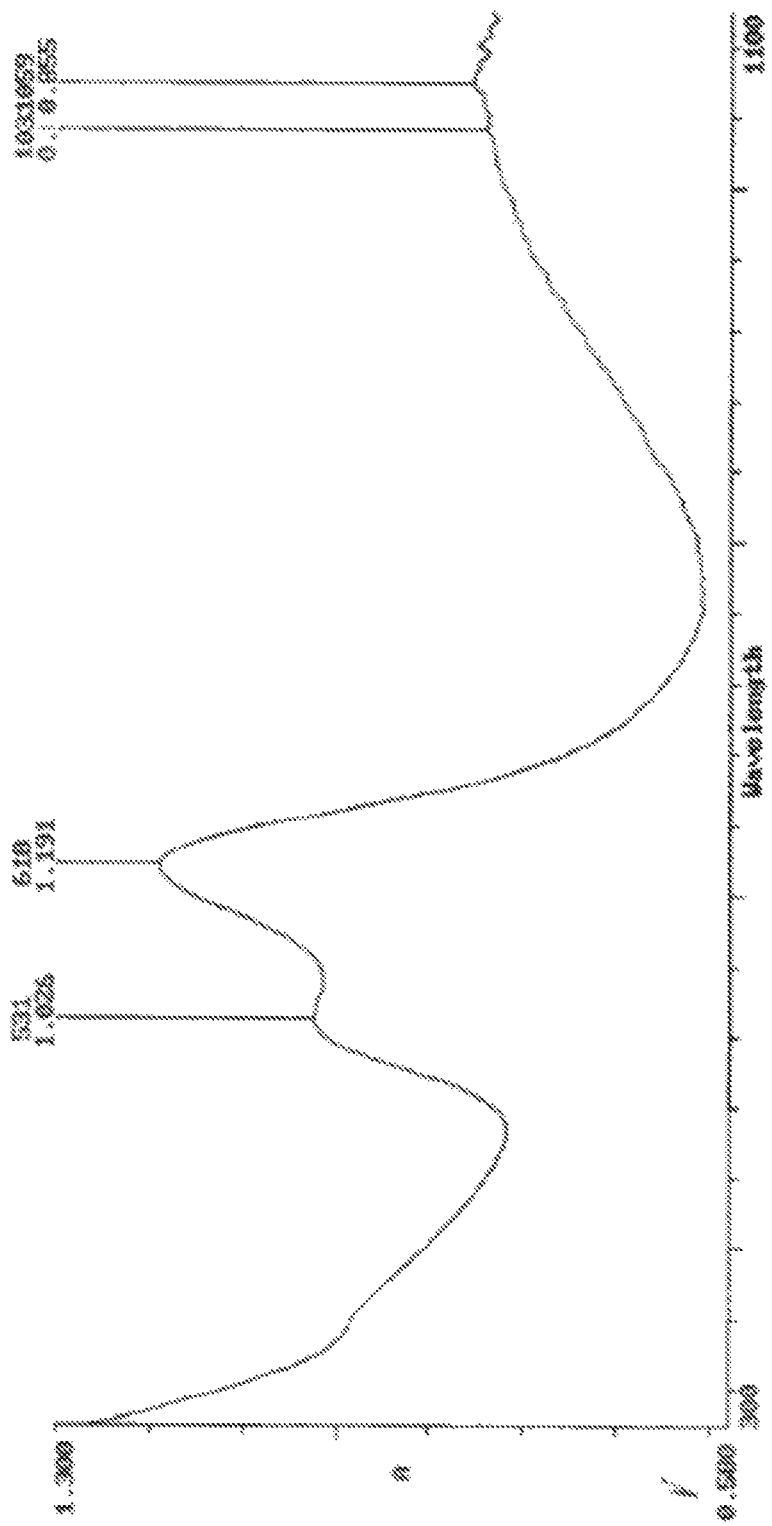
FIG. 7 shows the UV-Vis spectra of gold nanorods produced in a surfactant mixture of 0.30 g stearyl betaine and 0.50 g Ammonyx™ MO.
Figure 8:
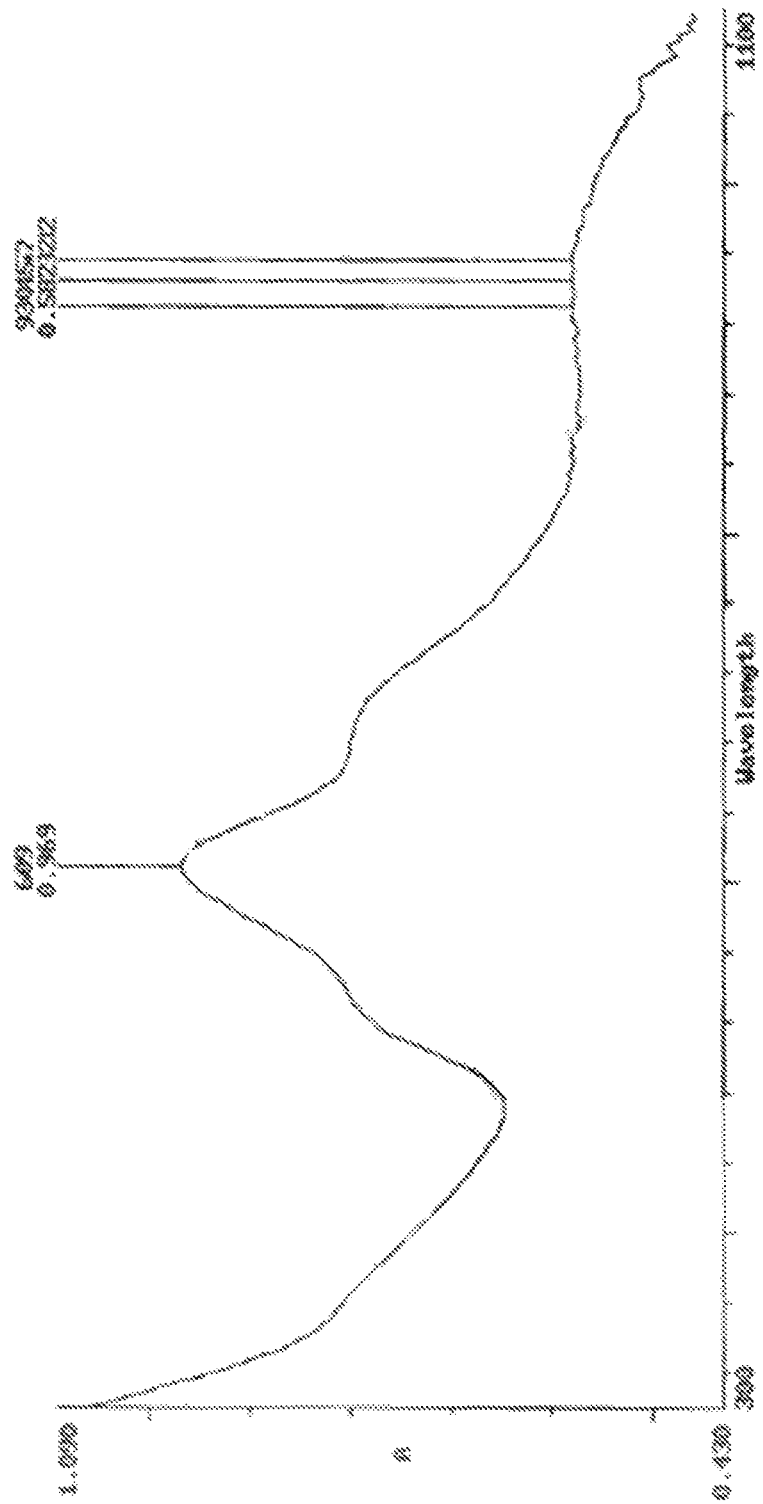
FIG. 8 shows the UV-Vis spectra of gold nanorods produced in a surfactant mixture of 0.15 g stearyl betaine and 0.45 g Ammonyx™ MO.
Figure 9:
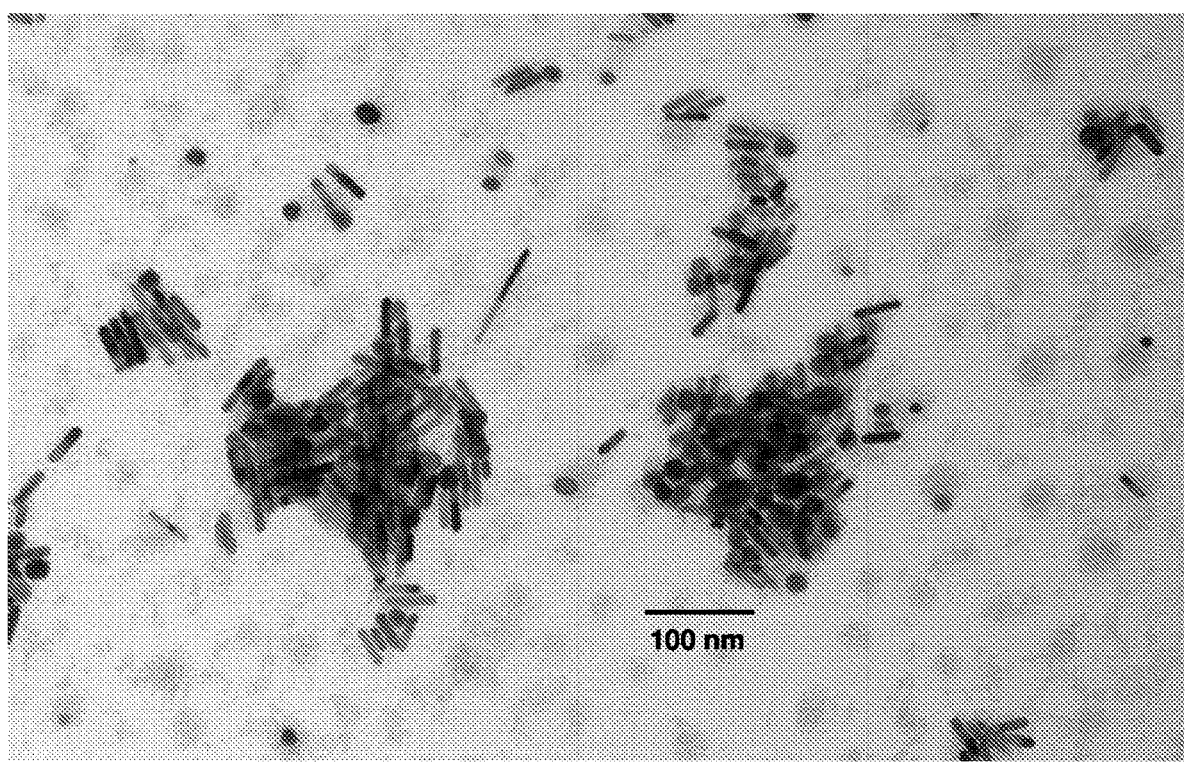
FIG. 9 shows a Transmission Electron Microscopy (TEM) image of gold nanorods produced with a 12-carbon gemini surfactant.
Figure 10:
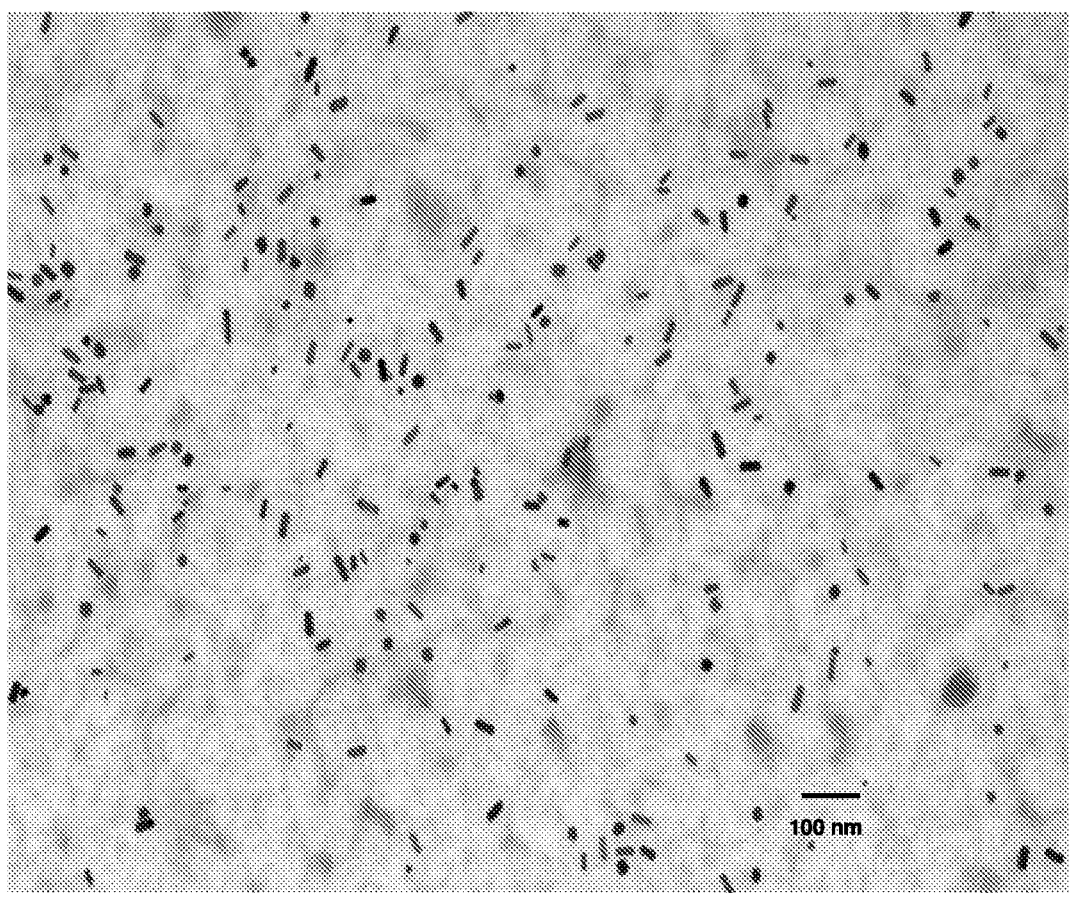
FIG. 10 shows a Transmission Electron Microscopy (TEM) image of gold nanorods produced with a 14-carbon gemini surfactant.
Figure 11:
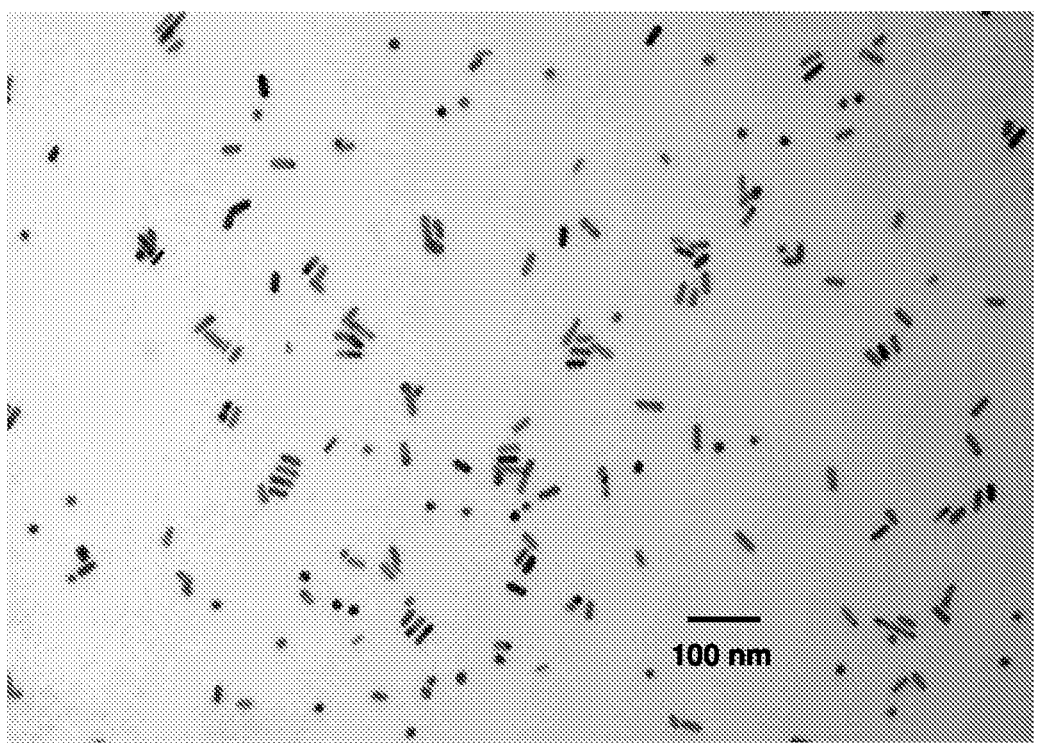
FIG. 11 shows a Transmission Electron Microscopy (TEM) image of gold nanorods produced with a 16-carbon gemini surfactant.
Figure 12:
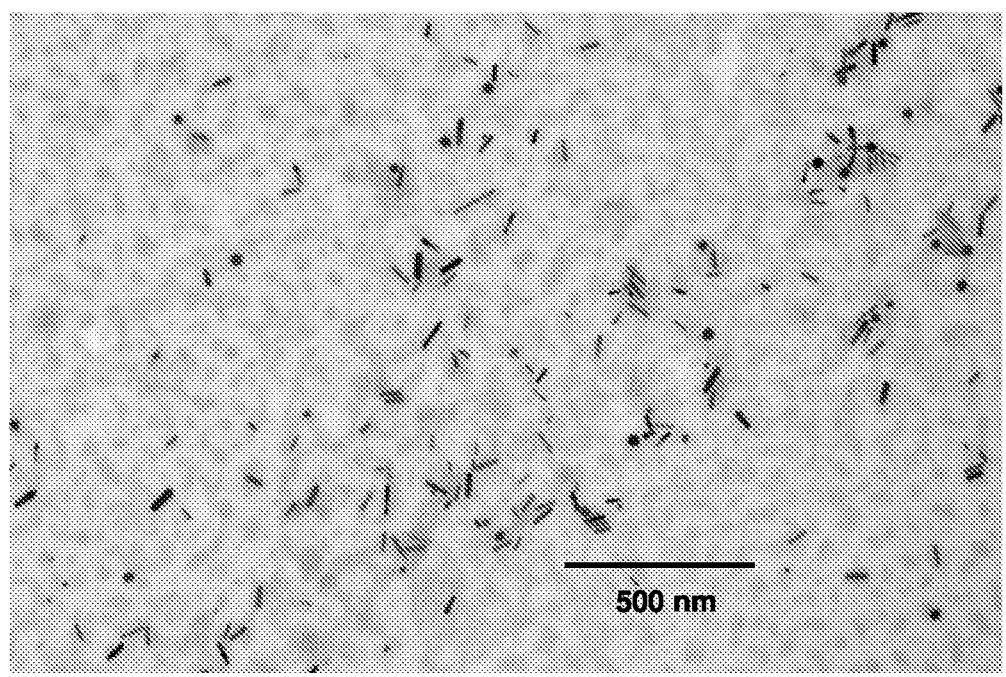
FIG. 12 shows a Transmission Electron Microscopy (TEM) image of gold nanorods produced with an 18-carbon gemini surfactant.
Figure 13:
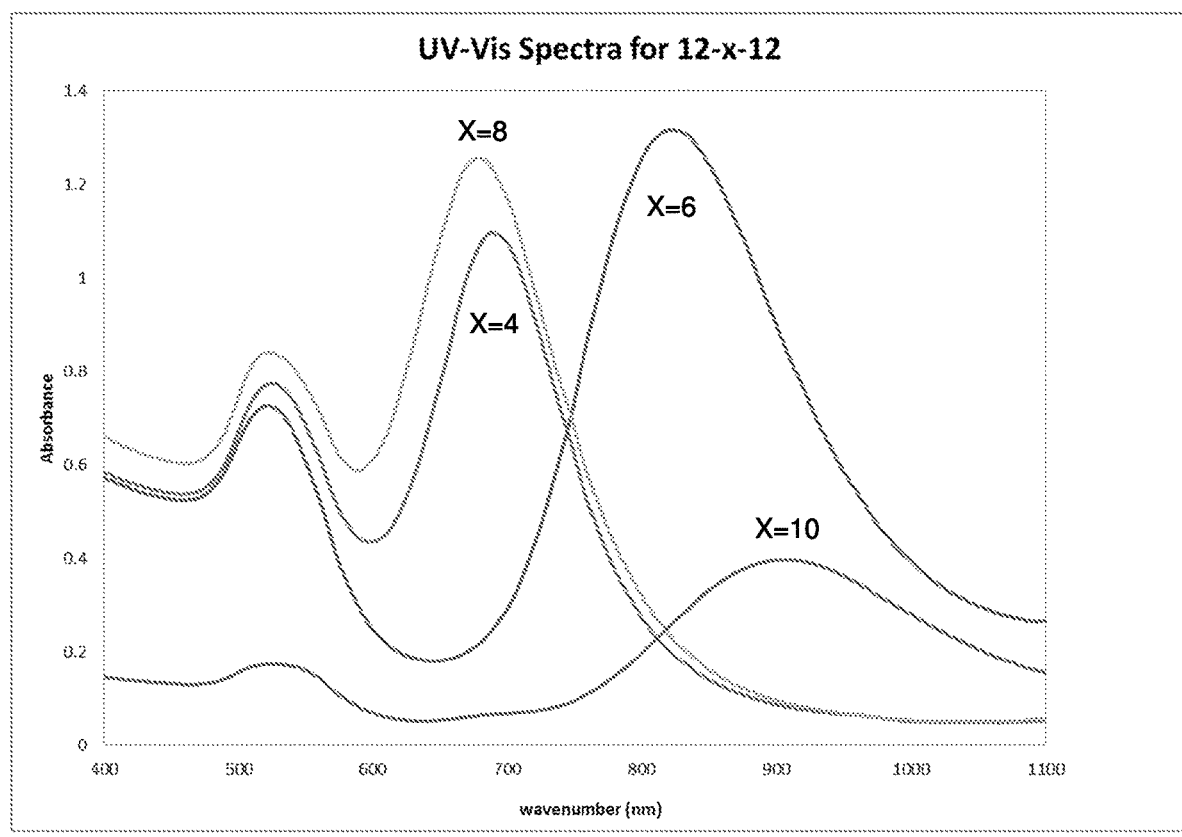
FIG. 13 shows the UV-Vis spectrum of gold nanorods produced with a 12 carbon gemini surfactant.
Figure 14:
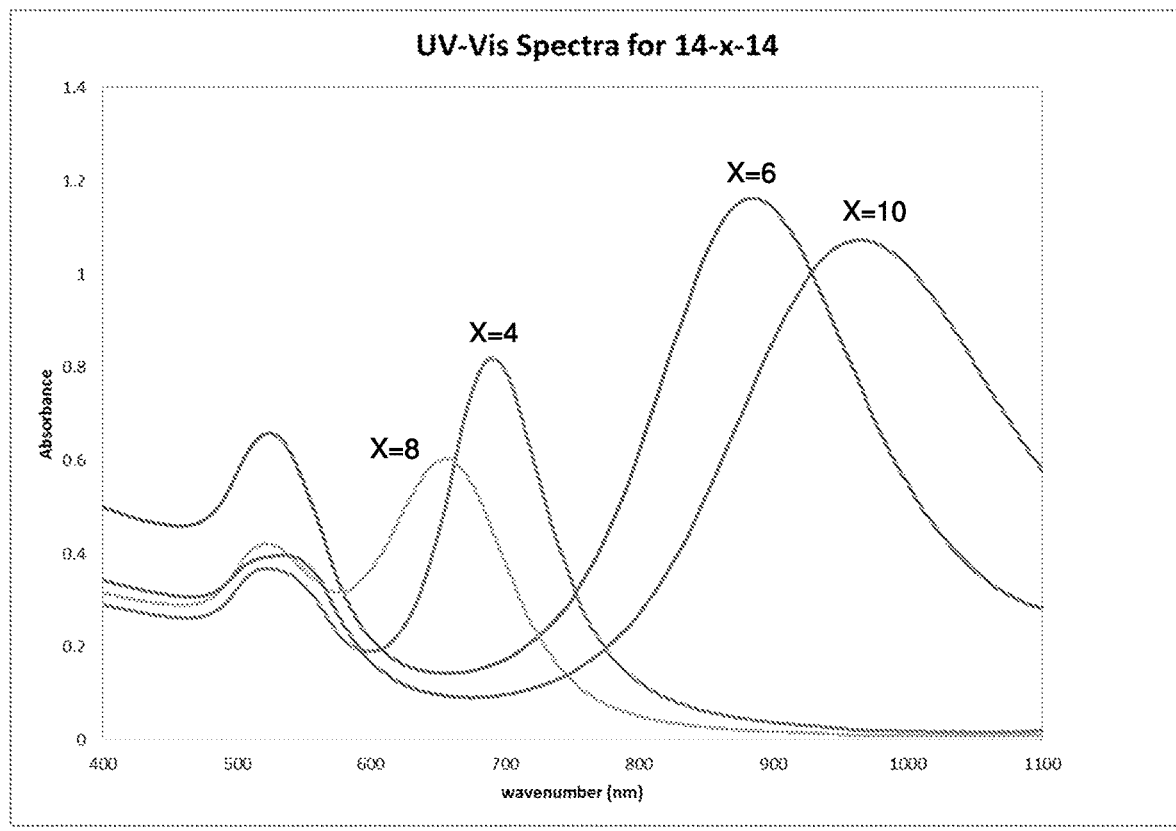
FIG. 14 shows the UV-Vis spectrum of gold nanorods produced with a 14 carbon gemini surfactant.
Figure 15:
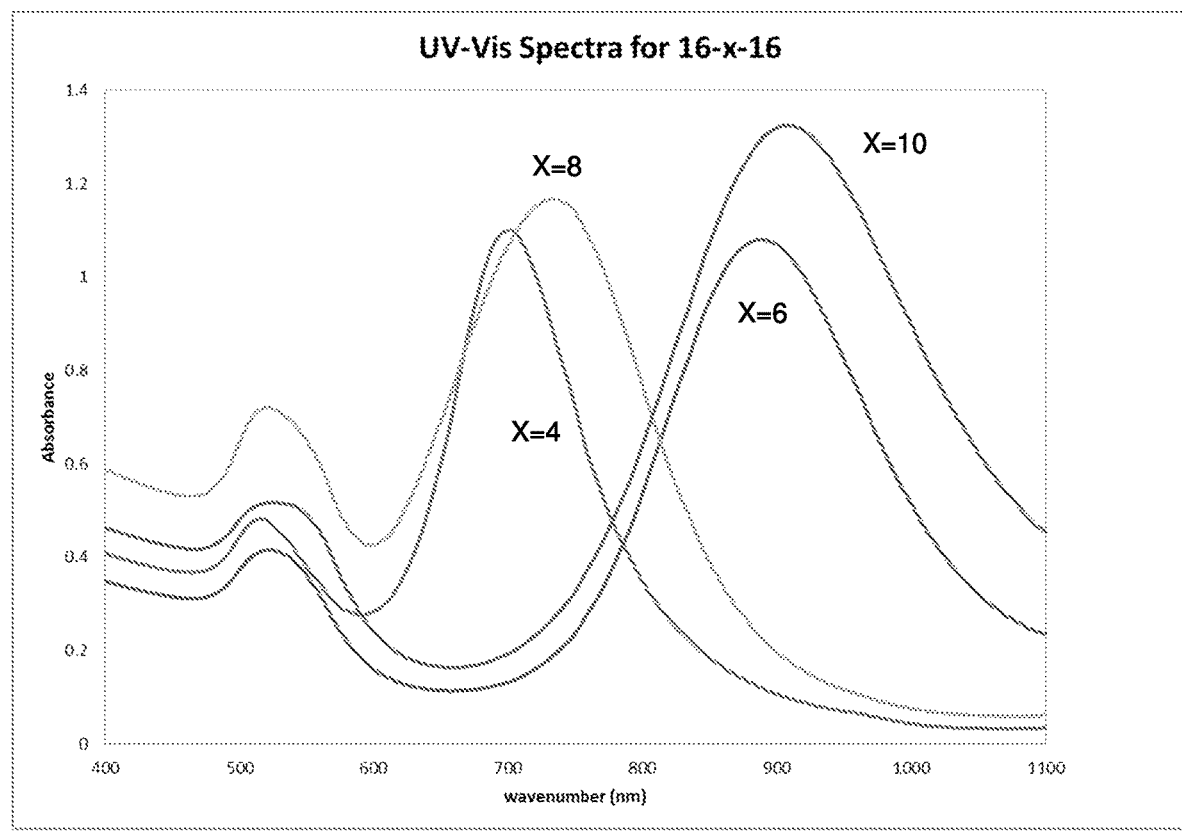
FIG. 15 shows the UV-Vis spectrum of gold nanorods produced with a 16 carbon gemini surfactant.
Figure 16:
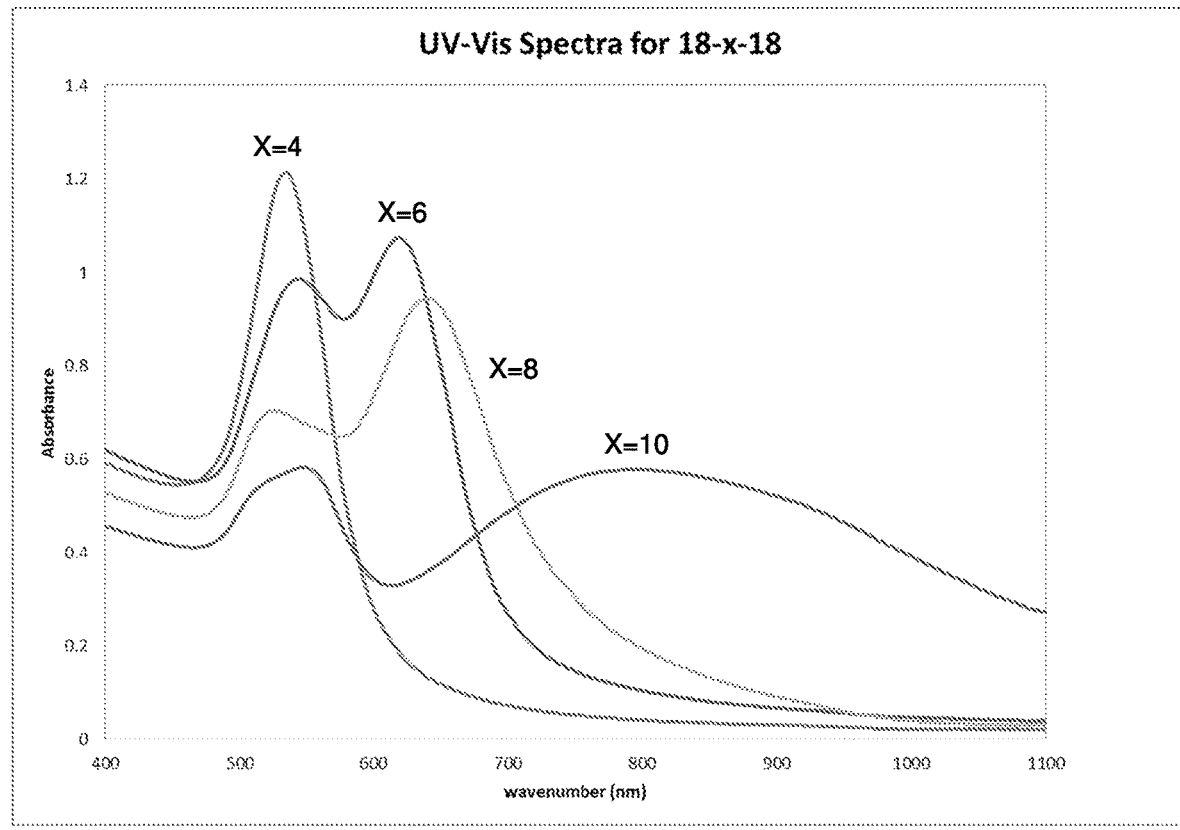
FIG. 16 shows the UV-Vis spectrum of gold nanorods produced with an 18 carbon gemini surfactant.
Figure 17:
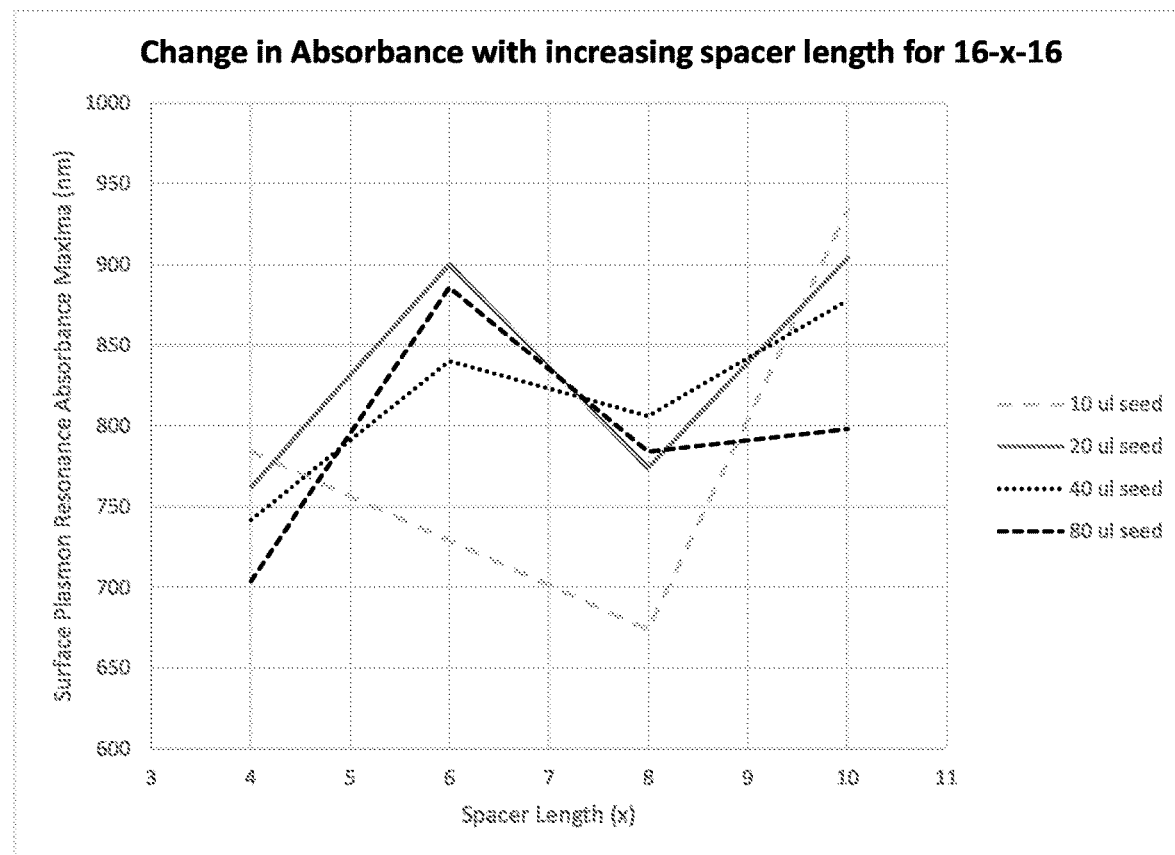
FIG. 17 shows the effect of spacer length on the length of gold nanorods produced using a 16-X-16 surfactant, where x is the spacer length.

In this example, about 0.30 g of stearyl betaine (about 95% pure) and about 0.08 g of Ammonyx™ MO (about 29 to 30 wt % myristyl dimethylamine oxide solution) were dissolved in about 20 ml of Nanopure water (e.g. triply deionized water or water that lacks conductivity). About 8 µl of about 30 wt % $HAuCl_4$ solution was added. About 10 µl of about 0.01 M ascorbic acid solution was then added. Nanorods started to form in the resulting mixture within about 10 to about 20 minutes and this solution of nanorods was allowed to age overnight without any stirring at about 27° C. Gold nanorods made by this procedure were characterized by transmission electron microscopy (TEM) (FIG. 2) and UV-Vis spectroscopy (FIG. 3). The gold nanorods produced by this method were shown to have various lengths but were particularly suited for rods possessing a high aspect ratio and significant length (e.g., rods that are about 15 nm wide and over about 100 nm in length). FIGS. 4-8 show the TEM and UV-Vis spectroscopy for gold nanorods produced using different amounts of stearyl betaine and Ammonyx™ MO.

In this method, a gold seed solution was not required for gold nanorod growth to occur and the reaction occurred in one pot. Furthermore, silver nitrate was not required for gold nanorod growth. The cytotoxic surfactant, CTAB, was not used and, in Its place, a non-toxic surfactant mixture was used.

Example 1a—Single-Pot Reaction Scale-Up to 4L-Shaken

In this example, about 22 g of stearyl betaine (about 95% pure) and about 6.6 g of Ammonyx™ MO were dissolved in about 3.7 L of nanopure water. This solution was then equilibrated at about 39° C. for about 1 hr, About 1 ml of about 30% $HAuCl_4$ was added to the solution and stirred. About 3 ml of about 0.1M ascorbic acid solution was added and stirred. The mixture was then transferred to a water bath set at about 24° C. and shaken at about 40 rpm overnight. UV-Vis spectroscopy indicated a peak close to about 541 nm and another upward incline starting at about 1050 nm.

In this method, a gold seed solution was not required for gold nanorod growth to occur and the reaction occurred in one pot. Furthermore, silver nitrate was not required for gold nanorod growth. The cytotoxic surfactant, CTAB, was not used and, in its place, a non-toxic surfactant mixture was used.

Example 1b—Single-Pot Reaction Scale-Up to 4L-Stationary

In this example, about 22 g of stearyl betaine (about 95% pure) and about 6.6 g of Ammonyx™ MO were dissolved in about 3.7 L of nanopure water. This solution was then equilibrated at about 39° C. for about 1 hr. About 1 ml of about 30% $HAuCl_4$ was added to the solution and stirred. About 3 ml of about 0.1 M ascorbic acid solution was added and stirred. The mixture was then transferred to a water bath set at about 24° C. and left undisturbed overnight (e.g. stationary). UV-Vis spectroscopy indicated a peak close to about 541 nm and another upward incline starting at about 1050 nm.

In this method, a gold seed solution was not required for gold nanorod growth to occur and the reaction occurred in one pot. Furthermore, silver nitrate was not required for gold nanorod growth. The cytotoxic surfactant, CTAB, was not used and, in its place, a non-toxic surfactant mixture was used.

Example 2—Production of Gold Nanorods Using a Gemini Surfactant

In this example, gold nanorods were made using a gold seed solution. The gold seed solution was made in a manner similar to the Murphy/EI-Sayad procedure described above (Adv. Mater., 2001, 13:1389; Chem. Mater., 2003, 15:1957), incorporated herein by reference, with CTAB having been replaced with the gemini surfactant N,N'-ditetradecyl-N,N,N',N'-tetramethylhexane-1,8-diaminium dibromide (14-6-14). The seed solution consisted of about 7.5 ml solution of about 0.025M of N,N'-ditetradecyl-N,N,N',N'-tetramethylhexane-1,6-diaminium dibromide (14-6-14), that had about 250 µl of about 0.01 M $HAuCl_4$ solution added to it. About 350 µl of about 0.01 M $NaBH_4$ solution was added. The resultant seed solution was allowed to sit for about 3-4 hrs, producing gold seeds.

About 40 µl of the seed solution, which contained residual $NaBH_4$, was then added to a growth solution, which was made in a separate flask (all reagents were scaled to a final volume of 20 ml). The growth solution contained about 0.025M of the of N,N'-ditetradecyl-N,N,N',N'-tetramethylhexane-1,6-diaminium dibromide (14-6-14), about 800 µl of about 0.01 M $HAuCl_4$, about 70 µl of about 0.01 M $AgNO_3$, and about 96 µl of about 0.1 M ascorbic acid. The nanorods started to form in the resulting mixture within about 10 to about 20 minutes and the solution of nanorods was allowed to age overnight without any stirring at about 27° C.

It was found that by varying the nature of the gemini surfactant, a variety of gold nanorods could be produced. Table 1 shows the amount of gemini surfactant that was used to make about 0.025M seed and growth solutions.

TABLE 1 amount of gemini surfactant used for seed and growth solutions

| Gemini Surfactant | Seed Amount (g) | Growth Amount (g) |
|---|---|---|
| 12-04-12 | 0.121 | 0.321 |
| 12-06-12 | 0.126 | 0.335 |

TABLE 1-continued amount of gemini surfactant used for seed and growth solutions

| Gemini Surfactant | Seed Amount (g) | Growth Amount (g) |
|---|---|---|
| 12-08-12 | 0.131 | 0.349 |
| 12-10-12 | 0.136 | 0.363 |
| 14-04-14 | 0.131 | 0.349 |
| 14-06-14 | 0.136 | 0.363 |
| 14-08-14 | 0.142 | 0.378 |
| 14-10-14 | 0.147 | 0.391 |
| 16-04-16 | 0.142 | 0.377 |
| 16-06-16 | 0.147 | 0.391 |
| 16-08-16 | 0.152 | 0.406 |
| 16-10-16 | 0.157 | 0.420 |
| 18-04-18 | 0.152 | 0.406 |
| 18-06-18 | 0.157 | 0.420 |
| 18-08-18 | 0.163 | 0.434 |
| 18-10-18 | 0.168 | 0.448 |

Example 3—Characterization of Gold Nanorods

Figure 18:
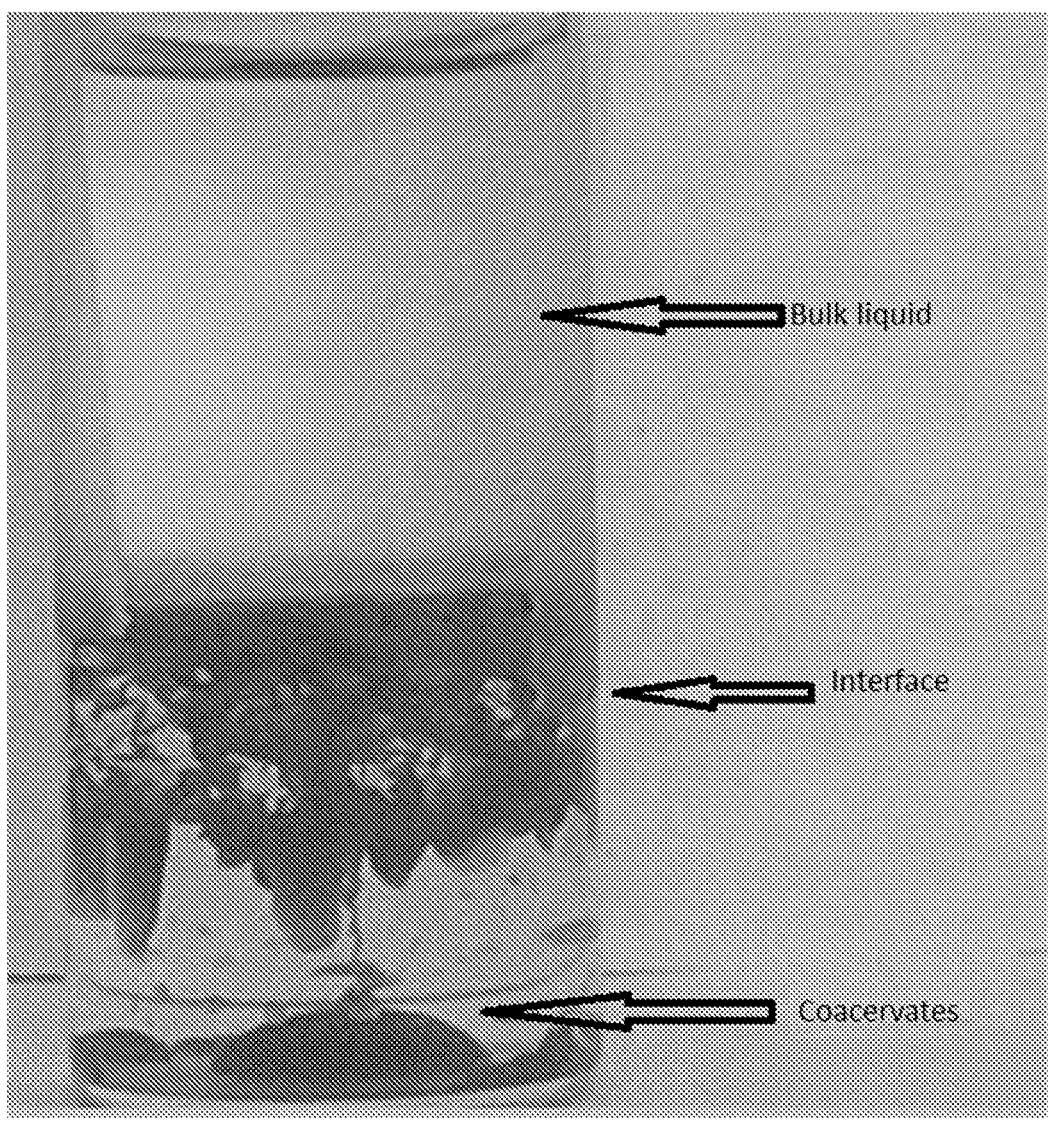
FIG. 18 shows an image of a gold nanorod system dispersed in a 14-6-14 gemini surfactant, separated using the coacervate separation method described herein.

Unpurified gold nanorods, made utilizing gemini surfactants of differing architectures as described in Example 1, 1a, 1b and 2, were characterized by transmission electron microscopy (TEM) (FIGS. 9-12), UV-Vis spectroscopy (FIGS. 13-16) and dynamic light scattering. Gold nanorods have been grown using both asymmetric and symmetric gemini surfactants. FIG. 18 shows the effect of spacer length on the length of gold nanorods produced using a 16-X-16 surfactant, where x is the spacer length.

Example 4—Purification of Gold Nanorods Using a Coacervate Method

In this example, the seed solution was made in a manner similar to Example 2. The growth solution contained about 0.025M N,N'-ditetradecyl-N,N,N',N'-tetramethylhexane-1,6-diaminium dibromide (14-6-14), about 30 µl of about 0.0017M sodium benzoate, about 800 µl of about 0.01 M $HAuCl_4$, about 70 µl of about 0.01 M $AgNO_3$, and about 96 µl of about 0.1 M ascorbic acid. The nanorods started to form in the resulting mixture within about 10 to about 20 minutes and this solution of nanorods was allowed to age overnight without any stirring at about 27° C.

Other gemini solutions useful for making gold nanoparticles were prepared in a similar fashion to the two examples given above.

Purification of the gold nanorods-containing solution prepared using the 14-6-14 gemini surfactant was accomplished by mixing the gemini-stabilized gold nanorod solution with 0.4-1.0 wt % of sodium salicylate, which resulted in the spontaneous formation of coacervates. Nanorod separation occurred during the coacervate formation.

Figure 19:
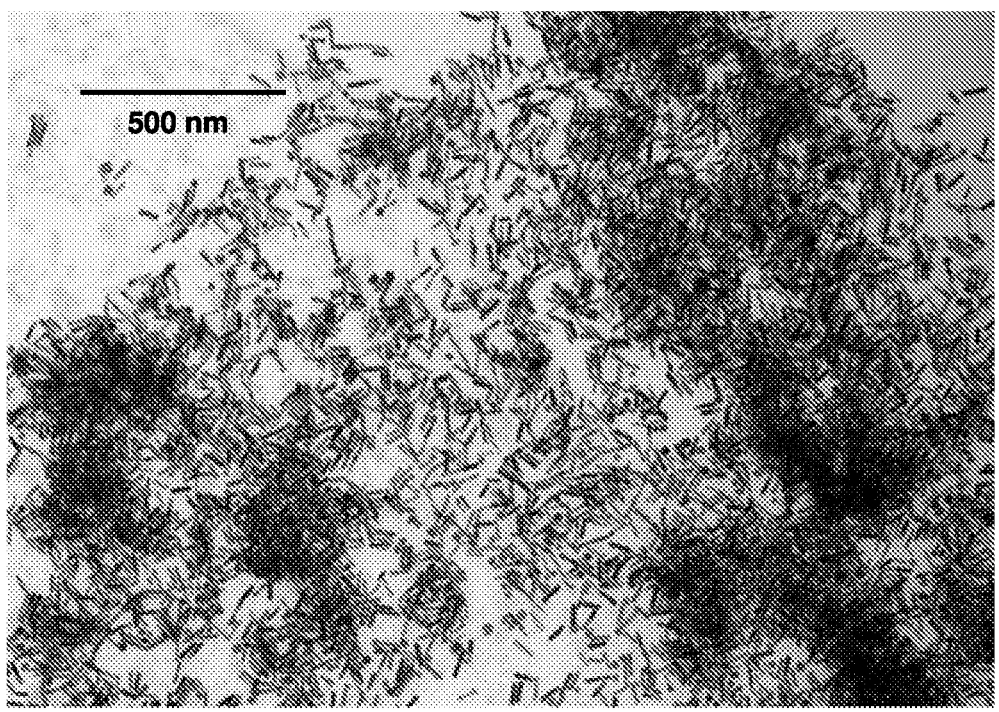
FIG. 19 shows the TEM of gold nanorods grown in a 14-6-14 gemini surfactant and purified using the coacervate separation method described herein.

The coacervate-containing solution was allowed to phase separate. The coacervate layer was collected (this was found to contain the gold nanorods of the desired length) and small particles were collected from the interfacial layer between the coacervates and the bulk solution. A picture of a gold nanoparticle solution treated in this manner is shown in FIG. 18 and a TEM of gold nanorods purified via the coacervate method is shown in FIG. 19.

Example 5—Purification of Gold Nanorods Using A Surfactant Blend Method

To separate the desired gold nanoparticles from some impurities, about 20 mL of the 14-6-14 gemini surfactant stabilized gold nanorod solution of Example 2 was centrifuged at about 22000 r.c.f for about 10 minutes at about 25° C. to form the gold nanoparticle pellet (i.e. a mixture of gold nanorods and other gold nanoparticles) and a solvent layer. The solvent layer was separated from the precipitated gold nanoparticle pellet and the pellet was re-dispersed in about 20 ml of nanopure water and centrifuged at about 22000 r.c.f. for about 10 minutes at about 25° C. to form the pellet and a solvent layer. The solvent layer was separated from the precipitated gold nanoparticle pellet.

Figure 20:
FIG. 20 shows the TEM of gold nanorods grown in a 14-6-14 gemini surfactant and purified using a surfactant blend separation method.

The gold nanoparticle pellet was re-dispersed in a small volume (5 to 10 ml) of a mixed surfactant solution. The mixed surfactant solution contained an amphoteric surfactant and a zwitterionic surfactant (about 0.10 g of Ammonyx MO, about 30% active matter and about 0.30 g of stearyl betaine, about 30% active matter) although other suitable combinations of surfactants can be used. The solution was left undisturbed for about 1 hr. The ionic strength of the solution was adjusted by adding an effective amount of a NaCl solution and left undisturbed for about 2.5 hrs to allow phase separation to occur and precipitate to form. The precipitate containing an excess of gold nanorods was dissolved in nanopure water. This separation technique utilizes the differential adsorption capacities of the two surfactants in the mixture with nanoparticles of differing geometries. Specifically, and without wishing to be bound by theory, it is believed that nanorods that are larger in size are trapped in surfactant precipitates leaving the impurities in the bulk solution. A TEM of gold nanorods purified via this method is shown in FIG. 20.

In another method, the gold nanorod gemini surfactant solution from Example 2 was spun in a centrifuge at about 22000 ref for about 10-20 min at a temperature of about 25-30° C. to form the gold nanoparticle pellet. The gold nanoparticle pellet was then dispersed in a mixture of about 0.11% EBB, about 0.17% of Ammonyx™ MO. About 0.8 ml of about 0.1 M acetic acid was added to adjust the pH to about 5.5. This solution was then spun in a centrifuge at about 300-4000 ref for about 10-20 min at a temperature of about 25-30° C. until a desired aspect ratio was achieved. This separation technique, again, utilizes the differential adsorption capacities of the two surfactants in the mixture with nanoparticles of differing geometries.

Example 6—Purification of Gold Nanorods Produced from Example 1a

About 1 L of the 4 L solution of the gold nanorods of Example 1a was added to a separating funnel and allowed to equilibrate at room temperature. A salt solution (about 14 g of NaCl dissolved in about 50 ml of nanopure water) was added to the separating funnel. After addition of the salt solution, the separating funnel was shaken and allowed to stand until the surfactant precipitate rose to the top. A resultant solvent layer was then separated by draining the solvent through a coarse filter paper and the surfactant precipitate of gold nanorods was collected on the filter paper.

Example 7—Purification of Gold Nanorods Produced from Example 1b

About 1 L of the 4 L solution of the gold nanorods of Example 1 b was added to a separating funnel and allowed to equilibrate at room temperature. About 42.5 to 45.5 ml of a salt solution (about 10 g of NaCl dissolved in about 50 ml of nanopure water) was added to the separating funnel. After addition of the salt solution, the separating funnel was shaken and allowed to stand until the surfactant precipitate rose to the top. A resultant solvent layer was then separated by draining the solvent through a coarse filter paper and the surfactant precipitate of an abundance of gold nanoparticle without gold nanorods (or at least less gold nanorods) was collected on the filter paper and the filtrate passes through.

The filtrate obtained above was added to a separating funnel. To a 50 ml vial holding about 5.5 to 7.5 ml of the salt solution (about 10 g of NaCl dissolved in about 50 ml of nanopure water), about 4 g of solid NaCl was added and nanopure water was added to achieve a final volume of about 30 ml. This solution was added to the filtrate in the separating funnel. The separating funnel was shaken and left undisturbed for about 10 to 15 hrs to allow and allowed to stand until the surfactant precipitate rose to the top.. A resultant solvent layer was then separated by draining the solvent through a coarse filter paper and the surfactant precipitate of gold nanorods was collected on the filter paper. The surfactant precipitate from this separation was dissolved in about 50 ml nanopure water to form a gold nanorod colloid for further processing. The surfactant precipitate obtained after addition of 42.5 to 45.5 ml of NaCl solution can be dissolved in 50 ml nanopure water for further processing.

Further purification of the precipitates in Examples 6 and 7 was accomplished by first dissolving the precipitates in nanopure water, up to a 50 ml total volume and centrifuging with one to three spins of about 3200 r.c.f. for about 10 min at about 30° C. After each spin, the top layer containing pure nanorods were separated from precipitates, including impurities, which settled at the bottom.

Example 8—Converting Longer Gold Nanorods to Shorter Gold Nanorods

Figure 25:
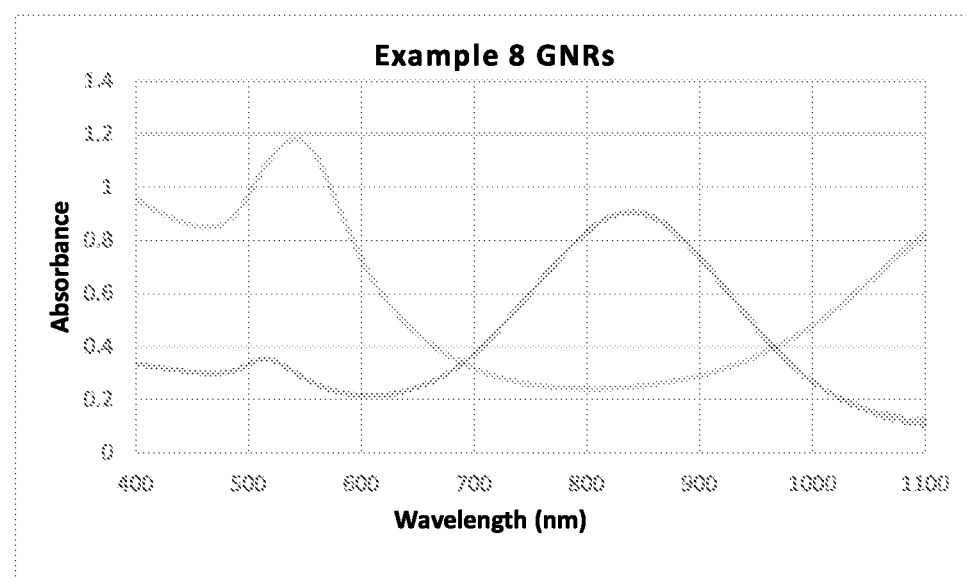
FIG. 25 shows a representative UV-Vis trace of non-seed gold nanorod production method (Example 8) showing nanorods prior to reaction (light grey) and after reaction (dark grey).

In this example, converting gold nanorods having a size of (about 10±3 nm)×(about 100±8 nm) and having an absorbance of about 1090 nm to gold nanorods having a size of (about 10±3 nm)×(about 45±5 nm) and having an absorbance of about 850 nm was provided. The surfactant precipitate containing an excess of gold nanorods from Examples 5, 6, or 7 were dissolved in about 50 ml of nanopure water. The solution was heated to about 75°G to dissolve the surfactant precipitate and kept at a temperature that cycled from about 85° C. to about 75° C., After about 30 min, the absorbance of the gold nanorod solution was measured close to about 850 nm. Additional heat cycles were performed such that the absorbance was 850 nm. FIG. 25 is a representative UV-Vis for the conversion of longer nanorods to shorter nanorods with longitudinal surface plasmon resonance close to about 850 nm.

Example 9—Dispersion Solution Exchange for Improved Colloidal Stability of Cold Nanorod Solution In this example, a gold nanorod solution, from any one of the methods of Examples 1-8, was spun in a centrifuge at about 22000 ref for about 10 min at about 25° C., producing a gold nanorod pellet and a solvent. About 95-98% of the solvent was removed and a similar amount of a mixture of about 0.11% EBB and about 0.17% of Ammonyx™ MO was added. A flask of the gold nanorod pellet solution was placed in an ultrasonic bath and the pH was adjusted to about 5.5 using about 5% acetic acid solution.

Figure 22:
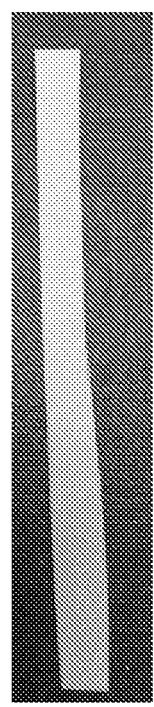
FIG. 22 shows polystyrene sulfonate wrapped gold nanorods showing smooth flow on 90 s nitrocellulose membrane.

The gold nanorods dispersion was found to be stable over 6 months. These gold nanorods were found to perform better in lateral flow assay development applications, such as with nitrocellulose membranes, (see FIG. 22).

Example 10—Curcumin Solubilization in Surfactant Bilayer of Gold Nanorods

Figure 21:
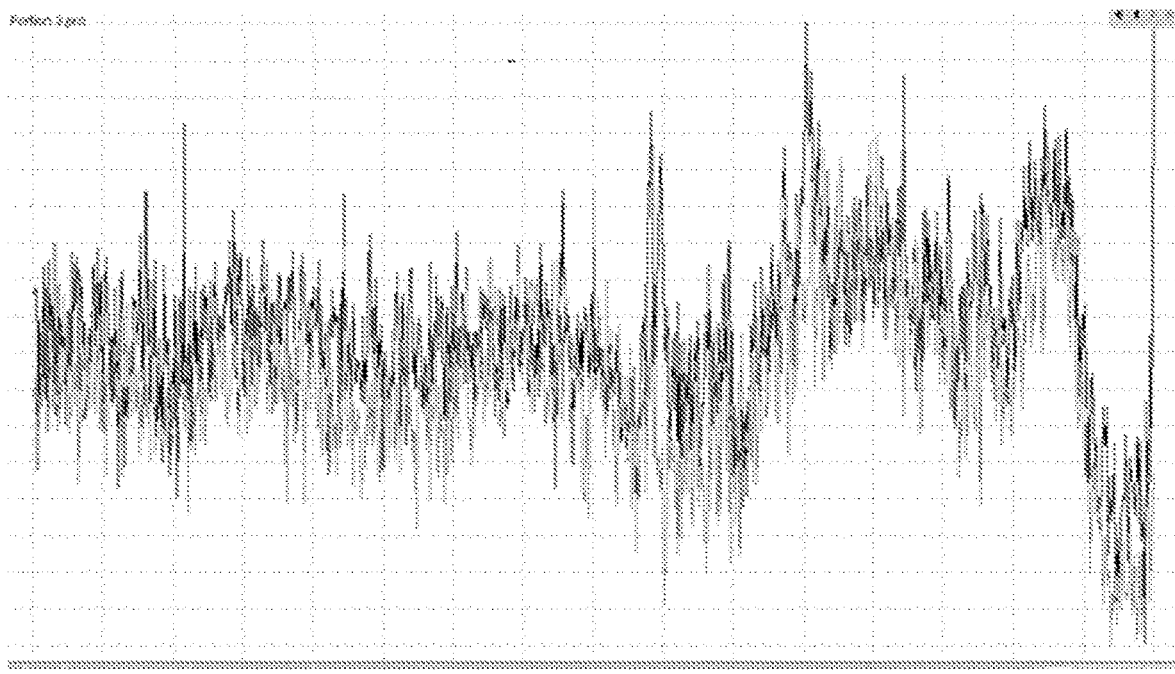
FIG. 21 shows a SERS spectrum of a curcumin-gold nanorod conjugate (black line) and a curcumin adsorbed in surfactant bilayer (gray line).

In this example, about 0.1% curcumin was dissolved in about 0.8 wt/v % T904™ polymer (BASF) solution, About 50 uL of this solution was added to the gold nanorod solutions (from Examples 1-9) and allowed to equilibrate for about 2 hrs at about 25° C.. The solubility of curcumin in a surfactant bilayer of the gold nanorod solutions was tested using DLS and SERS methods (see FIG. 21).

Example 11—Epigallocatechin gallate (ECGC) Solubilization in Surfactant Bilayer of Gold Nanorods In this example, about 4.4 mg of ECGC was dissolved in about 1.1 g of water to make an aqueous solution of ECGC. About 50 uL of this solution was added to about 4 ml of gold nanorod solutions (from Examples 1-9) and allowed to equilibrate for about 2 hrs at about 25° C., The solubility of ECGC in a surfactant bilayer of the gold nanorod solutions was tested using DLS and SERS methods like example 10.

Example 12—HIV CoA gp-41 (Recombinant Protein) Gold Nanorod Conjugate-Passive Binding About 2.9 mg of CoA gp-41 protein was dissolved in about 20 ml Nanopure™ water and dialyzed in phosphate buffer solution (pH was about 7.3) using a dialysis tube of about 14 kDa. About 0.2 ml of CoA gp-41 protein solution was mixed with about 1.8 ml gold nanorod solution (from Examples 1-9). The zeta potential of the gold nanorod solution changed from about +25 mV to about −7 mV upon this addition, which indicated the formation of a conjugate. As a standard test, about 0.4 ml of about 10% NaCl solution was added to check the stability of the conjugate and the conjugate was found to be stable. This is applicable to other recombinant proteins.

Example 13—Biotin Gold Nanorod Conjugate—Passive Binding

About 1 mg of solid biotin was dispersed in about 0.25 ml of gold nanorod solution (from Examples 1-9). This solution was shaken and incubated at room temperature for about 1 hr. Afterwards, excess biotin was removed by decanting. The formation of a biotin gold nanorod conjugate was tested and confirmed using a streptavidin capture line on a lateral flow assay strip. Various biotin concentrations, sizes and concentration of gold nanorods produces similar results.

Example 14—Curcumin Gold Nanorod Conjugate—Passive Binding

In about 1 ml of gold nanorod solution (from Examples 6 or 7) having an optical density (OD) of about 2.0, about 1 mg of curcumin was added and dispersed by shaking. This solution was then kept at about 70° C. for about 40 min. Afterwards, a strong signal in SERS was observed for this solution. Excess curcumin and surfactant were removed by a centrifuge method and the SERS signal was tested to confirm the formation of a curcumin gold nanorod conjugate. This method is applicable to other flavonoid, aromatic polyhydroxy compounds, and other small hydrophilic molecules.

Example 15—Polymer Wrapping of Gold Nanorods

About 1.5 ml of gold nanorod solution (from Examples 1-9) was spun in a centrifuge at about 22000 ref for about 10 min at about 25° C. About 95-98% of the solvent was removed to provide a gold nanorod pellet. About 100 uL of a polymer solution was added to the gold nanorod pellet and a vial containing the polymer solution and the pellet was place in an ultrasonic bath and the pellet was dispersed in the polymer solution to form polymer wrapped gold nanorods, Examples of the polymer solutions used were: about 100 uL (about 30 mg/ml) solution of thiolated polyethylene oxide (Mwt was about 1000, about 2000, or about 5000 kDa); about 1% polystyrene sulfonate solution; about 5% bovine serum albumin (BSA) solution; about 1% gelatin solution; about 0.1% beta casein solution; about 100 uL (about 30 mg/ml) solution of thiolated polyethylene oxide with carboxylic terminating ends; or about 100 uL (about 30 mg/ml) solution of thiolated polyethylene oxide with amine terminating ends.

Example 16—Negatively Charged Gold Nanorods

About 1.5 ml of gold nanorod solution (from Examples 1-9) was spun in a centrifuge at about 22000 ref for about 10 min at 25° C. About 95-98% of the solvent was removed and a similar amount of about 0.47 w/w % polystyrene sulfonate (PSS) solution (Mol. Wt. about 100 KDa) was added. This solution was then incubated at room temperature for about 20 min. Excess non-bounded polymer was removed by centrifugation where dilution was done using nanopure water. The zeta potential of this solution was measured between about −50 mV to about −58 mV. These gold nanorods were found to perform better in lateral flow assay development applications, such as with nitrocellulose membranes (see FIG. 22).

Example 17—Carboxy Functionalization of Gold Nanorods-Covalent Binding

About 1.5 ml gold nanorod solution (from Examples 1-9) was spun in a centrifuge at about 22000 ref for about 10 min at about 25° C. About 95-98% of the solvent was removed to provide the gold nanorod pellet. About 100 uL (about 30 mg/ml) solution of thiolated polyethylene oxide with carboxylic terminating ends (Mwt was about 1000, about 2000, or about 5000 kDa) was added to re-disperse the gold nanorad pellet. This solution was incubated for about 2-12 hrs and about 1.5 ml of nanopure water was added to provide carboxy ending thiolated polyethylene oxide wrapped gold nanorods. Excess polymer was removed using a centrifuge method.

Example 18—Amine Functionalization of Gold Nanorods-Covalent Binding

About 1.5 ml gold nanorod solution (from Examples 1-9) was spun in a centrifuge at about 22000 ref for about 10 min at about 25° C. About 95-98% of the solvent was removed to provide the gold nanorod pellet. About 100 uL (about 30 mg/ml) solution of thiolated polyethylene oxide with amine terminating ends (Mwt was about 1000, about 2000, or about 5000 kDa) was added to re-disperse the gold nanorod pellet. This solution was incubated for about 2-12 hrs and about 1.5 ml of nanopure water was added to provide amine ending thiolated polyethylene oxide wrapped gold nanorods. Excess polymer was removed using a centrifuge method.

Example 19—Covalent Conjugation of Gold Nanorods with Antibodies

In this example, covalent conjugation of IgG class of monoclonal antibodies was provided. About 1.5 ml of gold nanorods (from Examples 18 or 19 wrapped in carboxylic/amine ending thiolated polyethylene oxide (Mwt is about 3000)) were concentrated using a centrifuge. The gold nanorod solution was restored to about 50 uL volume with IgG antibody (about 1 mg/ml) solution in phosphate buffered saline (PBST) buffer with a pH of about 7.4. This solution was incubated for about 30 min at about 4° C. Afterwards, the solution volume was increased to about 1.0 ml using the PBST buffer solution with a pH of about 7.4 and centrifuged to wash excess antibodies. The gold nanorod pellet conjugated with the antibody was produced and re-dispersed in about 50 uL of PBST buffer.

Example 20—Passive Bio-Conjugation of Gold Nanorods with Antibodies

In this example, covalent conjugation of IgG class of monoclonal antibodies was provided. 1.0 ml of gold nanorod solution from example 1-9 and from example 15 and 16 were spun at about 22000 rcf for about 10 min at about 25° C. Supernatant was discarded and gold nanorod pellet was dispersed in 1 ml nanopore water. In another vial 100 uL of 25 mM borate buffer solution of pH 8.5 was obtained and to this solution 1.0 to 1.8 uL of antibody solution of concentration 6 mgml was added. These two solutions were mixed together and allowed to incubate for about 10 min at about 25° C. 20 uL of 10% BSA (bovine serum albumin) of pH 9.0 was added as blocking agent and solution was incubate for about 10 min at about 25° C. Excess antibodies and BSA was removed by centrifuge method. For people expert in art it is understood that this method can be applied to other class of antibodies, antibody fragments, and antibody mimics.

It will be understood that although the invention has been described above in relation to metal nanorods, other metal nanoparticles can be produced having different shapes, such as nanospheres. It will be understood that varying the concentration of metal cations and/or other reaction conditions, the methods described herein will result in nanoparticles of varying shapes.

It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to Its practice. It is therefore to be understood that the invention may be practiced otherwise than as specifically described without actually departing from the spirit and scope of the present invention as defined by the appended claims.

We claim:

1. A method for making metal nanorods, the method comprising:
combining a source of metal cations with at least one surfactant to form a mixture, wherein the metal cations are reduced and the metal nanorods are produced, the at least one surfactant comprises a first surfactant and a second surfactant, wherein one or more of the first surfactant and the second surfactant are different, and wherein the first surfactant is an amphoteric surfactant of formula (IV):

(IV)

wherein:
$R_1$ of formula (IV) represents a hydrophobic group, wherein the hydrophobic group comprises a substituted or unsubstituted hydrocarbon group, or a substituted or unsubstituted heterogeneous group; and
$R_2$ and $R_3$ of formula (IV) are each independently selected from hydrogen or a substituted or unsubstituted hydrocarbon group, or a substituted or unsubstituted heterogeneous group;
and the second surfactant is a zwitterionic surfactant of formula (I):

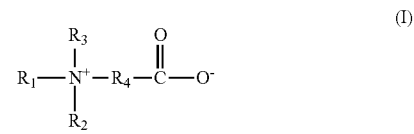

(I)

wherein:
$R_1$ of formula (I) represents a hydrophobic group, wherein the hydrophobic group comprises a substituted or unsubstituted hydrocarbon group, or a substituted or unsubstituted heterogeneous group;
$R_2$ and $R_3$ of formula (I) are each independently selected from hydrogen or a substituted or unsubstituted hydrocarbon group, or a substituted or unsubstituted heterogeneous group; and
$R_4$ of formula (I) is a substituted or unsubstituted hydrocarbon group, or a substituted or unsubstituted heterogeneous group,
wherein the metal nanorods have an aspect ratio of from about 1.1 to about 10 and the metal nanorods exclude metal nanowires.

2. The method of claim 1, wherein combining further comprises a reducing agent, optionally, the reducing agent is selected from the group consisting of ascorbic acid, glucose, glucosamine, hydroquinone, aluminum, calcium, hydrogen, manganese, potassium, sodium borohydride, sodium triacetoxyborohydride, compounds containing the $Sn^{2+}$ ion, such as tin(II) chloride, sulfite compounds, hydrazine, zinc-mercury amalgam, diisobutylaluminum hydride, oxalic acid, formic acid, phosphites, hypophosphites, phosphorous acid, dithiothreitol (DTT), compounds containing the $Fe^{2+}$ ion, such as iron(II) sulfate, carbon monoxide, carbon, tris(2- carboxyethyl)phosphine HCl, and combinations thereof, optionally, the reducing agent is ascorbic acid and/or sodium borohydride.

3. The method of claim 1, wherein the at least one surfactant forms wormlike micelles.

4. The method of claim 1, wherein at least one of: i) the first surfactant and the second surfactant have hydrocarbyl tails of substantially the same length, and ii) the second surfactant increases the solubility of the first surfactant.

5. The method of claim 4, wherein the second surfactant increases the solubility of the first surfactant.

6. The method of claim 1, wherein the zwitterionic surfactant is selected from the group consisting of alkyl N,N-dimethyl betaines, alkyl N,N-diethyl betaines, alkyl N-ethyl, N-methyl betaines, cocamidopropyl betaine, glycine betaine surfactants, or a combination thereof optionally, the zwitterionic surfactant is stearyl betaine.

7. The method of claim 1, wherein the amphoteric surfactant is myristyl dimethylamine oxide.

8. The method of claim 1, wherein the method is a single-pot reaction.

9. The method of claim 1, wherein the metal cations are selected from transition metal cations and combinations thereof, optionally, the transition metal cations are selected from precious metal cations and combinations thereof, optionally, the metal cations are selected from the group consisting of gold, nickel, palladium, platinum, copper, silver, zinc, cadmium, and combinations thereof, optionally, the metal cations are gold (I) or gold (III), optionally, the metal cations are gold (III).

10. The method of claim 1, wherein the source of metal cations comprises at least one metal salt, optionally, the metal salt is selected from the group consisting of gold (III) chloride, gold sodium thiomalate, gold sodium thiosulfate, triethylphosphine gold, gold sodium thioglucose, gold (III) bromide, gold (III) iodide, gold (III) nitrate, optionally, wherein the metal salt is gold (III) chloride.

11. The method of claim 1, wherein the method is cytotoxic surfactant-free optionally, the method is cytotoxic cationic surfactant-free, optionally, the method is CTAB-free.

12. The method of claim 1, wherein the mixture has a pH of about 4 to about 9.

13. The method of claim 1, wherein combining further comprises combining a solvent with the source of metal cations and the at least one surfactant optionally, the solvent is selected from the group consisting of water, low molecular weight alcohols, hydrocarbons, or mixtures thereof, optionally, the solvent is water, optionally, the water lacks conductivity.

14. The method of claim 1, wherein the metal nanorods produced by the method have a diameter of between about 5 nm and about 50 nm, from about 5 nm to about 30 nm, or from about 15 nm to about 30 nm.

15. The method of claim 1, wherein the metal nanorods produced by the method have an axial length of between about 20 nm and about 500 nm.

16. The method of claim 15, wherein the axial length is from about 30 nm to about 500 nm, from about 50 nm to about 300 nm, or from about 80 nm to about 100 nm.

17. The method of claim 1, wherein the metal nanorods are at least about 95% metal, at least about 96% metal, at least about 97% metal, at least about 98% metal, at least about 99% metal, at least about 99.9% metal, or at least about 99.99% metal.

18. The method of claim 1, wherein the metal is gold.

19. The method of claim 1, further comprising applying a targeting moiety to the metal nanorods, optionally, the targeting moiety is a protein and/or tumour-specific.

20. The method of claim 1, the method further comprises adding a metal salt and a phase separating surfactant for separating metal nanorods into a surfactant-rich phase of the phase separating surfactant-containing layer, optionally, the metal salt is selected from alkali metal salts, alkaline earth metal salts, transition metal salts, or combinations thereof, optionally, the metal salt is an alkali metal salt, optionally, the alkali metal salt is sodium chloride.

21. The method of claim 1, wherein the method further comprises centrifuging the metal nanorod solution to form a metal nanorod pellet and a solvent layer, separating the solvent layer from the metal nanorod pellet, adding solvent, and centrifuging.

22. The method of claim 1, wherein the method further comprises adding at least one solubilizate to a metal nanorod solution comprising the metal nanorods, optionally, the at least one solubilizate is a biomolecule, optionally, the biomolecule is selected from proteins, nucleic acids, polysaccharides, glycoproteins, flavonoids, vitamins, antioxidants, aromatic acids, amino acids, monohydroxybenzoic acid, monosaccharides, disaccharides, bile salt, nucleotides, or combinations thereof, optionally, the at least one solubilizate is selected from gelatin, beta casein, streptavidin, metal nanorod-streptavidin conjugate, bovine serum albumin, quercetin, epigallocatechin gallat, curcumin, curcumin, glutathione, oxy/deoxy cholic acid, anthranilic acid, cinnamic acid, biotin, p-hydroxybenzoic acid, or combinations thereof, optionally, the at least one solubilizate is adsorbed on a surfactant bilayer of the metal nanorods, optionally, an amount of the at least one solubilizate is from about 0.03% to about 20% (w/w); about 0.1% to about 20% (w/w); about 0.03% to about 10% (w/w); about 0.03% to about 5% (w/w); about 0.1% to about 15% (w/w); or about 0.1% to about 10% (w/w) based on total weight of the metal nanorod solution.

23. The method of claim 1, wherein the metal nanorods have a surfactant bilayer wrapped in a polymer, optionally, the polymer is selected from proteins, gelatin, bovine serum albumin, polystyrene sulfonate, polyethylene oxides, thiolated polyethylene oxides, thiolated polyethyene oxides with terminating carboxylic acid functionalities, thiolated polyethyene oxides with terminating amine acid functionalities, or combinations thereof, optionally, the polymer forms covalent or non-covalent bonds with at least one of a protein, a polypeptide, an antibody, an antibody fragment, an IgG class of antibody, a polyclonal antibody, a monoclonal antibody, or combinations thereof.

24. The method of claim 1, wherein the metal nanorods further comprise a capping agent optionally, a solvent or excess surfactant is removed from the metal nanorod solution followed by addition of an aqueous solution of the capping agent, optionally, the method further comprises removal of greater than about 95% of solvent from the metal nanorod solution, followed by the addition of a first capping agent, and removing of greater than about 95% of resultant solvent from resultant metal nanorod pellets, optionally, wherein the removing comprises centrifugation, optionally, further comprising dispersing the resultant metal nanorod pellets into an aqueous solution of a second capping agent.

25. The method of claim 24, wherein the metal nanorods are positively charged and have a charge of from about +5 to about +40 mV or the metal nanorods are negatively charged and have a charge of from about −5 to about −55 mV.

26. The method of claim 24, wherein the capping agent is a mixture of surfactant and a thiolated polymer, optionally, the capping agent is a mixture of surfactant, a co-surfactant, and small biomolecules, wherein the small biomolecules are selected from a general class of flavonoids, antioxidants, aromatic acids, amino acids, monohydroxybenzoic acid, monosaccharides, disaccharides, bile salt, nucleotides, or combinations thereof, optionally, wherein the method further comprises a co-capping agent selected from quercetin, epigallocatechin gallate, curcumin, glutathione, ascorbic acid, citric acid, anthranilic acid, cinnamic acid, bile acid, p-hydroxybenzoic acid, metal anionic salts of biological acid(s), or combinations thereof, optionally, wherein the method further comprises adding at least one solubilizate to a metal nanorod solution comprising the metal nanorods.

27. The method of claim 1, wherein the method further comprises extracting the metal nanorods and re-dispersing the metal nanorods in a surfactant composition comprising a stabilizing agent optionally, the extracting comprises centrifuging followed by re-dispersion into the surfactant composition with a pH adjuster, optionally, the stabilizing agent comprises at least one surfactant that has less carbon atoms than the at least one surfactant used to make the metal nanorods, optionally, the stabilizing agent comprises at least one alkyl glycine surfactant and at least one alkyl N-oxide surfactant.

28. The method of claim 1, wherein at least about 40% of the source of metal cations is reduced to nanoparticles; at least about 50% is reduced to nanoparticles; at least about 60% is reduced to nanoparticles; at least about 70% is reduced to nanoparticles; at least about 80% is reduced to nanoparticles; at least about 90% is reduced to nanoparticles; or at least about 99% is reduced to nanoparticles.

29. The method of claim 1, wherein $R_1$ is selected from unsaturated or saturated alkyl, unsaturated or saturated aralkyl, unsaturated or saturated heteroaralkyl, unsaturated or saturated alkoxyalkyl, and unsaturated or saturated alkylamidoalkyl, wherein each group may be substituted or unsubstituted, optionally, the alkyl of $R_1$ represents a group that contains from about 12 to 24 carbon atoms;

$R_2$ and $R_3$ are each independently selected from unsaturated or saturated alkyl, unsaturated or saturated aralkyl, unsaturated or saturated heteroaralkyl, unsaturated or saturated alkoxyalkyl, unsaturated or saturated carboxyalkyl, unsaturated or saturated hydroxyalkyl, unsaturated or saturated hydroxyalkyl-polyoxyalkylene, wherein each group may be substituted or unsubstituted, optionally, each of $R_2$ and $R_3$ group has from about 1 to 20 carbon atoms, from 1 to 10 carbon atoms, or from about 1 to 6 carbon atoms, optionally, wherein the alkyl of each $R_2$ and $R_3$ is independently selected from methyl and ethyl, the aralkyl is benzyl, the hydroxyalkyl is selected from hydroxyethyl and hydroxypropyl, and/or the carboxyalkyl is selected from acetate and propionate; and $R_4$ of formula (I) is an unsaturated or saturated hydrocarbyl group, optionally, an alkylene group having a chain length of from about 1 to 4 carbon atoms, optionally, $R_4$ is selected from methylene and ethylene.

30. The method of claim 1, wherein the metal nanorods produced by the method are substantially uniform in size and/or shape.

31. The method of claim 1, wherein the metal nanorods produced by the method are substantially uniform in at least one of length, diameter, and aspect ratio, wherein uniformity is a variance for at least one of the length, diameter, and aspect ratio of any metal nanorod in a population or subpopulation that can be at most 10% different from at least one of the average length, diameter, and aspect ratio for metal nanorods.

32. The method of claim 1, wherein the metal nanorods have a coating.

33. The method of claim 32, wherein the coating is biocompatible.

34. The method of claim 32, wherein the coating is polyethylene glycol, phospholipid, sugar chains, or antibodies.

35. The method of claim 32, wherein the coating is polyethylene glycol.

* * * * *